US012338447B2

United States Patent
Huang et al.

(10) Patent No.: US 12,338,447 B2
(45) Date of Patent: Jun. 24, 2025

(54) SPOTTED WILT DISEASE RESISTANCE GENE RTSW FROM TOBACCO AND USE THEREOF

(71) Applicant: YUNNAN ACADEMY OF TOBACCO AGRICULTURAL SCIENCES, Yunnan (CN)

(72) Inventors: Changjun Huang, Yunnan (CN); Yong Liu, Yunnan (CN)

(73) Assignee: Yunnan Academy of Tobacco Agricultural Sciences, Kunming (CN)

( * ) Notice: Subject to any disclaimer, the term of this patent is extended or adjusted under 35 U.S.C. 154(b) by 0 days.

(21) Appl. No.: 18/004,243

(22) PCT Filed: Oct. 12, 2022

(86) PCT No.: PCT/CN2022/124977
§ 371 (c)(1),
(2) Date: Jan. 4, 2023

(87) PCT Pub. No.: WO2024/077531
PCT Pub. Date: Apr. 18, 2024

(65) Prior Publication Data
US 2025/0092416 A1    Mar. 20, 2025

(51) Int. Cl.
*C12N 15/82*      (2006.01)
*C07K 14/415*    (2006.01)

(52) U.S. Cl.
CPC ........ *C12N 15/8283* (2013.01); *C07K 14/415* (2013.01)

(58) Field of Classification Search
CPC .......................... C12N 15/8283; C07K 14/415
See application file for complete search history.

(56) References Cited

FOREIGN PATENT DOCUMENTS

CN          107400674 B   *   7/2020   ........... C07K 14/005

OTHER PUBLICATIONS

Huang, C., Liu, Y., Yu, H., Yuan, C., Zeng, J., Zhao, L., . . . & Tao, X. (2018). Non-structural protein NSm of tomato spotted wilt virus is an avirulence factor recognized by resistance genes of tobacco and tomato via different elicitor active sites. Viruses, 10(11), 660. (Year: 2018).*

De Oliveira, A. S., Boiteux, L. S., Kormelink, R., & Resende, R. O. (2018). The Sw-5 gene cluster: Tomato breeding and research toward orthotospovirus disease control. Frontiers in Plant Science, 9, 1055. (Year: 2018).*

Goggin, F. L., Jia, L., Shah, G., Hebert, S., Williamson, V. M., & Ullman, D. E. (2006). Heterologous expression of the Mi-1.2 gene from tomato confers resistance against nematodes but not aphids in eggplant. Molecular Plant-Microbe Interactions, 19(4), 383-388. (Year: 2006).*

Laskowska, D., Doroszewska, T., Depta, A., Kursa, K., Olszak-Przybyś, H., & Czubacka, A. (2013). A survey of Nicotiana germplasm for resistance to Tomato spotted wilt virus (TSWV). Euphytica, 193, 207-219. (Year: 2013).*

(Y) Niedbała, G., Niazian, M., & Sabbatini, P. (2021). Modeling agrobacterium-mediated gene transformation of tobacco (*Nicotiana tabacum*)—a model plant for gene transformation studies. Frontiers in Plant Science, 12, 695110. (Year: 2021).*

(Z) Huang, H., Huang, S., Li, J., Wang, H., Zhao, Y., Feng, M., . . . & Tao, X. (2021). Stepwise artificial evolution of an Sw-5b immune receptor extends its resistance spectrum against resistance-breaking isolates of Tomato spotted wilt virus. Plant Biotechnology Journal, 19(11), 2164-2176. (Year: 2021).*

* cited by examiner

*Primary Examiner* — Amjad Abraham
*Assistant Examiner* — Dequantarius Javon Speed
(74) *Attorney, Agent, or Firm* — Harness, Dickey & Pierce, P.L.C.; Anthony G. Fussner

(57) ABSTRACT

The present invention relates to gene isolation and plant improvement, particularly to spotted wilt disease resistance gene RTSW from tobacco and use thereof. Provided are nucleic acid molecules for conferring or enhancing resistance to orthotospoviruses to a plant, and expression cassettes, vectors, host cells, plants and seeds comprising the nucleic acid molecules. The nucleic acid molecules encode RTSW gene products or variants thereof. Additionally provided are methods for conferring or enhancing resistance to orthotospoviruses to a plant, the method comprising introducing the nucleic acid molecules into plant cells.

9 Claims, 4 Drawing Sheets
Specification includes a Sequence Listing.

SEQUENCE LISTING

Sequence total quantity: 38
SEQ ID NO: 1          moltype = DNA   length = 4529
FEATURE               Location/Qualifiers
source                1..4529
                      mol_type = genomic DNA
                      organism = Nicotiana alata
SEQUENCE: 1
atggatactc aattagttag aggagaatca tctacatctt ctcacttctc ttatgaagta   60
ttcctcagtt ttagaggtga agacacccga aaaacattca ctgctcatct tttttccaaa  120
ttgtctgatg ttggagttaa taccttcatt gacgatgagg aattgagaaa gggtgacgtg  180
atttcaagag aattagaaa agcaattgaa gagtctagaa tttccattat tgttttctca  240
agaaattatg cttcctctag ttggtgtcta aatgaactag ttaagattct tgaatgcaaa  300
gagaaattta agcagatggt tttgcctatt tctatgatg ttgatccttc tgaggtacga  360
aaacaaactg ggttatttgg tgaagctttg gctaaacaca aggaacgacc atttggagct  420
caaagggtgg agaaatggag agctgcactt actgaagctg caaatctatc tggatgggat  480
ttgcaaaatg tggacgggta cattttcttg attcaactat agaatttcat tgttatttg  540
ttcaattgtt ttataggatg tgatactaac ggttaaaaaa gagtttaggt tttatacatt  600
gatattattg aaatatattt aaaatttatt ggaattaaat ccgtaaaata atttggatta  660
tattttaaat tcaagatata tccgttcaaa taaatttgta tatgttaaat tatttcttaa  720
aatatcctat atgacgtcgt aagttatcta ttttgtcgct tagattcatc ccactttgtt  780
atgtcttgct atcgattttg atttctccgt caaataattt caaatatcaa agttttattt  840
actgagctag tgtttctttt aattttttga ttttgctaaa aaatttgtag gcatgaatca  900
aagtttattg aaaaaataat acagcaagtc ctacaagtgg tcaaccagac acctctagat  960
gttgcttggc acccagttgg agtagattct cgtgtcaaag atatagagtt attattgcaa 1020
aatgaatgtg aagatgaagt tcgaatgatt ggtattcacg gagttggtgg catagggaaa 1080
acaactctag caaaagctat ctacaatcga atgtttcgac tcttcgatag tagttgcttc 1140
ctttcagatg ttagatcaga agctgaagaa tttggtcttg tcaagctaca agagaaactt 1200
cttcgacaaa ttctcaaaac tgaggacatc aaagttggca gtgttgctca aggcatcaat 1260
ctaatcaaag caagactcgg gtcaaagaag gttctaattg tcttgatga cgtggaccac 1320
agaaaccaat tagaatcctt aacaagagaa agaagttggt ttggttcggg tagttttaata 1380
atcactacca cccgagacaa gcgattgcta tgccggtttg agaaaaaaga gagatatgag 1440
gccaaactat taaatgacaa tgaagctatg ttacttttt gttggcatgc ttttgatagt 1500
cattttccac cagaagatta tgttaatttg gcacgagaca taatcagata ttcaggtagg 1560
ctaccattag ctccttgtgac attggggtta catttacaag gaagttctat agaagaatgg 1620
ggatatgaat tcgaaaaact aaaatcaatt cctcattgtg atatccaaaa gattctcaag 1680
ataagctttg atggacttga tgatgaaaca cagactgttt cctcgatat tgcatgcatc 1740

```
ttccatgggt tgatgagcg taaagttaat aaaatattaa atgcatgtgg ctttcatgct   1800
aaaagtgcaa ttacaacttt agtccaaaaa cacttgctcc aaagatcttg ggattatttg   1860
gtgatgcatg atctagtgcg agatatggga agatatattg ttcgcatgga atcagctcga   1920
gaccctggaa aacggagtag attgttcatc cctcaagaag tctgtgatgt tctacaagga   1980
aataaagtta gtaaatcttt tatccttat cttggttata atatatttt caatttaatt   2040
gtttattgct tataatgttg tcatcataat atataagtga attcattttg tgcttcgtct   2100
atggttagtt ttgtagtttt ttgtcaacca ttgtaaacta gaagttacat ttgctaaatt   2160
cttaactcac acccaaggcg gaaaaaaatc acctatttaa caattatcct aatttggtga   2220
tgcatatttc ttataaaatt cttataacta acatgctaat gggcatccac catagtatct   2280
ccatgattag ttattcaaag atatttgact ttacttaact aaatgcagaa attaagcttg   2340
ctcgaagaaa tcaggcatgt gaacgtttgg aaattgttga atccgtacat atgtgaaaca   2400
ttatttctag aacaatatgt acaaagtatt ctttcaaata tattcaaata tatcttctat   2460
cttctagtgc tattatcatg gttcccattc acacagtatc aatatgttct ctttattcat   2520
tttttccct ttgatattat catgtgaact tagtgaatgc tgctagccgg gtttgaaagg   2580
ctctcatctt agcttttga acaattttaa atttgtttaa catcctctaa tgtgtaagtt   2640
cattttgtt gatacatggt gtattctctt tgtttgtcca ccaatttgta taagcatttt   2700
ttctcgcgta atttctgata tttaacatgt gcttaagtta ctttttttt tactgagctg   2760
cagggttcca aaaatgtaga agtactgaag gtagatccag ggacattaaa gggagtgaac   2820
ttgagcacca aagcatttga gaaaatgaag aatcttaggg tgctcataat cgaggagtta   2880
catattagtg gagatttgg gctgttgtcc aagaagctca aatggttgtc ttggcaaaac   2940
tgtccttta aatatatacc atcaaattt ccagctgaga tcttgtagt tctagatatg   3000
cggaagagtg atatcgagga attcaattg aatttgcgag tttgttactc aatttacaa   3060
tttcatgtgt actgttattg ccactgagtg aaagaaaatg ttaattgaaa ctatatttgg   3120
tttactttta gtgttgtaga agtttgaaga agctgaatct ctctaattgc aagcaactca   3180
gaagcactcc aaacttcaat ggttcactga gtcttgagat tttgaatctc gatggttgcc   3240
taagtctgag ggagatccat ccatcaatag ggaatttgtc cagactaatt aaactatata   3300
tgcgtggttg cgaaaaactt acggatcttc ctagcagcat ttgccagcta aaatcccttg   3360
attacttgga cattgatggc tgctcattta taaaaacact gccagataac cttggagata   3420
tgaaagtct aagacatctt tctgcatctt atacgggtat aaaacaattg cctagatctg   3480
ttgaaatgct aagaaatctt aaaatattgg aagtgggaaa tcgaatgttt gggaccaata   3540
tgagtatta tggaagagga gtccatcaga tacaatattc cttgtcaact tttgtatccg   3600
atttgagact tacatactgt aatttgtccg aggctgatat tcctagggat attgggagct   3660
catcctcctt agaactttta gatttgagtg gcaacagttt ccattgtcta cctttgatt   3720
tttctaagtt acgattcttg aagggggttgt atttgattga ctgtgagaac cttcaaacac   3780
tcccgtcaat atcaaatta aagaattga acttcaaaat tgccaaaaat   3840
tggtcaagat tagagagttg gacaacctcc cttctatatg gtcgatcgac atgaggaatt   3900
gtagttgtct gcagaatcca ttcaatgaaa gcttcttcag tgcacctgct ctatcatttc   3960
catctagatt agtctctctc tctctctctc ctatcatatt aatgatcttg agtctttgtc   4020
cgatgcagca tgaaatagaa attagcattt atctggaatg caagagatt ccagaatgat   4080
gcaggaatcg agtaacaact tcatctatgt gtttgactat gcctacacat aataaggagt   4140
ataacttctt aggaatggtt ctctggttag tttccgactt ctctcatcca tgcttgtgga   4200
ttagtattgc ccataaacag ccttcaatta tggtgtggag tagtgtttat acaacacttg   4260
gtacacttga tggacacaca gaagtatcat gtgtacgtta catatcttac ttacatagag   4320
cttttgatgg ccagatgatc aaaggcgggg aaacgataga agcgtggtct gaagactcta   4380
caataaagaa gatagggatc catctgttat atttggacga atatggtaaa gttatatctt   4440
tgccgggaga cgtggatcat tcttattcta agtacccaaa aagagtttca acagtcttat   4500
caactcctcc ttataaaaga gcaaagttc                                    4529

SEQ ID NO: 2          moltype = DNA   length = 3267
FEATURE               Location/Qualifiers
source                1..3267
                      mol_type = other DNA
                      organism = Nicotiana alata
SEQUENCE: 2
atggatactc aattagttag aggagaatca tctacatctt ctccacttctc ttatgaagta     60
ttcctcagtt ttagaggtga agacacccga aaaacattca ctgctcatct tttttccaaa    120
ttgtctgatg ttggagttaa taccttcatt gacgatgagg aattgagaaa gggtgacgtg    180
atttcaagag aattagagaa agcaattgaa gagtctagaa tttccattat tgttttctca    240
agaaattatg cttcctcag ttggtgtcta aatgaactag ttaagattct tgaatgcaaa    300
gagaaattta agcagatggt tttgcctatt ttctatgatg ttgatccttc tgaggtacga    360
aaacaaactg ggttatttgg tgaagctttg gctaaacaca aggaacgacc atttggagct    420
caaagggtgg agaatggag agctgcactt actgaagctg caaatctatc tggatgggat    480
ttgcaaaatg tggacgggca tgaatcaaag tttattgaaa aaataataca gcaagtccta    540
caagtggtca accagacacc tctagatgtt gcttgctcag cagttggagt agattctgag    600
gtcaaagata tagagttatt attgcaaaat gaatgtgaag atgaagttcg aatgattggt    660
attcacggag ttggtggcat agggaaaaca actctagcaa aagctatcta caatcgaatg    720
tttcgactct tcgatagtag ttgcttcctt tcagatgtta gatcagaagc tgaagaattt    780
ggtcttgtca agctacaaga gaaacttctt cgacaaattc tcaaaactga ggacatcaaa    840
gttggcagtg ttgctcaagg catcaatcta atcaaagtga gactcgggtc aaagaaggtt    900
ctaattgttc ttgatgacgt ggaccacaga aaccaattag aatccttaac aagagaaaga    960
agttggtttg gttcgggtag tttaataatc actaccaccc gagacaagcg attgctatgc   1020
cggtttggag aaaaagagag atatgaggcc aaactattaa atgacaatga agctatgtta   1080
cttttttgtt ggcatgcttt tgatagtcat tttccaccag aagattatgt taattggca   1140
cgagacataa tcagatattc aggtagccta ccattactac ttgtgacatt ggggttacat   1200
ttacaaggaa gttctataga agaatgggga tatgaattcg aaaaactaaa atcaattcct   1260
cattgtgata tccaaaagat tctcaagata gcttgatg gacttgatga tgaaacacag   1320
actgttttcc tcgatattgc atgcatcttc catgggtttg atgagcgtaa agttaataaa   1380
atattaaatg catgtggctt tcatgctaaa agtgcaatta caactttagt ccaaaaacac   1440
ttgctccaaa gatcttggga ttatttggtg atgcatgatc tagtgcgaga tatgggaaga   1500
```

```
tatattgttc gcatggaatc agctcgagac cctggaaaac ggagtagatt gttcatccct    1560
caagaagtct gtgatgttct acaaggaaat aaaggttcca aaaatgtaga agtactgaag    1620
gtagatccag ggacattaaa gggagtgaac ttgagcacca aagcatttga gaaaatgaag    1680
aatcttaggg tgctcataat cgaggagtta catattagtg gagattttgg ctgttgtcc     1740
aagaagctca aatggttgtc ttggcaaaac tgtcctttaa aatatatacc atcaaatttt    1800
ccagctgaga atcttgtagt tctagatatg cggaagagtg atatcgagga atttcaattg    1860
aatttgcagt gttgtagaag tttgaagaag ctgaatctct ctaattgcaa gcaactcaga    1920
agcactccaa acttcaatgg ttcactgagt cttgagattt tgaatctcga tggttgccta    1980
agtctgaggg agatccatcc atcaataggg aatttgtcca gactaattaa actatatatg    2040
cgtggttgcg aaaaacttac ggatcttcct agcagcattt gccagctaaa atcccttgat    2100
tacttggaca ttgatggctg ctcatttata aaaacactgc cagataacct tggagatatg    2160
aaaagtctaa gacatcttc tgcatcttat acgggtataa acaattgcc tagatctgtt      2220
gaaatgctaa gaaatcttaa aatattggaa gtgggaaatc gaatgtttgg gaccaatatg    2280
agtattatg gaagaggagt ccatcagata caatattcct tgtcaacttt tgtatccgat      2340
ttgagactta catactgtaa tttgtccgag gctgatattc ctagggatat tgggagctca    2400
tcctccttag aacttttaga tttgagtggc aacagtttcc attgtctacc ttttgatttt    2460
tctaagttac gattcttgaa ggggttgtat tgattgact gtgagaacct tcaaacactc      2520
ccgtcaatat caaatttaga gaaacttgaa agaattgaac ttcaaaattg ccaaaaattg    2580
gtcaagatta gagagttgga caacctcccc tctatatggt cgatcgacat gaggaattgt    2640
agttgtctgc agaatccatt caatgaaagc ttcttcagtg cacctgctct atcatttcca    2700
tctagattag tctctctctc tctctcctc atcatattaa tgatcttgag tctttgtccg      2760
atgcagcatg aaaatagaaat tagcatttat ctggaatgca aagagattcc aagtgtcccc    2820
aggaatcgag taacaacttc atctatgtgt ttgactatgc ctacacataa taaggagtat    2880
aacttcttag gaatggttct ctggttagtt tccgactcct ctcatccatg cttgtggatt    2940
agtattgccc ataaacagcc ttcaattatg gtgtggagta tgtttatac aacacttggt      3000
acacttgatg gacacacaga agtatcatgt gtacgttaca tcttactt acatagagct       3060
tttgatggcc agatgatcaa aggcggggaa acgatagaag cgtggtctga agactctaca    3120
ataaagaaga tagggatcca tctgttatat tggacgaatg atggtaaagt tatatctttg    3180
ccgggagacg tggatcattc ttattctaag tacccaaaaa gagtttcaac agtcttatca    3240
actcctcctt ataaaagagc aaagttc                                         3267

SEQ ID NO: 3            moltype = AA  length = 1089
FEATURE                 Location/Qualifiers
source                  1..1089
                        mol_type = protein
                        organism = Nicotiana alata
SEQUENCE: 3
MDTQLVRGES STSSHFSYEV FLSFRGEDTR KTFTAHLFSK LSDVGVNTFI DDEELRKGDV       60
ISRELEKAIE ESRISIIVFS RNYASSSWCL NELVKILECK EKFKQMVLPI FYDVDPSEVR     120
KQTGLFGEAL AKHKERPFGA QRVEKWRAAL TEAANLSGWD LQNVDGHESK FIEKIIQQVL     180
QVVNQTPLDV AWHPVGVDSR VKDIELLLQN ECEDEVRMIG IHGVGGIGKT TLAKAIYNRM     240
FRLFDSSCFL SDVRSEAEEF GLVKLQEKLL RQILKTEDIK VGSVAQGINL IKARLGSKKV     300
LIVLDDVDHR NQLESLTRER SWFGSGSLII TTTRDKRLLC RFGEKERYEA KLLNDNEAML     360
LFCWHAFDSH FPPEDYVNLA RDIIRYSGRL PLALVTLGLH LQGSSIEEWG YEFEKLKSIP     420
HCDIQKILKI SFDGLDDETQ TVFLDIACIF HGFDERKVNK ILNACGFHAK SAITTLVQKH     480
LLQRSWDYLV MHDLVRDMGR YIVRMESARD PGKRSRLFIP QEVCDVLQGN KGSKNVEVLK     540
VDPGTLKGVN LSTKAFEKMK NLRVLIIEEL HISGDFGLLS KKLKWLSWQN CPLKYIPSNF     600
PAENLVVLDM RKSDIEEFQL NLQCCRSLKK LNLSNCKQLR STPNFNGSLS LEILNLDGCL     660
SLREIHPSIG NLSRLIKLYM RGCEKLTDLP SSICQLKSLD YLDIDGCSFI KTLPDNLGDM     720
KSLRHLSASY TGIKQLPRSV EMLRNLKILE VGNRMFGTNM SIYGRGVHQI QYSLSTFVSD     780
LRLTYCNLSE ADIPRDIGSS SSLELLDLSG NSFHCLPFDF SKLRFLKGLY LIDCENLQTL     840
PSISNLEKLE RIELQNCQKL VKIRELDNLP SIWSIDMRNC SCLQNPFNES FFSAPALSFP     900
SRLVSLSLSP IILMILSLCP MQHEIEISIY LECKEIPEWC RNRVTTSSMC LTMPTHNKEY     960
NFLGMVLWLV SDFSHPCLWI SIAHKQPSIM VWSSVYTTLG TLDGHTEVSC VRYISYLHRA    1020
FDGQMIKGGE TIEAWSEDST IKKIGIHLLY LDEYGKVISL PGDVDHSYSK YPKRVSTVLS    1080
TPPYKRAKF                                                            1089

SEQ ID NO: 4            moltype = DNA  length = 1875
FEATURE                 Location/Qualifiers
source                  1..1875
                        mol_type = genomic DNA
                        organism = Nicotiana alata
SEQUENCE: 4
agccaaacac caattctttc cctttacttt ccattttaaa tttcatgttt gtaaaaatat       60
atcacataaa ttgagacaga tgaaataaat gaatttgac caatttttc aattcacttg       120
ccgataataac aaaagggatt aaaaaaaaaa gactttgag atgcaaaaga aaagaatccc     180
gcaaacaact tgtagagtat ttctacccaa tacgaaaaag ggaaattacc agctatgtcc     240
atttagaagt atcccattac aaaaattggc caattaataa aatattaca atattagcca     300
aaatggccaa ttaactattt gtagcaaaaa aatatcaaat ttttactttc ttttgagttg     360
gtgctattag aatagattgg gtatatctta aggagcttga atctcagttt tgggatgatt     420
tggtgaagtt ttgacgtggt ttaaattgaa aattcgaagt aaaaactgaa tatgaaaaaa     480
aatgatacat gtattacact gtgtatcaca tatgtatcat atttgtatcg attgtgtatc     540
acatgtatat ctgtgtgtga gatacatgtg tgatacatgt ttgatacatg tgtcacagaa     600
gaatttttg acatcgattt aactatgaat tttgataaa aaccagtcaa aatcaccccc        660
aatcttcatc aaattttgta tattgactta tctatatgtt tcaatgaatt tcgactata      720
cccattaaaa aaattccttg tttatttcga ttttggaata ttggctagag ttggtaagt      780
tgaaacttat atgggacatt ttgtaagttt ccctacgaa aaatccaaa agtaatttcc       840
tagaacaact tacaaactgt gaactatact gcatgcattt tacttcctt tcagtaact       900
cttgtttaat cttattcgat taaatttatg aatattttt cagtttgtaa tggcctaata     960
```

```
ttttaaaagg aatttgcaaa attcttattt catcactata caagaaaata cactcaaggg  1020
tcatatagga tctgtgaatt cagaggtgga tccgggattt gatggttatg agtgtcatcg  1080
cttttaatgc attttgtcag tttgatccat tttgaattaa tttggttcga tctattttaa  1140
ttttgtagat ttacaatatg agttacagcg tgaactttat ttacactata agactaagag  1200
cccgtttggc ttagctgatt tagagtagct gataagcaat aggtactgaa aagcacttt  1260
aagtgctgaa actgatttaa aaaataagca gttacgtgtt tggataaaag tgctgaaatt  1320
aataatatgc agctgaagaa ctgggtatac gaagagtttt gttttaaaaa gaagtatttt  1380
agggatagaa tagtaaatat tttggtcaaa cttaaagtgc ttataagctg aaatttgata  1440
agttggggga gaccaactta tgacttttgg ctttattttg gcttataagc acttaactta  1500
taagcatttt taattttacc aaacgcgtag ataagccaaa aagtgcttat aagtcagttt  1560
gaccagctta taagcttagc caaacaccct ctaagagtct gtttggaaaa ggtgtaatta  1620
ttttaagtga ttttttaaaat tatcattgcc aaaaactaat tacgaaaaaa gtacaacaaa  1680
aaaaaaaag agtataggaa aaggtgaaat tatggcgaaa gtggaaatcc acaaaatttc  1740
atggcattcc gtttaatttc tttttaaggt tgacttgact tccacaaagg aagacctctg  1800
cttatatgta gctctgctac tttcccttta ctgaaaaatt cattccttaa ttcttggatt  1860
ctcatcaacc cttaa                                                    1875

SEQ ID NO: 5           moltype = DNA   length = 4630
FEATURE                Location/Qualifiers
source                 1..4630
                       mol_type = genomic DNA
                       organism = Nicotiana alata
SEQUENCE: 5
atggatactc aattagttag agtagaatca tctacatctt ctcacttctc ttatgaagta  60
ttcctcagtt ttagaggtga agacatccga aaaacattca ctggtcatct ttattccaaa  120
ttagataatg ttggagttaa aaccttcatc gacgacgagg aattgagaaa gggtgacgtg  180
atttcaagta aactagagaa agcaattgaa gagtcacgaa tttccattat tgttttctca  240
agaaattatg cttcctctag ttggtgtcta aatgaactag ttaaaattct tgaatgcaaa  300
gagaaattaa agcatatggt ttttcctatt ttctatgatg ttgatccttc tgaggtacga  360
aaacaaactg ggttattggt tgaagctttg gctaaacaca ggaacgacc atttggagct  420
caaatggtgg agaaatggag agctgcactt actgaagctg caaattttc tggatgggat  480
ttgcaaaatg ttgctgacgg gtacatattc ttgattcaac tatagaattt cagttgttat  540
tagttcaatt gttttatagg atgtgatact aacggttaaa aaagagttta ggttttatac  600
attgatatta ttaaaatata tttaaaattt atcggaatta aatccgtaaa ataatttgga  660
ttatattta aattcaagat atatcagttc aaataaattt gtatatgtta aattattct  720
taaaatatcc tatatgacgt cgtaagttat ctattttgtt gctagaattc atcccacttt  780
gttatgtctt gctatcaatt ttgatttctc cgtcaaataa tttcaaatat caagttttta  840
tttactggag tagtgtttct tttaattttt tgatttgct aaaaaatttg taggcatgaa  900
tcaaagttta ttgaaaagat tatacagcaa gtcctacaag tggtcaacca gacacctca  960
gatgttgctt ggcacccagt tggagtagat tcttctgtca agatataga gttattattg  1020
caaaatgaat gtgaagatga agttcgaatg attggtattc acggagttgg tggcataggg  1080
aaaacaactc tggcaaaagc tatgtacaat cgaatgtttc gactcttcca tagtagttgc  1140
ttcctttcag atgttagatc agaagctgaa gaatttgtc ttgtcaagct acaagagaaa  1200
cttcttcaac aagtactcaa aactaaggac atcaaagttg gcagtgttgc tcaaggcatc  1260
aatctaatca agcaagact gggtcaaag aaggttctga ttgttcttga tgatgtggac  1320
cataaaagac agttagaagc cttaacaaga gaaagaggtt ggtttggttc gggtagttta  1380
ataatcatta ccaccgaga cgagcaattg ctatgtcggc ttggagaaaa agagagatat  1440
gaggctgaac tattaaatga caatgaagct caacaacttt tcagttgtca tgcttttgac  1500
agtccttctc caccactaga atatgttagt ttggcacatg acgtaatcga atattcaggt  1560
aggctaccat tagctcttgt gacattggcg tcacatttgc aaggaagttt tgtagaagaa  1620
tggggatatg aattcgaaaa actaagagca atacctcata ttgatatcca aaagattctc  1680
aagataagct ttgatggact tgatggtgat acacaaactg tgttccttga tattgcgtgc  1740
gccttccatg ggttttatga gcatgaagtt acagaaatat aaatgcatg tggctttcat  1800
gctaaaagtg caattgcaac tttagtccga aaacacttgc tccaaggatc tccgtgtcgt  1860
ttgaagatgc atgatctagt gcgagatatg ggaagagaaa ttgttcgcat ggaatcagct  1920
cgagaacctg gaaacgggag tagattgttc atccctcaag aagttcgtaa tgttctacaa  1980
ggaaatgaag tcagtaaatc cctcatcatt atcttggtta tatatttttt caattaaatt  2040
gtttcttact tataatttct attgtcatca taagaaatca tttctgcttc gtctctggtt  2100
agtaagtatt ttgtagttgt ttgtcaatca ttgtgaacta gaaatgacat ttgctaaatt  2160
cttaactaac accaaaggca aaacaataaa taaaatcac ctatttaata attatccaaa  2220
tttggtgatg catatttctt attaaattct tataactagc atgcttatcg gcataaacca  2280
tagtatctcc gtgattagtt attcaaagat atttgagttt acttaactaa atgcggaaat  2340
taaacttgct cgaagaaatc aagcatgcga ccatttgaaa actgttgaat aggtacatat  2400
gtgaaacatt atttctagaa cgtatatatac aaaatgttct tttaaatata ttcaaatata  2460
tattcgatct tcatttggcg ctattatcaa gtttctagat gcaatttgtt ctctttattc  2520
atcattttt ttccttgat attatcatgt gaacttattg aatgctgcta gccaattttg  2580
gaaggctctc atcttagctt gagcaatttt aaatttgttt aacatcctct aggttcaatt  2640
ttgttgatac atggtgtatt ctctttgttt gtccaccaat ttttataaag cattttctcg  2700
cttaatttct tggacttttaa catgagttaa gttacttttc tttttactga gctgcagggt  2760
tccgaaaatg tagaagtact gaaggtagat cgagggacta taaacggagt gaacttgagc  2820
accaaagcat ttgagcgaat gaagaatctt agggtgctta taatcaatga cgagttatat  2880
attagtggag attttgggat gttgtccaat aagcttagat ggttgtcttg aaagaatgt  2940
ccttttaaaat gtataccatc aaattttccc gctgagaatc ttgtagttct agatatgcgg  3000
aagagtgata tcgaggaatt tcaattgaat ttgcaggttt gctactcaat tttacaattt  3060
catgtgtact gttattgcca ctgagtgaaa gaaaatgtta attgaaacta tatttggttt  3120
acttttagtg ttgtagaagt ttgaagaagc tgaatctctc taagtgcaag caactcagaa  3180
gcactccaaa cttcaatggt tcactgagtc tggagatttt gaatccca ggttgcctaa  3240
gtctgaggga gatccatcca tcaataggga atttgtccag actaattaaa ctatatatgc  3300
gtggttgcga aaaacttacg gatcttccta gcagcatatg ccagctaaaa tccccttgatc  3360
```

-continued

```
acttggacat tgatggctgc tcatttataa aaacactgcc agataacctt ggagatatga   3420
aaagcctaag acatctttat gcatctggta caggtataaa acaattgtcc agatctattg   3480
aaatgctaag aaatcttgaa actttgagag tggaaggtga aaagttagag gccaaaagga   3540
gtatttctgg aagaggagtc catcagatac aatattcctt gtcaactttt gtatccgatt   3600
tgagacttac atactgtaat ttgtccgagg ctgatattcc tagggatatt gggagcttat   3660
cctcctttga acttttagat ttgagtggta acagttttaa ttgtctacct tttgattttt   3720
ctaagttacg attgctgaag gtgttgtgtt tgaatgattg tgagaatctt caaacactcc   3780
agtcagtatc aaatttagag aatcttgaaa ttccttgatct tgaaaattgc gaaaaattgg   3840
tcaagattac agagttggac aacctcccct ctatatggtg gatcaacatg attaattgta   3900
gttgtctgca gaatccattc aatgaaggct tctttagtgc acctgctctc tctagaaaag   3960
atcgagatat gtttagaaaa atggttagtc tgtctctttc tctctctctc tgctatcata   4020
ttaatgatct tgagtctctg tctgatgcag tgtgaaatag aatttatctc gaatgccaa    4080
gagattctag aatggtgcag gaatcaagta acaacttcat ctatgtgttt gactatgccg   4140
acacataata aggagtataa cttcttagga atggttctct ggcttgtttt cgacttctct   4200
ttggatgtag cctctcttcc atgcttgtgg attagtattg cccataaaca gccttcactt   4260
atggggtggc gtggtgttct acaacacttg aagtatcatg tgtaagtta catatcttac    4320
ttacatagag cttttgatgg ccagatgatc aaaggtgggg aaaggataga agtgtggtct   4380
gagcacatta caataaagaa gatagggatc catctgttat atttggacga atatggtaaa   4440
gttatatctt tgccgggaga cgtggatcat tcttattcta agtacccaaa aagagtttca   4500
acaggcttat tatcaactcc tccttataaa agagcaaagt tctgagtcaa gataattttc   4560
cttttagagct aatcaaattg tatttatatt acactattaa tgtgtagttg atcagttaat   4620
ttttaattga                                                          4630

SEQ ID NO: 6           moltype = DNA  length = 2454
FEATURE                Location/Qualifiers
source                 1..2454
                       mol_type = other DNA
                       organism = Nicotiana alata
SEQUENCE: 6
atggatactc aattagttag agtagaatca tctacatctt ctcacttctc ttatgaagta   60
ttcctcagtt ttagaggtga agacatccga aaaacattca ctggtcatct ttattccaaa   120
ttagataatg ttggagttaa aaccttcatc gacgacgagg aattgagaaa gggtgacgtg   180
atttcaagta aactagagaa agcaattgaa gagtcacgaa tttccattat tgttttctca   240
agaaattatg cttcctctag ttggtgtcta aatgaactag ttaaaattct tgaatgcaa    300
gagaaattaa agcatatggt ttttccatatt tctatgatg ttgatccttc tgaggtacga   360
aaacaaactg ggttatttgg tgaagctttg gctaaacaca aggaacgacc atttggagct   420
caaatggtgg agaaatggag agctgcactt actgaagctg caattttttc tggatgggat   480
ttgcaaaagtg ttgctgacgg gcatgaatca agtttattgg aaaagattat acagcaagtc   540
ctacaagttg tcaaccagac acctctagat gttgcttggc acccagttgg agtagattct   600
tctgtcaaag atataagagtt attattgcaa aatgaatgtg aagatgaagt tcgaatgatt   660
ggtattcacg gagttggtgg catagggaaa acaactctgg caaaagctat gtacaatcga   720
atgtttcgac tcttccatag tagttgcttc ctttcagatg ttagatcaga agctgaagaa   780
tttggtcttg tcaagctaca agagaaactt cttcaacaag tactcaaaac taaggacatc   840
aaagttggca gtgttgctca aggcatcaat ctaatcaaag caagactggg gtcaaagaag   900
gttctgattg ttcttgatga tgtggaccat aaaaagacagt tagaagcctt aacaagagaa   960
agaggttggt ttggttcggg tagttttaata atcattacca cccgagacga gcaattgcta   1020
tgtcggcttg gagaaaaaga gagatatgag gctgaactat taaatgacaa tgaagctcaa   1080
caacttttca gttgtcatgc ttttgacagt cctctccac cactagaata tgttagtttg    1140
gcacatgacg taatcgaata ttcaggtagg ctaccattag ctcttgtgac attggcgtca   1200
catttgcaag gaagttttgt agaagaatgg ggatatgaat tcgaaaaact aagagcaata   1260
cctacatattg atatccaaaa gattctcaag ataagcttta atggacttga tggtgataca   1320
caaactgtgt tccttgatat tgcgtgcgcc ttccatgggt tttatgagca tgaagttaca   1380
gaaatattaa atgcatgtgg ctttcatgct aaaagtgcaa ttgcaacttt agtccgaaaa   1440
cacttgctcc aaggatctcc gtgtcgtttg aagatgcatg atctagtgcg agatatggga   1500
agagaaattg ttcgcatgga atcagctcga gaacctgaca aacggagtag attgttcatc   1560
cctcaagaag ttcgtaatgt tctacaagga aatgaaggtt ccgaaaatgt agaagtactg   1620
aagtagatc gagggacatt aaacggagtg aacttgagca ccaaagcatt tgagcgaatg   1680
aagaatctta gggtgcttat aatcaatgac gagttatata ttagtggaga ttttgggatg   1740
ttgtccaata agcttagatg gttgtcttgg aaagaatgtc ctttaaaatg tataccatca   1800
aattttcccg ctgagaatct tgtagttcta gatatgcgaa agagtgatat cgaggaatttt   1860
caattgaatt tgcagatatg tttagaaaaa tggttagtct gtctctttct ctctctctct   1920
gctatcatat taatgatctt gagtctctgt ctgatgcagt gtgaaataga aatttatctc   1980
gaatgccaag agattctaga atggtgcagg aatcaagtaa caacttcatc tatgtgtttg   2040
actatgccga cacataataa ggagtataac ttcttaggaa tggttctctg gcttgtttc    2100
gacttctctt tggatgtagc ctctcttcca tgcttgtgga ttagtattgc ccataaacag   2160
ccttcactta tggggtggcg tggtgttctt acaacacttg aagtatcatg tgtaagttac   2220
atatcttact tacatagagc ttttgatggc cagatgatca aaggtgggga aaggatagaa   2280
gtgtggtctg agcacattac aataaagaag atagggatcc atctgttata tttggacgaa   2340
tatggtaaag ttatatcttt gccgggagac gtggatcatt cttattctaa gtacccaaaa   2400
agagtttcaa caggcttatt atcaactcct ccttataaaa gagcaaagtt ctga         2454

SEQ ID NO: 7           moltype = AA  length = 817
FEATURE                Location/Qualifiers
source                 1..817
                       mol_type = protein
                       organism = Nicotiana alata
SEQUENCE: 7
MDTQLVRVES STSSHFSYEV FLSFRGEDIR KTFTGHLYSK LDNVGVKTFI DDEELRKGDV   60
ISSKLEKAIE ESRISIIVFS RNYASSSWCL NELVKILECK EKLKHMVFPI FYDVDPSEVR   120
```

| | | | | | |
|---|---|---|---|---|---|
| KQTGLFGEAL | AKHKERPFGA | QMVEKWRAAL | TEAANFSGWD | LQNVADGHES | KFIEKIIQQV | 180
| LQVVNQTPLD | VAWHPVGVDS | SVKDIELLLQ | NECEDEVRMI | GIHGVGGIGK | TTLAKAMYNR | 240
| MFRLFHSSCF | LSDVRSEAEE | FGLVKLQEKL | LQQVLKTKDI | KVGSVAQGIN | LIKARLGSKK | 300
| VLIVLDDVDH | KRQLEALTRE | RGWFGSGSLI | IITTRDEQLL | CRLGEKERYE | AELLNDNEAQ | 360
| QLFSCHAFDS | PSPPLEYVSL | AHDVIEYSGR | LPLALVTLAS | HLQGSFVEEW | GYEFEKLRAI | 420
| PHIDIQKILK | ISFDGLDGDT | QTVFLDIACA | FHGFYEHEVT | EILNACGFHA | KSAIATLVRK | 480
| HLLQGSPCRL | KMHDLVRDMG | REIVRMESAR | EPGKRSRLFI | PQEVRNVLQG | NEGSENVEVL | 540
| KVDRGTLNGV | NLSTKAFERM | KNLRVLIIND | ELYISGDFGM | LSNKLRWLSW | KECPLKCIPS | 600
| NFPAENLVVL | DMRKSDIEEF | QLNLQICLEK | WLVCLFLSLS | AIILMILSLC | LMQCEIEIYL | 660
| ECQEILEWCR | NQVTTSSMCL | TMPTHNKEYN | FLGMVLWLVF | DFSLDVASLP | CLWISIAHKQ | 720
| PSLMGWRGVL | TTLEVSCVSY | ISYLHRAFDG | QMIKGGERIE | VWSEHITIKK | IGIHLLYLDE | 780
| YGKVISLPGD | VDHSYSKYPK | RVSTGLLSTP | PYKRAKF | | | 817

```
SEQ ID NO: 8            moltype = DNA   length = 6643
FEATURE                 Location/Qualifiers
source                  1..6643
                        mol_type = other DNA
                        organism = synthetic construct
SEQUENCE: 8
agccaaacac caattctttc cctttacttt ccatttttaaa tttcatgttt gtaaaaatat     60
atcacataaa ttgagacaga tgaaataaat gaattttgac caattttttc aattcacttg    120
ccgataatac aaaagggatt aaaaaaaaaa gactttgag atgcaaaaga aaagaatccc    180
gcaaacaact tgtagagtat ttctacccaa tacgaaaaag ggaaattacc agctatgtcc    240
atttagaagt atcccattac aaaaattggc caattaataa aatattacta atattagcca    300
aaatggccaa ttaactattt gtagcaaaaa aatatcaaat ttttactttc ttttgagtgg    360
gtgctattag aatagattgg gtatatctta aggagcttga atctcagttt tgggatgatt    420
tggtgaagtt ttgacgtggt ttaaattgaa aattcgaagt aaaaactgaa tatgaaaaaa    480
aatgatacat gtattacact gtgtatcaca tatgtatcat atttgtatcg attgtgtatc    540
acatgtatat ctgtgtgtga gatacatgtg tgatacatgt ttgatacatg tgtcacagaa    600
gaatttttg acatcgattt aattatgaat tttgatataa aaccagtcca aatcacctcc    660
aatcttcatc aaattttgta tattgactta tctatatgtt ttcaatgaat ttcgactata    720
cccattaaaa aaattcctg tttatttcga ttttggaata ttggctagag ttggtaagt    780
tgaaacttat atgggacatt tttgtaagtt tccctacgaa aaaatccaaa agtaatttcc    840
tagaacaact tacaaactgt gaactatact gcatgcattt atacttcctt ttcagtaact    900
cttgtttaat cttattcgat taaatttatg aatattattt cagtttgtaa tggcctaata    960
ttttaaaagg aatttgcaaa attcttattt catcactata caagaaaata cactcaaggg   1020
tcatatagga tctgtgaatt cagaggtgga tccgggattt gatggttatg agtgtcatcg   1080
cttttaatgc attttgtcag tttgatccat tttgaattaa tttggttcga tctattttaa   1140
ttttgtagat ttacaatatg agttacagcg tgaacttat ttacactata agactaagag   1200
cccgtttggc ttagctgatt tagagtagct gataagcatt aggtactgaa agcacttttt   1260
aagtgctgaa actgatttaa aaaataagca gttacgtgtt tggataaaag tgctgaaatt   1320
aataatatgc agctgaagaa ctgggtatac gaagagtttt gttttaaaaa gaagtatttt   1380
agggatagaa tagtaaatat tttggtcaaa cttaaagtgc ttataagctg aaaatttgta   1440
agttggggga gaccaactta tgactttgg cttattttg gcttataagc acttaactta   1500
taagcatttt taattttacc aaacgcgtag ataagccaaa aagtgcttat aagtcagttt   1560
gaccagctta taagcttagc caaacaccct ctaagagtct gtttggaaaa ggtgtaatta   1620
ttttaagtga tttttaaaat tatcattgcc aaaaactaat tacgaaaaaa gtacaacaaa   1680
aaaaaaaaag agtataggaa aaggtgaaat tatggcgaaa gtggaaatcc acaaaatttc   1740
atggcattcc gtttaatttc ttttaagggt tgacttgact tccacaaagg aagacctctg   1800
cttatatgta gctctgctac ttttcccttta ctgaaaaatt cattccttaa ttcttggatt   1860
ctcatcaacc cttaaatgga tactcaatta gttagagaga aatcatctac atcttctcac   1920
ttctctctatg aagtattcct cagttttaga ggtgaagaca cccgaaaaac attcactgct   1980
catcttttt ccaaattgtc tgatgttgga gttaatacct tcattgacga tgaggaattg   2040
agaaagggtg acgtgatttc aagagaatta gagaaagcaa ttgaagagtc tagaatttcc   2100
attattgttt tctcaagaaa ttatgcttcc tctagttggt gtctaaatga actagttaag   2160
attcttgaat gcaaagagaa atttaagcag atggttttgc ctattttcta tgatgttgat   2220
ccttctgagg tacgaaaaca aactgggtta tttggtgaag cttggctaa acacaaggaa   2280
cgaccatttg gagctcaaag ggtggagaaa tggagagctg cacttactga agctgcaaat   2340
ctatctggat gggatttgca aaatgtggac gggtacattt tcttgattca actatagaat   2400
ttcatttgtt atttgttcaa ttgttttata ggatgtgata ctaacggtta aaaaagagtt   2460
taggttttat acattgatat tattgaaata tatttaaaat ttattggaat taaatccgta   2520
aaataatttg gattatattt taaattcaag atatatccgt tcaaataaat ttgtatatgt   2580
taaattattt cttaaaatat cctatatgac gtcgtaagtt atctatttg tcgcttagat   2640
tcatcccact ttgttatgtc ttgctatcga ttttgatttc tccgtcaaat aatttcaaat   2700
atcaaagttt tatttactgg agtagtgttt cttttaattt tttgattttg ctaaaaaatt   2760
tgtaggcatg aatcaaagtt tattgaaaaa ataatacagc aagtcctaca agtggtcaac   2820
cagacacctc tagatgttgc ttggcaccca gttgagtag attctcgtgt caaagatata   2880
gagttattat tgcaaaatga atgtgaagat gaagttcgaa tgattggtat tcacggagtt   2940
ggtggcatag ggaaaacaac tctagcaaaa gctatctaca atcgaatgtt tcgactcttc   3000
gatagtagtt gcttcctttc agatgttaga tcagaagctg aagaatttgg tcttgtcaag   3060
ctacaagaga aacttcttcg acaaattctc aaaactgagg catcaaagt tggcagtgtt   3120
gctcaaggca tcaatctaat caaagcaaga ctcgggtcaa agaggttct aattgttctt   3180
gatgacgtgg accacagaaa ccaattgaaa tccttaacaa gagaaagaag ttggtttggt   3240
tcgggtggtt taataatcac taccacccga gacaagcagt tgctatgcgg gtttgggaaa   3300
aaagagagat atgaggccaa actattaat gacaatgaag ctatgttact tttttgttgg   3360
catgctttg ataggtcattt tccaccagaa gattatgtta atttggcacg agacataatc   3420
agatattcag gtaggctacc attagctctt gtgacattgg ggttacattt acaaggaagt   3480
tctatagaag aatggggata tgaattcgaa aaactaaaat caattcctca ttgtgatatc   3540
caaaagattc tcaagataag cttttgatgga cttgatgatg aaacacagac tgttttcctc   3600
```

```
gatattgcat gcatcttcca tgggtttgat gagcgtaaag ttaataaaat attaaatgca   3660
tgtggctttc atgctaaaag tgcaattaca actttagtcc aaaaacactt gctccaaaga   3720
tcttgggatt atttggtgat gcatgatcta gtgcgagata tgggaagata tattgttcgc   3780
atggaatcag ctcgagaccc tggaaaacgg agtagattgt tcatccctca agaagtctgt   3840
gatgttctac aaggaaataa agttagtaaa tcttttatcc tttatcttgg ttataatata   3900
tttttcaatt taattgttta ttgcttataa tgttgtcatc ataatatata agtgaattca   3960
ttttgtgctt cgtctatggt tagttttgta gttttttgtc aaccattgta aactagaagt   4020
tacatttgct aaattcttaa ctcacaccca aggcggaaaa aaatcaccta tttaacaatt   4080
atcctaattt ggtgatgcat atttcttata aaattcttat aactaacatg ctaatgggca   4140
tccaccatag tatctccatg attagttatt caaagatatt tgactttact taactaaatg   4200
cagaaattaa gcttgctcga agaaatcagg catgtgaacg tttggaaatt gttgaatccg   4260
tacatatgtg aaacattatt tctagaacaa tatgtacaaa gtattctttc aaatatattc   4320
aaatatatct tctatcttct agtgctatta tcatggttcc cattcacaca gtatcaatat   4380
gttctcttta ttcatttttt tcccttttgat attatcatgt gaacttagtg aatgctgcta   4440
gccgggtttg aaaggctctc atcttagctt tttgaacaat tttaaatttg tttaacatcc   4500
tctaatgtgt aagttcattt ttgttgatac atggtgtatt ctctttgttt gtccaccaat   4560
ttgtataaag cattttttctc gcgtaatttc tgatatttaa catgtgctta agttactttt   4620
tttttactg agctgcaggg ttccaaaaat gtagaagtac tgaaggtaga tccagggaca   4680
ttaaagggag tgaacttgag caccaaagca tttgagaaaa tgaagaatct tagggtgctc   4740
ataatcgagg agttacatat tagtggagat tttgggctgt tgtccaagaa gctcaaatgg   4800
ttgtcttggc aaaactgtcc tttaaaatat ataccatcaa attttccagc tgagaatctt   4860
gtagttctag atatgcggaa gagtgtatc gaggaatttc agttaattt gcaggtttgt   4920
tactcaatttt tacaatttca tgtgtactgt tattgccact gagtgaaaga aaatgttaat   4980
tgaaactata tttggtttac ttttagtgtt gtagaagttt gaagaagctg aatctctcta   5040
attgcaagca actcagaagc actccaaact tcaatggttc actgagtctt gagattttga   5100
atctcgatgg ttgcctaagt ctgagggaga tccatccatc aataggaat ttgtccagac   5160
taattaaact atatatgcgt ggttgcgaaa aacttacgga tcttcctagc agcatttgcc   5220
agctaaaatc ccttgattac ttggacattg atggctgctc atttataaaa acactgccag   5280
ataaccttgg agatatgaaa agtctaagac atctttctgc atcttatacg ggtataaaac   5340
aattgcctag atctgttgaa atgctaagaa atcttaaaat atggaagtg ggaaatcgaa   5400
tgtttgggac caatatgagt atttatgaa gaggagtcca tcagatacaa tattccttgt   5460
caactttgt atccgatttg agacttacat actgtaattt gtccgaggct gatattccta   5520
gggatattgg gagctcatcc tccttagaac ttttagattt gagtggcaac agtttccatt   5580
gtctacctt tgatttttct aagttacgat tcttgaaggg gttgtatttg attgactgtg   5640
agaaccttca aacactcccg tcaatatcaa atttagagaa acttgaaaga attgaacttc   5700
aaaattgcca aaaattggtc aagattagag agttggacaa cctcccttct atatggtcga   5760
tcgacatgag gaattgtagt tgtctgcaga atccatcaa tgaaagcttc ttcagtgcac   5820
ctgctctatc atttccatct agattagtct ctctctctct ctcctcatc atattaatga   5880
tcttgagtct ttgtccgatg cagcatgaaa tagaaattag catttatctg gaatgcaaag   5940
agattccaga atggtgcagg aatcgagtaa caacttcatc tatgtgtttg actatgccta   6000
cacataataa ggagtataac ttcttaggaa tggttctctg gttagtttcc gacttctctc   6060
atccatgctt gtggattagt attgcccata aacagcctc aattatggtg tggagtagtg   6120
tttatacaac acttggtaca cttgatggac acacagaagt atcatgtgta gttacatat   6180
cttacttaca tagagctttt gatgccaga tgatcaaagg cggggaaacg atagaagcgt   6240
ggtctgaaga ctctacaata aagaagatag ggatccatct gttatatttg gacgaatatg   6300
gtaaagttat atctttgccg ggagacgtgg atcattctta ttctaagtac ccaaaaagag   6360
tttcaacagt cttatcaact cctccttata aagagcaaa gtctgagtc aagataattt   6420
tcctttagag ctaatcaaat tgtatttata ttacactatt aatgtgtagt tcatcagtta   6480
attttttaatt gatattgatc tttttcccaaa tatttgttat atatatatat tttttgtgtt   6540
atcaagtatt tatctgtctc ctagttccta tggactaaaa tgaaacaaa aactagataa   6600
attcaatctg ccatgtacgt aatctttttc ccttggccaa atc                    6643

SEQ ID NO: 9            moltype = DNA   length = 527
FEATURE                 Location/Qualifiers
source                  1..527
                        mol_type = other DNA
                        organism = synthetic construct
SEQUENCE: 9
tcctcaacct ccacgaacgt ggacccctta tcgcgaacgc atagaacaac caggcagggc    60
ccccagaccc cttctacgtg aacacgagga cacccacgcg aacgcgatga actggcaaat   120
ccaccccttc gtgatcgcgg acctactccc gcgaacgcga tgaccaattt ttggtctgca   180
ctgctgtgca ttttctgcag aaattctcaa gtccaaactt cccgttcaac catccgaaac   240
caccccgagg cccccgggac ctcaaccaaa agcacgaaca tgacctatta ccttattcaa   300
acttgctcgg gccattaaaa cgctatcgtt aacatcaaat tcctcaaaa                360
aaagcctaag tttcttaaaa ccttccgaat tgcacattcg atcaaaaacc cgacctaaac   420
atctccgaat gacctgcaac tttacacaca tatccaaaat cacttaacgg agctactgca   480
actctcgaaa tcccattccg accctcggat cagaatctcg cataccg                 527

SEQ ID NO: 10           moltype = DNA   length = 721
FEATURE                 Location/Qualifiers
source                  1..721
                        mol_type = other DNA
                        organism = synthetic construct
SEQUENCE: 10
agtcttctgc cgctccatct ccagcgcggc ctgagaacag ggccacggag gcctcagggg    60
tcgtccgccc cagagttgag ttggtgccaa gcgaagagga tgaggaggag gagaggccgc   120
tcgttagacg tagggtggat tttgacgtga cctcttcggc ggtgatcagc ttagattctc   180
cgccgacgga agcaggaggg gacacagcag aggcggctcc aaaaggggag cattcagtgg   240
gggttgcccc ggttggctca ggccatgtag ataccgtcgt tgcggcgact gaagatgtac   300
```

```
cacctgccgc tgatagggaa gttgggtcct cggcggcagc ggtgacggag gagacggccg   360
ctcaggccat tgttggtgtt aatgttgctg ctcacgcggc ggaggcatcg acttcacgag   420
gtgctaaagg ccacggtgcc ttacgtgaag gggaggattc ggactccgac ttggaccctg   480
aggacgtcca catgttccag gagggcctca ctcgccatga agtgcacgtg gagggggaatt  540
ctcgatatat cgagcttcct aatgacctga acctccttcc ccaggaggag aatttggtga   600
cgctcttcga agtgttgagc tcagcggcg  agagcacgtc cgtgcagggc attacggacg   660
tgggcctgat gggcgaggtt gccgcgaact gtataaaggt aatggcgaat acttgggtcg   720
a                                                                   721

SEQ ID NO: 11            moltype = DNA   length = 21
FEATURE                  Location/Qualifiers
source                   1..21
                         mol_type = other DNA
                         organism = synthetic construct
SEQUENCE: 11
cggtatgcga gattctgatc c                                             21

SEQ ID NO: 12            moltype = DNA   length = 19
FEATURE                  Location/Qualifiers
source                   1..19
                         mol_type = other DNA
                         organism = synthetic construct
SEQUENCE: 12
tcctcaacct ccacgaacg                                                19

SEQ ID NO: 13            moltype = DNA   length = 19
FEATURE                  Location/Qualifiers
source                   1..19
                         mol_type = other DNA
                         organism = synthetic construct
SEQUENCE: 13
agtcttctgc cgctccatc                                                19

SEQ ID NO: 14            moltype = DNA   length = 21
FEATURE                  Location/Qualifiers
source                   1..21
                         mol_type = other DNA
                         organism = synthetic construct
SEQUENCE: 14
tcgacccaag tattcgccat t                                             21

SEQ ID NO: 15            moltype = DNA   length = 46
FEATURE                  Location/Qualifiers
source                   1..46
                         mol_type = other DNA
                         organism = synthetic construct
SEQUENCE: 15
catttggaga ggacacgctc gagatggata ctcaattagt tagagg                  46

SEQ ID NO: 16            moltype = DNA   length = 49
FEATURE                  Location/Qualifiers
source                   1..49
                         mol_type = other DNA
                         organism = synthetic construct
SEQUENCE: 16
tctcattaaa gcaggactct agagatttgg ccaagggaaa aagattacg               49

SEQ ID NO: 17            moltype = DNA   length = 48
FEATURE                  Location/Qualifiers
source                   1..48
                         mol_type = other DNA
                         organism = synthetic construct
SEQUENCE: 17
catttggaga ggacacgctc gagatggata ctcaattagt tagagtag                48

SEQ ID NO: 18            moltype = DNA   length = 46
FEATURE                  Location/Qualifiers
source                   1..46
                         mol_type = other DNA
                         organism = synthetic construct
SEQUENCE: 18
tctcattaaa gcaggactct agagttagga ttggttgggt ggacta                  46

SEQ ID NO: 19            moltype = DNA   length = 20
FEATURE                  Location/Qualifiers
source                   1..20
                         mol_type = other DNA
                         organism = synthetic construct
SEQUENCE: 19
```
ctatgatgtt gatccttctg                                             20

SEQ ID NO: 20           moltype = DNA   length = 24
FEATURE                 Location/Qualifiers
source                  1..24
                        mol_type = other DNA
                        organism = synthetic construct
SEQUENCE: 20
ggcactatga tgttgatcct tctg                                        24

SEQ ID NO: 21           moltype = DNA   length = 24
FEATURE                 Location/Qualifiers
source                  1..24
                        mol_type = other DNA
                        organism = synthetic construct
SEQUENCE: 21
cagaaggatc aacatcatag caaa                                        24

SEQ ID NO: 22           moltype = DNA   length = 22
FEATURE                 Location/Qualifiers
source                  1..22
                        mol_type = other DNA
                        organism = synthetic construct
SEQUENCE: 22
aggtgaaatt atggcgaaag tg                                          22

SEQ ID NO: 23           moltype = DNA   length = 21
FEATURE                 Location/Qualifiers
source                  1..21
                        mol_type = other DNA
                        organism = synthetic construct
SEQUENCE: 23
cttcagtaag tgcagctctc c                                           21

SEQ ID NO: 24           moltype = DNA   length = 25
FEATURE                 Location/Qualifiers
source                  1..25
                        mol_type = other DNA
                        organism = synthetic construct
SEQUENCE: 24
ctggtcatct ttattccaaa ttaga                                       25

SEQ ID NO: 25           moltype = DNA   length = 26
FEATURE                 Location/Qualifiers
source                  1..26
                        mol_type = other DNA
                        organism = synthetic construct
SEQUENCE: 25
ttgaatcaag aatatgtacc cgtcag                                      26

SEQ ID NO: 26           moltype = DNA   length = 50
FEATURE                 Location/Qualifiers
source                  1..50
                        mol_type = other DNA
                        organism = synthetic construct
SEQUENCE: 26
tgcatccaac gcgttgggag ctcagccaaa caccaattct ttcccttac             50

SEQ ID NO: 27           moltype = DNA   length = 60
FEATURE                 Location/Qualifiers
source                  1..60
                        mol_type = other DNA
                        organism = synthetic construct
SEQUENCE: 27
agaaatttaa gcagatggtt ttgcctattt tctatgatgt tgatccttct gaggtacgaa  60

SEQ ID NO: 28           moltype = DNA   length = 60
FEATURE                 Location/Qualifiers
source                  1..60
                        mol_type = other DNA
                        organism = synthetic construct
SEQUENCE: 28
agaaattaaa gcatatggtt tttcctattt tctatgatgt tgatccttct gaggtacgaa  60

SEQ ID NO: 29           moltype = DNA   length = 20
FEATURE                 Location/Qualifiers
source                  1..20
                        mol_type = other DNA
                        organism = synthetic construct

```
SEQUENCE: 29
ctatgatgtt gatccttctg                                                 20

SEQ ID NO: 30          moltype = DNA   length = 19
FEATURE                Location/Qualifiers
source                 1..19
                       mol_type = other DNA
                       organism = synthetic construct
SEQUENCE: 30
ctatgatgtt gatcctttg                                                  19

SEQ ID NO: 31          moltype = DNA   length = 19
FEATURE                Location/Qualifiers
source                 1..19
                       mol_type = other DNA
                       organism = synthetic construct
SEQUENCE: 31
ctatgatgtt gatcctctg                                                  19

SEQ ID NO: 32          moltype = DNA   length = 18
FEATURE                Location/Qualifiers
source                 1..18
                       mol_type = other DNA
                       organism = synthetic construct
SEQUENCE: 32
ctatgatgtt gatccttg                                                   18

SEQ ID NO: 33          moltype = DNA   length = 17
FEATURE                Location/Qualifiers
source                 1..17
                       mol_type = other DNA
                       organism = synthetic construct
SEQUENCE: 33
ctatgatgtt gatcctg                                                    17

SEQ ID NO: 34          moltype = DNA   length = 16
FEATURE                Location/Qualifiers
source                 1..16
                       mol_type = other DNA
                       organism = synthetic construct
SEQUENCE: 34
ctatgatgtt gatctg                                                     16

SEQ ID NO: 35          moltype = DNA   length = 14
FEATURE                Location/Qualifiers
source                 1..14
                       mol_type = other DNA
                       organism = synthetic construct
SEQUENCE: 35
ctatgatgtt gatg                                                       14

SEQ ID NO: 36          moltype = DNA   length = 21
FEATURE                Location/Qualifiers
source                 1..21
                       mol_type = other DNA
                       organism = synthetic construct
SEQUENCE: 36
ctatgatgtt gatccttact g                                               21

SEQ ID NO: 37          moltype = DNA   length = 21
FEATURE                Location/Qualifiers
source                 1..21
                       mol_type = other DNA
                       organism = synthetic construct
SEQUENCE: 37
ctatgatgtt gatcctttct g                                               21

SEQ ID NO: 38          moltype = DNA   length = 21
FEATURE                Location/Qualifiers
source                 1..21
                       mol_type = other DNA
                       organism = synthetic construct
SEQUENCE: 38
ctatgatgtt gatccttgct g                                               21
```

SPOTTED WILT DISEASE RESISTANCE GENE RTSW FROM TOBACCO AND USE THEREOF

CROSS REFERENCE TO THE RELATED APPLICATIONS

This patent application is a U.S. national stage filing under 35 U.S.C. § 371 of PCT International Application No. PCT/CN2022/124977 filed Oct. 12, 2022. The disclosure of the application identified in this paragraph is incorporated herein by reference in its entirety.

SEQUENCE LISTING

The instant application contains a Sequence Listing which has been submitted in XML format via EFS-Web and is hereby incorporated by reference in its entirety. Said XML copy is named 000040usnp_SequenceListing.xml, created on Mar. 31, 2025, and is 61,343 bytes in size.

FIELD OF THE INVENTION

The present invention relates to gene isolation and plant improvement, particularly to spotted wilt disease resistance gene RTSW from tobacco and use thereof.

BACKGROUND OF THE INVENTION

Orthotospoviruses belong to the order Bunyavirales and family Tospoviridae, which have become a huge threat to agricultural production due to their wide host range (infecting more than 1090 plants of 84 families) and huge economic losses they have caused. Orthotospoviruses are recognized as one of the most destructive viruses in plant viruses, ranking second among the most important plant viruses worldwide. Tobacco spotted wilt disease (TSWD) is a severe disease caused by orthotospoviruses infection. TSWD causes dwarfing of tobacco plants, wrinkled leaves, and small necrotic rings densely distributing on leaves. These rings often merge into large spots to form irregular necrotic areas. The disease expands rapidly from the onset site to the top of the tobacco plant. Apical buds of the plant wilt and droop, eventually leading to necrosis of the entire plant and complete loss of economic value. It has been reported that a variety of orthotospoviruses, mainly including tomato spotted wilt virus (TSWV) (American type) and tomato zonate spot virus (TZSV) (Eurasian type) etc., can infect tobacco and cause TSWD. There are currently no flue-cured tobacco varieties resistant to TSWD in cultivated tobacco (*Nicotiana tabacum* L.). Breeding varieties with a broad-spectrum resistance to orthotospoviruses is the most economical and effective means of prevention and control, which can fundamentally meet the needs of agricultural green prevention and control.

Disease resistance gene resources in tomatoes and peppers have been reported, which are Sw-5b and Tsw genes respectively. They are both disease resistance genes of CC-NBS-LRR structural type. Sw-5b has resistance to multiple orthotospoviruses of American type, but has no resistance to orthotospoviruses of Eurasian type that are very devastating. Tsw only has resistance to TSWV. In addition to these two genes, there are no other reports about orthotospoviruses resistance genes or loci in other crops. Disease resistance breakthrough virus strains for Sw-5b and Tsw have been reported in many countries, thus new disease resistance gene resources are urgently needed.

Previous studies have shown that *Nicotiana alata* has good resistance to TSWV. *N. alata* inoculated with TSWV only showed slight symptoms of hypersensitive necrosis on the inoculated leaves, and no virus was detected in the systemic leaves after inoculation. Using *N. otophora* as a bridge parent, Gajos et al. successfully transferred the TSWV resistance locus (named RTSW locus, where RTSW is the abbreviation of Resistance to TSWV) from *N. alata* to cultivated tobacco, and produced a breeding variant 'Polalta' comprising a long RTSW introgressed segment. (Laskowska D, Berbeć A, 2010. TSWV resistance in DH lines of tobacco (*Nicotiana tabacum* L.) obtained from a hybrid between 'Polalta' and 'Wiślica'. Plant Breeding 129, 731-3.)

Many genes unfavorable to cultivar's agronomic traits often exist in wild relatives. If they are closely linked to the target gene to be transferred, linkage drag will occur, increasing the difficulty of using excellent genes. Spotted wilt disease resistant tobacco 'Polalta' and other cultivated tobacco plants comprising a long RTSW introgressed segment all show relatively severe linkage drag. Genetic relationship assay indicates that the linkage drag is derived from the deleterious gene components closely linked or co-segregated with the RTSW locus on the long RTSW introgressed segment. The inventor's team has obtained tobacco plants resistant to spotted wilt disease without linkage drag by genetic locus analysis, molecular marker-assisted selection and large-scale screening. See, the international patent application no. PCT/CN2021/129382, entitled "Tobacco Plant Resistant to Spotted Wilt Disease Without Linkage Drag and Method for Breeding Same", and the Chinese patent application no. 202111311707.0, entitled "Molecular Markers for Screening Tobacco Plants Resistant to Spotted Wilt Disease Without Linkage Drag and Application Thereof". The entire content of the patent applications are incorporated herein by reference.

So far, the RTSW gene conferring tobacco TSWV resistance has not been cloned, limiting the research on disease resistance mechanism and breeding utilization of RTSW gene. In addition to tobacco, the breeding of other crop resistant to spotted wilt disease also has the limitation on available resistance gene resources. Therefore, the cloning and utilization of RTSW gene will also be conducive to controlling spotted wilt disease of other crops.

SUMMARY OF THE INVENTION

The present invention relates to the isolation of a plant resistance gene, particularly to the isolation of an RTSW gene that confers resistance to at least one orthotospovirus to plants (especially solanaceous plants). The RTSW gene is derived from *N. alata* and isolated/cloned from tobacco plants resistant to spotted wilt disease without linkage drag created by the inventors in earlier stage. The nucleotide sequences of the RTSW gene include, but are not limited to, nucleotide sequences of wild-type RTSW genes comprising a natural promoter and the 3' adjacent region comprising the coding region, cDNA sequences, and nucleotide sequences comprising only the coding region. Examples of nucleotide sequences of the RTSW gene include the nucleotide sequences set forth in SEQ ID NO: 1 and SEQ ID NO: 2 and variants thereof. The RTSW gene encodes RTSW protein. The RTSW protein can confer resistance to at least one orthotospovirus to plants (especially solanaceous plants) comprising the RTSW protein. Examples of amino acid sequences of the RTSW protein include the amino acid sequence set forth in SEQ ID NO: 3 and variants thereof.

Experiments proved that the RTSW gene cloned in the present invention has resistance not only to multiple orthotospoviruses of American type, but also to orthotospoviruses of Eurasian type that is very devastating. The results of transgenic experiments showed that the expression of RTSW gene alone in *N. benthamiana*, tomato and potato could confer resistance to orthotospoviruses to plants. Thus RTSW is a valuable disease resistance gene resource that can be used.

The present invention provides nucleic acid molecules comprising the nucleotide sequences of the RTSW gene or variants thereof, wherein the variants are naturally occurring or non-naturally occurring variants. In some embodiments, a nucleic acid molecule of the present invention comprises a nucleotide sequence selected from the following (a1)-(a5):
- (a1) the nucleotide sequence set forth in SEQ ID NO: 1;
- (a2) the nucleotide sequence set forth in SEQ ID NO: 2;
- (a3) a nucleotide sequence having at least 90% sequence identity to at least one of the nucleotide sequences set forth in SEQ ID NO: 1 and 2, wherein the nucleic acid molecule is capable of conferring resistance to at least one orthotospovirus to a plant comprising the nucleic acid molecule;
- (a4) a nucleotide sequence encoding the amino acid sequence set forth in SEQ ID NO: 3;
- (a5) a nucleotide sequence encoding an amino acid sequence having at least 90% sequence identity to the amino acid sequence set forth in SEQ ID NO: 3, wherein the nucleic acid molecule is capable of conferring resistance to at least one orthotospovirus to a plant comprising the nucleic acid molecule.

The nucleic acid molecules of the present invention include polynucleotide derivatives or variants that are substantially similar in sequences and functions to natural polynucleotides (e.g., the polynucleotide set forth in SEQ ID NO: 1 or 2, or polynucleotides encoding the amino acid sequence set forth in SEQ ID NO: 3). The natural polynucleotides comprise naturally occurring nucleotide sequences. The polynucleotide derivatives or variants include: polynucleotides obtained by deleting and/or adding one or more nucleotides at the 5' end and/or 3' end of a natural polynucleotide, polynucleotides obtained by deleting and/or adding one or more nucleotides in one or more internal sites of a natural polynucleotide, polynucleotides obtained by replacing one or more nucleotides at one or more sites of a natural polynucleotide, and/or polynucleotides encoding one of the RTSW proteins of the present invention based on the degeneracy of genetic codes. The polynucleotide derivatives or variants include naturally occurring polynucleotides, such as naturally occurring allele variants that can be identified using well-known molecular biological techniques (e.g., polymerase chain reaction and hybridization), and synthetic polynucleotides, such as polynucleotides that are generated by site-directed mutagenesis and still encode the RTSW proteins of the present invention. In some embodiments of the present invention, the polynucleotide derivatives or variants have at least about 75%, 80%, 85%, 90%, 91%, 92%, 93%, 94%, 95%, 96%, 97%, 98%, 99% or higher sequence identity with the natural polynucleotides. The amino acid sequences encoded by the polynucleotide derivatives or variants have at least 90% sequence identity and the same disease resistance function with the amino acid sequence set forth in SEQ ID NO: 3.

The present invention relates to polynucleotide constructs comprising the nucleic acid molecules of the present invention together with operatively linked one or more regulatory elements for gene transcription and expression in prokaryotic or eukaryotic host cells. The polynucleotide constructs may be plasmids, cosmids, phage, or expression vectors, transformation vectors, shuttle vectors or cloning vectors. It can be double stranded or single stranded, linear or circular, and can transform prokaryotic or eukaryotic host cells by incorporating into the genome or existing outside the chromosomes.

The present invention provides an expression cassette comprising a nucleic acid molecule of the present invention and an operably linked promoter. The promoter can be a native promoter of the RTSW gene, such as the promoter having a nucleotide sequence set forth in SEQ ID NO: 4, or a heterologous promoter, such as a constitutively inducible promoter (e.g., a 35S promoter derived from the cauliflower mosaic virus known in the art), or a pathogen-inducible promoter (e.g., the PR 1 gene promoter).

The present invention provides a vector comprising a nucleic acid molecule or expression cassette of the present invention.

The nucleic acid molecules, expression cassettes or vectors of the present invention can be used to transform any plant, including but not limited to monocotyledonous plants and dicotyledonous plants. Preferably, the plants are solanaceous plants.

The present invention provides a host cell transformed with nucleic acid molecules, expression cassettes or vectors of the present invention. The host cell can be a prokaryotic cell (e.g. a bacterial cell) or a eukaryotic cell (e.g. a yeast cell or a plant cell). In some embodiments of the present invention, the host cell is *Agrobacterium* (e.g., *Agrobacterium tumefaciens* or *A. rhizogenes*) or a plant cell transformed with the nucleic acid molecules or vectors of the present invention. Methods for obtaining said host cell include, but are not limited to, methods of chemical drug induction, thermal transformation, gene gun transformation, *Agrobacterium* mediated transformation, protoplast transfection, transduction, vacuum infiltration or electroporation that are well known in the art. For example, the nucleic acid molecules, expression cassettes or vectors of the present invention are introduced into *Agrobacterium* by methods of chemical drug induction, thermal transformation or electroporation; The nucleic acid molecules, expression cassettes or vectors of the present invention are introduced into plant cells by methods of gene gun transformation, *Agrobacterium* mediated transformation, protoplast transfection, transduction or plant virus mediated gene introduction.

The present invention relates to transgenic plants or plant parts comprising transgenic plant cells transformed with nucleic acid molecules, expression cassettes or vectors of the present invention. The plant parts can be cells, tissues, organs, or a combination of several cells, tissues or organs, such as flowers, leaves, tubers, fruits, or seeds. The transgenic plants, particularly solanaceous plants, have higher resistance to multiple orthotospoviruses compared with non-transgenic plants.

The present invention provides a transgenic plant comprising stably incorporated in its genome a heterologous polynucleotide construct comprising a nucleotide sequence selected from the following (a1)-(a5):
- (a1) the nucleotide sequence set forth in SEQ ID NO: 1;
- (a2) the nucleotide sequence set forth in SEQ ID NO: 2;
- (a3) a nucleotide sequence having at least 90% sequence identity to at least one of the nucleotide sequences set forth in SEQ ID NO: 1 and 2, wherein the nucleic acid molecule is capable of conferring resistance to at least one orthotospovirus to a plant comprising the nucleic acid molecule;

(a4) a nucleotide sequence encoding the amino acid sequence set forth in SEQ ID NO: 3;
(a5) a nucleotide sequence encoding an amino acid sequence having at least 90% sequence identity to the amino acid sequence set forth in SEQ ID NO: 3, wherein the nucleic acid molecule is capable of conferring resistance to at least one orthotospovirus to a plant comprising the nucleic acid molecule.

In some embodiments of the present invention, the polynucleotide construct further comprises a promoter operably linked for the expression of the nucleotide sequence in a plant. A suitable promoter can be a native promoter of the RTSW gene, such as a promoter having the nucleotide sequence set forth in SEQ ID NO: 4.

In some embodiments of the present invention, the transgenic plant is a solanaceous plant. The solanaceous plant includes, but is not limited to, a cultivated solanaceous plant.

In some embodiments of the present invention, the solanaceous plant is tobacco, potato, or tomato.

In some embodiments of the present invention, the transgenic plant comprises resistance to at least one orthotospovirus, relative to a control plant. The control plant is an initial plant that is used to obtain the transgenic plant and does not contain the polynucleotide construct.

In some embodiments of the present invention, the transgenic plant comprises resistance to Tomato spotted wilt virus (TSWV), Impatiens necrotic spot virus (INSV), Groundnut ringspot virus (GRSV), Chrysanthemum stem necrosis virus (CSNV), Tomato zonate spot virus (TZSV), Groundnut bud necrosis virus (GBNV), Mulberry vein banding associated virus (MVBaV), Capsicum chlorosis virus (CaCV), and Calla lily chlorotic spot virus (CCSV), relative to a control plant.

The methods for obtaining the transgenic plant of the present invention include, but are not limited to, artificial de novo gene synthesis methods, transgenic technologies, protoplast regeneration, hybrid breeding methods, and genome editing methods including CRISPR/Cas9 technology, zinc finger nuclease (ZFN) technology, and transcription activator like effector nuclease (TALEN) technology, etc.

The present invention provides seeds from any of the transgenic plant, the seeds comprising the nucleic acid molecule of the present invention.

The present invention provides a method for conferring or enhancing resistance to at least one orthotospovirus to a plant, the method comprising introducing a heterologous polynucleotide construct into at least one plant cell, the polynucleotide construct comprising a nucleotide sequence selected from the following (a1)-(a5):

(a1) the nucleotide sequence set forth in SEQ ID NO: 1;

(a2) the nucleotide sequence set forth in SEQ ID NO: 2;

(a3) a nucleotide sequence having at least 90% sequence identity to at least one of the nucleotide sequences set forth in SEQ ID NO: 1 and 2, wherein the nucleic acid molecule is capable of conferring resistance to at least one orthotospovirus to a plant comprising the nucleic acid molecule;

(a4) a nucleotide sequence encoding the amino acid sequence set forth in SEQ ID NO: 3;

(a5) a nucleotide sequence encoding an amino acid sequence having at least 90% sequence identity to the amino acid sequence set forth in SEQ ID NO: 3, wherein the nucleic acid molecule is capable of conferring resistance to at least one orthotospovirus to a plant comprising the nucleic acid molecule.

In some embodiments of the present invention, the polynucleotide construct further comprises a promoter operably linked for the expression of the nucleotide sequence in a plant, and the polynucleotide construct is stably incorporated into the genome of the plant cell.

In some embodiments of the present invention, the plant cell is regenerated into a plant comprising in its genome the polynucleotide construct. Regeneration methods known in the art can be used.

In some embodiments of the present invention, the plant is tobacco, potato, or tomato.

In some embodiments of the present invention, the plant comprises resistance to at least one orthotospovirus, relative to a control plant.

In some embodiments of the present invention, the plant comprises resistance to Tomato spotted wilt virus (TSWV), Impatiens necrotic spot virus (INSV), Groundnut ringspot virus (GRSV), Chrysanthemum stem necrosis virus (CSNV), Tomato zonate spot virus (TZSV), Groundnut bud necrosis virus (GBNV), Mulberry vein banding associated virus (MVBaV), Capsicum chlorosis virus (CaCV), and Calla lily chlorotic spot virus (CCSV), relative to a control plant.

The present invention provides plants produced by the method of the present invention, or fruits, tubers, leaves, or seeds of the plants, wherein the fruits, tubers, leaves, or seeds comprise the polynucleotide construct.

The present invention provides a method for identifying a plant comprising conferred or enhanced resistance to at least one orthotospovirus, the method comprising detecting the presence of RTSW in the plant, or in at least one part or cell thereof.

In some embodiments of the present invention, the plant is tobacco, potato, or tomato.

In some embodiments of the present invention, the presence of RTSW is detected by detecting at least one marker within RTSW.

The present invention provides primers for detecting the RTSW gene and a kit comprising the primers. The nucleotide sequences of the primers are set forth in SEQ ID NO: 22 and 23. Methods for detecting the RTSW gene using said primers comprise: isolating nucleic acids from a plant to be tested or germplasm thereof, and performing PCR in isolated nucleic acids using said primers.

The present invention provides a polypeptide comprising an amino acid sequence selected from the following (B1)-(B4):

(B1) the amino acid sequence encoded by the nucleotide sequence set forth in SEQ ID NO: 1;

(B2) the amino acid sequence encoded by the nucleotide sequence set forth in SEQ ID NO: 2;

(B3) the amino acid sequence set forth in SEQ ID NO: 3;

(B4) an amino acid sequence having at least 90% sequence identity to the amino acid sequence set forth in SEQ ID NO: 3, wherein a polypeptide comprising the amino acid sequence is capable of conferring resistance to at least one orthotospovirus to a plant comprising the polypeptide.

The polypeptides of the present invention can be produced in various ways, including but not limited to de novo synthesis in vitro, prokaryotic expression, and eukaryotic expression.

The polypeptides of the present invention include polypeptide derivatives or variants that are substantially similar in sequences and functions to natural proteins (e.g., a protein having an amino acid sequence set forth in SEQ ID NO: 3). The natural proteins comprise naturally occurring amino acid sequences. The polypeptide derivatives or variants can be derived from genetic polymorphism or artificial operation. The polypeptide derivatives or variants can be produced by various methods known in the art, including amino acid substitutions, deletions, and insertions. For example, the polypeptide derivatives or variants are obtained by deleting one or more amino acids at the N-terminal and/or C-terminal of the natural proteins, or deleting and/or adding one or more amino acids at one or more internal sites of the natural proteins, or replacing one or more amino acids at one or more sites of the natural proteins. The polypeptide derivatives or variants have at least about 75%, 80%, 85%, 90%, 91%, 92%, 93%, 94%, 95%, 96%, 97%, 98%, 99% or higher amino acid sequence identity with the natural proteins. The polypeptide derivatives or variants can be different from the natural proteins due to the difference of only 1-15, 1-10 (e.g. 6-10), 5, 4, 3, 2 and even 1 amino acid residue. The polypeptide derivatives or variants have the same disease resistance function with the natural proteins.

The orthotospoviruses described herein include, but are not limited to, viruses of American type: Tomato spotted wilt virus (TSWV), Impatiens necrotic spot virus (INSV), Groundnut ringspot virus (GRSV), Chrysanthemum stem necrosis virus (CSNV); viruses of Eurasian type: Tomato zonate spot virus (TZSV), Calla lily chlorotic spot virus (CCSV), Tomato chlorotic spot virus (TCSV), Mulberry vein banding associated virus (MVBaV), Capsicum chlorosis virus (CaCV), Groundnut bud necrosis virus (GBNV), Tomato necrotic spot virus (TNSV), pepper chlorotic spot virus (PCSV), Tomato necrotic ringspot virus (TNRV), Polygonum ringspot virus (PolRSV) and Hippeastrum chlorotic ringspot virus (HCRV).

The solanaceous plants described herein are members of Solanaceae family, including domesticated and non-domesticated members. The solanaceous plants include, but are not limited to, *Nicotiana* spp., *Solanum lycopersicum, Solanum tuberosum, Solanum melongena, Petunia* spp., *Capsicum* spp., *Physalis* spp., woody *Solanum* plants (*Solanum dulcamara*), *Solanum scabrum, Solanum macrocarpon, Solanum demissum, Solanum stoloniferum, Solanum papita, Solanum bulbocastanum, Solanum edinense, Solanum schenckii, Solanum hjertingii, Solanum venture, Solanum mochiquense, Solanum chacoense*, and *Solanum pimpinellifolium*. Preferably, the solanaceous plants are cultivated solanaceous plants in agriculture, including but not limited to tobacco, potato, tomato, eggplant, pepper, and petunia. More preferably, the solanaceous plants are tobacco, potato, and tomato.

The tobacco described herein can be wild species or cultivars (*Nicotiana tabacum*. L). The wild species include, but are not limited to, *N. benthamiana, N. alata, N. glauca, N. gossei, N. kawakamii, N. knightiana, N. langsdorffi, N. otophora, N. sylvestris, N. tomentosa, N. tomentosiformis, N. undulate, N. x sanderae, N. rustica, N. suaveolens*, and *N. attenuate*. The cultivars include, but are not limited to, Burley type, Dark type, Flue-cured type, Maryland type, Oriental type, or Cigar. The cultivars of tobacco described in the present invention can be selected from a plurality of common tobacco varieties, including but not limited to K326, Yunyan87, Yunyan97, Yunyan85, Yunyan116, Yunyan121, NC89, Zhongyan100, Honghuadajinyuan, Cuibi No. 1, BU 64, CC 101, CC 200, CC 13, CC 27, CC 33, CC 35, CC 37, CC65, CC 67, CC 301, CC 400, CC 500, CC 600, CC 700, CC 800, CC 900, CC 1063, Coker 176, Coker 319, Coker 371Gold, Coker 48, CU 263, DF911, Galpao tobacco, GL 26H, GL 338, GL350, GL 395, GL 600, GL 737, GL 939, GL 973, GF 157, GF 318, RJR 901, HB 04P, K 149, K326, K 346, K 358, K394, K 399, K 730, NC 196, NC 37NF, NC 471, NC 55, NC 92, NC2326, NC95, NC 925, PVH 1118, PVH 1452, PVH 2110, PVH 2254, PVH 2275, VA116, VA119, KDH 959, KT200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309 or VA359.

Definition

Unless otherwise defined, all technical and scientific terms used herein have the same meaning as commonly understood by those of ordinary skill in the art to which the subject matter of this disclosure belongs. Although it is considered that the following terms can be well understood by those of ordinary skill in the art, the following definitions are proposed to make the subject of the present disclosure easy to understand.

The term "RTSW gene" refers to a gene that is derived from *N. alata* genome and confers resistance to spotted wilt disease to a plant.

The terms "RTSW locus" or "TSWV resistance locus" refers to a DNA segment that is derived from *N. alata* genome and contains the RTSW gene. The locus confers resistance to spotted wilt disease to a plant in either heterozygous or homozygous state.

The term "RTSW introgressed segment" refers to a DNA segment that is from *N. alata* genome and contains the RTSW gene. Generally, tobacco plants containing the "RTSW introgressed segment" have resistance to tobacco spotted wilt disease.

The term "short RTSW introgressed segment" refers to a DNA segment that lacks part or all of non-target gene components (linkage drag gene components) linked to the RTSW gene on the long RTSW introgressed segment, and retains complete function of the RTSW gene.

The term "introgress" refers to the transfer of a desired allele of a genetic locus from one genetic background to another genetic background.

The term "allele" usually refers to a pair of genes located at the same position on a pair of homologous chromosomes that control relative traits. Most traits are determined by two or more alleles. If the alleles are identical, the individual is a homozygote for the trait. If the alleles are different, the individual is a heterozygote for the trait. In heterozygote pairings, the dominant allele makes the trait of the recessive allele unable to be displayed. In the present invention, the RTSW locus is a dominant allele.

The term "genotype" refers to genetic composition of an individual (or a population) at one or more genetic loci associated with an observable and/or detectable and/or exhibited traits (phenotype). Genotypes are defined by one or more alleles at one or more known loci inherited by an individual from its parents. "Genotype" can refer to genetic composition at a single locus or multiple loci, or genetic composition of all genes in the genome. Genotypes can be characterized indirectly using markers and/or characterized directly by nucleic acid sequencing.

The term "line" usually refers to a group of plants that are not commercially used. A "line" usually shows very small overall differences in one or more target traits between individuals, although there may be some differences in other traits between the individuals.

The term "cell death hypersensitive reaction" or "HR" is a typical disease resistance response of rapid cell death that occurs after plant-pathogen incompatibility interaction, and is a disease resistance mechanism of plants, accompanied by programmed cell death. It is characterized by the burst of cellular reactive oxygen species, rapid response of related disease resistance marker genes, and local cell death.

The term "avirulence gene" or "avirulence gene NSm" means that according to the gene-to-gene hypothesis, for any host disease resistance gene, the pathogenic species has a corresponding avirulence gene. Only when a pathogen carrying an avirulence gene infects a host plant carrying a corresponding resistance gene, the plant will be induced to develop resistance, otherwise the plant will be infected and become diseased. The avirulence gene NSm is able to generate cell death hypersensitive reaction (HR) in host plants carrying the RTSW gene, which can be used to detect spotted wilt disease resistance of tobacco. Chinese patent no. ZL201710414755.X disclosed a method for identifying tobacco resistance using the tomato spotted wilt virus NSm gene.

The term "transgenic" refers to introgression of an artificially isolated and modified gene into an organism's genome. The expression of an introgressed gene results heritable modification of an organism's trait. This technique is called transgenic. The commonly used terms "genetic engineering", "gene engineering", and "genetic transformation" are synonyms for transgenic.

The term "plant" includes a plant at any stage of maturation or development, and any cell, tissue or organ (plant part) derived from any said plant. Plant parts include, but are not limited to, seeds, fruits, stems, tubers, roots, flowers, ovules, stamens, leaves, embryos, meristem region, calli, anther cultures, gametocytes, sporozoites, pollens, microspores, protoplasts, etc.

The terms "transgenic plant" and "transformed plant" are equivalent terms, which refer to the "plant" as described above, the plant comprising a heterologous nucleic acid molecule, heterologous polynucleotide or heterologous polynucleotide construct introduced by, for example, any stable transformation and transient transformation method disclosed elsewhere in this disclosure or otherwise known in the art. The "transgenic plant" and "transformed plant" also refer to, for example, a plant into which the heterologous nucleic acid molecule, heterologous polynucleotide or heterologous polynucleotide construct is first introduced, and any progeny plants thereof comprising the heterologous nucleic acid molecule, heterologous polynucleotide or heterologous polynucleotide construct.

The term "gene editing", "genome editing" or "genomic DNA Editing", generally refers to gene editing using CRISPR/Cas system. CRISPR/Cas is an adaptive immune system in bacteria and archaea that specifically degrades the DNA of invading phages or foreign plasmids, wherein CRISPR is short for "clustered and regularly interspaced short palindromic sequences", and Cas refers to proteins that bind to CRISPR RNA. In 2012, Jinek et al unraveled the mechanism of action of type II CRISPR/Cas9 system of *Streptococcus pyogenes*, and demonstrated that the Cas9 nuclease (herein specifically referred to Cas9 of *Streptococcus pyogenes*) can target and cleave a DNA double strand under the guidance of an artificial small RNA molecule (termed gRNA, i.e. the Guide RNA). Using Cas9/gRNA to target specific DNA sites requires two conditions: (1) a guide sequence (termed Spacer) of 20nt (nucleotides) at the 5' end of a gRNA complementarily matches the sequence (termed Protospacer) of a target DNA site; (2) A PAM (Protospacer-adjacentmotif) is necessary for the target site, and the most widely used PAM sequence of Cas9 of *Streptococcus pyogenes* is 5'-NGG-3'. In genome editing using CRISPR/Cas9, generally, a Cas9 containing a nuclear localization signal is expressed using a Pol II (type II RNA polymerase) promoter, a gRNA is expressed using a pol III (type III RNA polymerase) promoter, and the Cas9/gRNA complex recognizes a target DNA and cleaves the DNA double strand between the third and fourth deoxynucleotides in front of the PAM to form a DSB (double stranded DNA break).

The term "codon" or "genetic codon" refers to a triplet composed of every three nucleotides from the 5' end to the 3' end of messenger RNA molecule, starting from the starting codon AUG. The genetic codon determines each amino acid and the sequence of amino acids on the peptide chain, as well as the initiation, elongation, and termination of protein synthesis. Genetic codons are a set of rules used for protein synthesis, according to which DNA or RNA sequences are translated into amino acid sequences of proteins by codons of three nucleotides. Almost all organisms use the same genetic codons, known as the standard genetic code.

The term "intron" is an intervening sequence in a DNA of eukaryotic cells. In the process of transcription from DNA to RNA, introns in DNA will be transcribed into the precursor RNA, but the introns in RNA will be cut off before the RNA leaves the nucleus for translation. The portion of the gene that remains in the mature mRNA is termed an "exon". Eukaryotic genes contain exons and introns, which is one of the characteristics that distinguish them from prokaryotes.

DESCRIPTION OF THE FIGURES

FIG. 1 shows the RTSW gene localization, cloning, gene structure, and characteristics of its encoded protein. Part A: The candidate disease resistance gene is limited to the 0.8 Mb interval of chromosome 3 of *N. alata* from 59.2 Mb to 60 Mb by using susceptible plant 16 and resistant plant 12. Part B: Gene structures of two candidate genes, TNL1 and TNL2, comprising four exons and encode TIR-NBS-LRR proteins. TNL1 encodes a full-length TIR-NBS-LRR protein with a full length of 1089 aa. TNL2 encodes a truncated TIR-NBS-LRR protein with a full length of 817aa.

FIG. 2 shows the results of identification of TNL1 and TNL2 using NSm induced HR. Part A is a schematic of TNL expression cassette. 35S represents a 35S promoter from the cauliflower mosaic virus; TNLs represents any of the full-length of TNL1, full-length of TNL1 CDs, full-length of TNL2, and full-length of TNL2 CDs; NOS represents a Nos terminator for termination of transcription. Part B: The left panel (TNLs+TSWV_NSm) is the result of co-infiltrating leaves of susceptible tobacco K326 by EHA105-35S-TNLs and EHA105-35S-TSWV_NSm (denoted as 35S-TNL1, 35S-TNL1_CDs, 35S-TNL2, and 35S-TNL2_CDs in the figure), wherein co-infiltrating leaves by EHA105-35S-Sw-5b and EHA105-35S-TSWV_NSm (denoted as 35S-Sw5b) is used as a control; The right panel (TNLs+TZSV_NSm) is the result of co-infiltrating leaves of susceptible tobacco K326 by EHA105-35S-TNLs and EHA105-35S-TZSV_NSm (denoted as 35S-TNL1, 35S-TNL1_CDs, 35S-TNL2, and 35S-TNL2_CDs), wherein co-infiltrating leaves by EHA105-35S-Sw-5b and EHA105-35S-TZSV_NSm is used as a control (denoted as 35S-Sw5b); "35S-TNL1 only" indicates inoculating EHA105-35S-TNL1 alone as a negative control. Phenotypes were observed 3 days post infiltration: 35S-TNL1 or 35S-TNL1_CDs could induce HR by co-infiltrating with TSWV_NSm or TZSV_NSm, while 35S-TNL2 or 35S-TNL2_CDs was unable to induce HR by co-infiltrating with TSWV_NSm or TZSV_NSm. As a negative control, "35S-TNL1 only" was unable to induce HR, indicating that the HR phenotype resulted from the activation by co-infiltration of TNL1 and NSm. Another control, 35S-Sw5b, could induce HR by co-infiltrating with TSWV_NSm, but was unable to induce HR by co-infiltrating with TZSV_NSm, which was consistent with the reported result that Sw5b was resistant to the American type orthotospovirus but not to the Asian type orthotospovirus.

FIG. 4 shows the phenotype of proTNL1:TNL1 transgenic K326 tobacco after inoculation with some avirulence genes and viruses. Part A is a schematic of proTNL1:TNL1 expression cassette. proTNL1 represents a native promoter of the TNL1 gene, TNL1 represents the full length TNL1 gene, and NOS is a terminator. Part B: The detection result of HR induced by avirulence genes in a positive line (#1) of proTNL1:TNL1 T0 transgenic K326. Like the spotted wilt disease resistant plants comprising the RTSW locus, the NSm genes of TSWV, INSV, TZSV and CCSV could induce significant HR but the NSm genes of TNSV and PCSV was unable to induce HR in the proTNL1:TNL1 transgenic positive line. Co-infiltrating leaves by the Sw-5b gene of tomato and TSWV_NSm (denoted as Sw-5b+TSWV_NSm) was used as a positive control, and Co-infiltrating leaves by empty vectors (denoted as EV) was used as a negative control. Part C: two randomly selected positive lines (#1 and #2) of proTNL1:TNL1 transgenic K326 were inoculated with TSWV and TZSV, and photographed 21 days post inoculation. Non-transgenic K326 showed obvious viral symptoms of TSWV and TZSV, while the proTNL1:TNL1 transgenic lines were not infected by the viruses.

FIG. 5 shows the phenotype of proTNL1:TNL1 transgenic *N. benthamiana* inoculated with TSWV and TZSV. Two positive lines (#1 and #4) of proTNL1:TNL1 transgenic *N. benthamiana* and non-transgenic *N. benthamiana* (Nb) were inoculated with TSWV and TZSV, and photographed 21 days post inoculation. Non-transgenic *N. benthamiana* showed obvious viral symptoms of TSWV and TZSV, while the proTNL1:TNL1 transgenic *N. benthamiana* lines were not infected by the viruses and had no viral symptoms.

FIG. 6 shows the phenotype of proTNL1:TNL1 transgenic tomato inoculated with TSWV and TZSV. Two positive lines (#1 and #2) of proTNL1:TNL1 transgenic tomato and non-transgenic tomato (S1) were inoculated with TSWV and TZSV, and photographed 21 days post inoculation. Non-transgenic tomato showed obvious viral symptoms of TSWV and TZSV, while the two proTNL1:TNL1 transgenic tomato lines were not infected by the viruses and had no viral symptoms.

FIG. 7 shows the phenotype of proTNL1:TNL1 transgenic potatoes inoculated with TSWV and TZSV. Two positive lines (#1 and #2) of proTNL1:TNL1 transgenic potatoes and non-transgenic potatoes (St) were inoculated with TSWV and TZSV. The leaves were photographed 21 days post inoculation. Non-transgenic potatoes showed obvious viral symptoms of TSWV and TZSV, while the two proTNL1:TNL1 transgenic potato lines were not infected by the viruses and had no viral symptoms.

DESCRIPTION OF THE SEQUENCE LIST

The nucleotide and amino acid sequences listed in the accompanying sequence listing are shown using standard letter abbreviations for nucleotide bases, and three-letter code for amino acids. The nucleotide sequences follow a standard convention of beginning at the 5' end of the sequence and proceeding forward to the 3' end. Only one strand of each nucleotide sequence is shown, but the complementary strand of the displayed strand is understood to be included. The amino acid sequences follow the standard convention beginning at the amino terminus of the sequence and proceeding forward to the carboxy terminus.

SEQ ID NO: 1 sets forth the nucleotide sequence of the RTSW gene (TNL1). If desired, a stop codon (e.g. TGA, TAG, TAA) can be operably linked to the 3' end of a nucleic acid molecule comprising SEQ ID NO: 1.

SEQ ID NO: 2 sets forth the nucleotide sequence of the coding region of the RTSW cDNA (TNL1 cDNA). If desired, a stop codon (e.g., TGA, TAG, TAA) can be operably linked to the 3' end of a nucleic acid molecule comprising SEQ ID NO: 2.

SEQ ID NO: 3 sets forth the amino acid sequence of the RTSW protein (TNL1 protein) encoded by the RTSW gene (TNL1).

SEQ ID NO: 4 sets forth the nucleotide sequence of the native promoter of the RTSW gene (TNL1).

SEQ ID NO: 5 sets forth the nucleotide sequence of the TNL2 gene.

SEQ ID NO: 6 sets forth the nucleotide sequence of the coding region of the TNL2 cDNA.

SEQ ID NO: 7 sets forth the amino acid sequence of the TNL2 protein encoded by the TNL2 gene.

Figure 3:
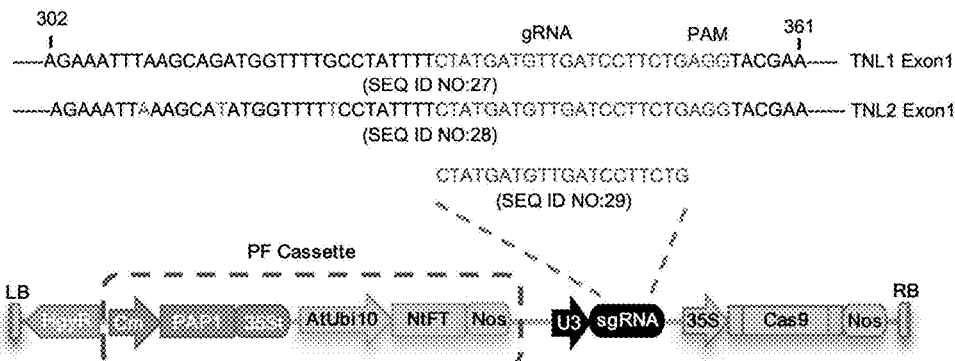
FIG. 3 shows gene editing of TNL1 and TNL2. Part A: Design of gRNA according to conserved sequences of TNL1 and TNL2 and introduction of the gRNA into the CRISPR/Cas9 vector, where AGAAATTTAAGCA-GATGGTTTTGCCTATTTTCTATGATGTTGATCCTTCT-GAGGTACG AA is set forth in SEQ ID NO:27, AGAAATTAAAGCATATGGTTTTTCCTATTTTCTAT-GATGTTGATCCTTCTGAGGTACG AA is set forth in SEQ ID NO:28, CTATGATGTTGATCCTTCTG is set forth in SEQ ID NO: 29. Part B: 21 independent editing events of TNL1 and TNL2 of T0 generation. The wild type without editing events is represented by "wt"; "i" indicates insertion of bases, and the number following "i" indicates the number of inserted bases; "d" indicates deletion of bases, and the number following "d" indicates the number of deleted bases; where CTATGATGTTGATCCTTCTG is set forth in SEQ ID NO:29, CTATGATGTTGATCCTT-TG is set forth in SEQ ID NO:30, CTATGATGTTGATCCT-CTG is set forth in SEQ ID NO:31, CTATGATGTTGATCCT--TG is set forth in SEQ ID NO:32, CTATGATGTTGATCC---TG is set forth in SEQ ID NO:33, CTATGATGTTGATC----TG is set forth in SEQ ID NO:34, CTATGATGTTGAT-----G is set forth in SEQ ID NO:35, CTATGATGTTGATCCTTaCTG is set forth in SEQ ID NO:36, CTATGATGTTGATCCTTtCTG is set forth in SEQ ID NO:37, CTATGATGTT-GATCCTTgCTG is set forth in SEQ ID NO:38. Part C: HR induction after infiltration using TSWV_NSm or TZSV_NSm in leaves of T0 plants in which TNL1 and/or TNL2 were edited. Plants with TNL1 edited alone (denoted as tnl1) and plants with TNL1/TNL2 edited simultaneously (denoted as tnl1/tnl2) failed to generate HR, while plants with TNL2 edited alone (denoted as tnl2) or plants with both TNL1 and TNL2 unedited (denoted as TNL1/TNL2) generated typical HR; The ratio at the bottom of the figure indicates the number of plants generating HR/total number of plants in each editing event.
Figure 3:
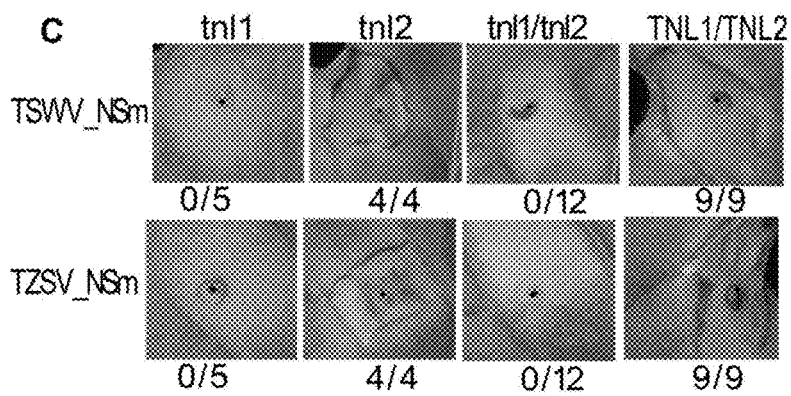

SEQ ID NO: 8 sets forth the nucleotide sequence of an expression cassette comprising the RTSW gene and its native promoter (proTNL1:TNL1).

SEQ ID NO: 9 sets forth the nucleotide sequence of NaChr3_59.2M marker.

SEQ ID NO: 10 sets forth the nucleotide sequence of NaChr3_59.7M marker.

SEQ ID NO: 11 sets forth the nucleotide sequence of primer NaChr3_59.2MF.

SEQ ID NO: 12 sets forth the nucleotide sequence of primer NaChr3_59.2MR.

SEQ ID NO: 13 sets forth the nucleotide sequence of primer NaChr3_59.7MF.

SEQ ID NO: 14 sets forth the nucleotide sequence of primer NaChr3_59.7MR.

SEQ ID NO: 15 sets forth the nucleotide sequence of primer TNL1_35SF.

SEQ ID NO: 16 sets forth the nucleotide sequence of primer TNL1_35SR.

SEQ ID NO: 17 sets forth the nucleotide sequence of primer TNL2_35SF.

SEQ ID NO: 18 sets forth the nucleotide sequence of primer TNL2_35SR.

SEQ ID No: 19 sets forth the nucleotide sequence of gRNA.

SEQ ID NO: 20 sets forth the nucleotide sequence of primer gRNA-F.

SEQ ID NO: 21 sets forth the nucleotide sequence of primer gRNA-R.

SEQ ID NO: 22 sets forth the nucleotide sequence of primer TNL1editTestF.

SEQ ID NO: 23 sets forth the nucleotide sequence of primer TNL1editTestR.

SEQ ID NO: 24 sets forth the nucleotide sequence of primer TNL2editTestF.

SEQ ID NO: 25 sets forth the nucleotide sequence of primer TNL2editTestR.

SEQ ID NO: 26 sets forth the nucleotide sequence of primer TNL1_NatProF.

DETAILED DESCRIPTION OF THE INVENTION

The invention will be further described in detail below by examples. Those skilled in the art will understand that the following examples are only used to illustrate the invention and should not be regarded as limiting the scope of the invention. For those examples in which specific technologies or conditions are not indicated, it shall be carried out in accordance with the technologies or conditions described in the literature in the art or in accordance with the product instructions. The reagents or instruments used without an indication of the manufacturer are all conventional products that can be obtained through purchase.

Tobacco materials used in the following Examples:

'Polalta' is a TSWV resistant tobacco material comprising the RTSW locus. The material is described in the non-patent literature "Laskowska D, Berbeć A, 2010. TSWV resistance in DH lines of tobacco (*Nicotiana tabacum* L.) obtained from a hybrid between 'Polalta' and 'Wiślica'. Plant Breeding 129, 731-3".

'K326' is a TSWV susceptible tobacco cultivar that does not comprise the RTSW locus. The cultivar is described in the non-patent literature "Edwards et al., 2017, A reference genome for *Nicotiana tabacum* enables map-based cloning of homologous loci implicated in nitrogen utilization efficiency. BMC Genomics 18,448". The public can obtain its reference genome sequence from the website of Sol Genomics.

*N. alata* is a kind of wild tobacco resistant to TSWV, which is described in a non-patent literature "Laskowska et al., 2013, A survey of *Nicotiana* germplasm for resistance to Tomato spotted wilt virus (TSWV). Euphytica 193, 207-19". *N. alata* has an accession number of PI42334 in the tobacco germplasm bank of the United States.

18 tobacco plants having a shortened RTSW introgressed segment and no linkage drag were obtained by the applicant in previous experiments by crossing 'Polata' as the male parent with 'K326' as the female parent, backcrossing the progeny with 'K326' as the recurrent parent for multiple generations, and screening by molecular marker detection and TSWV resistance test. The screening process is described in the international patent application no. PCT/CN2021/129382, entitled "Tobacco Plant Resistant to Spotted Wilt Disease Without Linkage Drag and Method for Breeding Same", and the Chinese patent application no. 202111311707.0, entitled "Molecular Markers for Screening Tobacco Plants Resistant to Spotted Wilt Disease Without Linkage Drag and Application Thereof". The entire content of the patent applications are incorporated herein by reference.

K326$^{RTSW}$ is a tobacco comprising the RTSW locus. It is a tobacco resistant to spotted wilt disease obtained by crossing 'Polata' as the male parent with 'K326' as the female parent.

The public can obtain the above tobacco materials from tobacco germplasm resources preservation organizations or Yunnan Academy of Tobacco Agricultural Sciences.

Viruses Used in the Following Examples:

Tomato spotted wilt virus (TSWV), Impatiens necrotic spot virus (INSV), Tomato zonate spot virus (TZSV), Calla lily chlorotic spot virus (CCSV), Capsicum chlorosis virus (CaCV), Tomato necrotic spot virus (TNSV), Pepper chlorotic spot virus (PCSV), and Hippeastrum chlorotic ringspot virus (HCRV). The sources of the viruses are preserved in Yunnan Academy of Tobacco Agricultural Sciences.

Vectors and Strains Used in the Following Examples:

The pCambia1300-NSm-YFP expression vectors containing NSm genes of orthotospoviruses were constructed by our laboratory and preserved in Yunnan Academy of Tobacco Agricultural Sciences. The NSm genes of 14 orthotospoviruses were as follows. American type: TSWV NSm gene (NCBI accession number: JF960236.1), CSNV NSm gene (NCBI accession number: AF213675), GRSV NSm gene (NCBI accession number: KY350137), and INSV NSm gene (NCBI accession number: NC_003616). Eurasian type: TZSV NSm gene (NCBI accession number: KM374588), CCSV NSm gene (NCBI accession number: KT004454), MVbaV NSm gene (NCBI accession number: NC_026618), CaCV NSm gene (NCBI accession number: NC_008303), GBNV NSm gene (NCBI accession number: KY006470), TNSV NSm gene (NCBI accession number: KT984753), PCSV NSm gene (NCBI accession number: KY315810), TNRV NSm gene (NCBI accession number: FJ947152), PolRSV NSm gene (NCBI accession number: EU271753), and HCRV NSm gene (NCBI accession number: KY363497). The NSm genes of the 14 viruses were respectively cloned into pCambia1300-YFP expression vectors to obtain pCambia1300-NSm-YFP recombinant plasmids. In the pCambia1300-NSm-YFP, the NSm gene is located downstream of a 35S promoter, in a complete reading frame with a YFP gene, allowing expression of NSm-YFP fusion proteins, wherein the YFP tag is used for detection of protein expression levels. The pCambia1300-NSm-YFP plasmids were introduced into *A. tumefaciens* EHA105, and a series of EHA105-pCambia1300-NSm-YFP strains were obtained.

pK2-35S-TSWV_NSm is a pK2GW7 plant expression vector carrying the TSWV NSm gene (NCBI accession number: JF960236.1). It is the pK2-35S-NSm vector disclosed in the Chinese patent no. ZL201710414755.X, entitled "A Method for Identification of Tobacco Resistance Using the Nsm Gene of Tomato Spotted Wilt Virus". The entire content of the patent is incorporated herein by reference. EHA105-35S-TSWV_NSm is a strain obtained by introducing the pK2-35S-TSWV_NSm vector into the *A. tumefaciens* EHA105, which strain is preserved in Yunnan Academy of Tobacco Agricultural Sciences. It has been demonstrated in Chinese patent no. ZL201710414755.X that the leaves of *N. alata* and 'Polata' generate obvious cell death hypersensitive reaction after inoculation of EHA105-35S-TSWV_NSm, indicating that the avirulence gene of TSWV for interaction with the RTSW gene in *N. alata* and 'Polata' tobacco is NSm.

pK2-35S-TZSV_NSm is a pK2GW7 plant expression vector carrying the TZSV NSm gene (NCBI accession number: KM374588), the construction method of which is the same to that of the above pK2-35S-NSm vector. See, Chinese patent no. ZL201710414755.X, wherein the TZSV NSm gene was cloned from the cDNA of TZSV. EHA105-35S-TZSV_NSm is a strain obtained by introducing the pK2-35S-TZSV_NSm vector into the *A. tumefaciens* EHA105, which strain is preserved in Yunnan Academy of Tobacco Agricultural Sciences.

p2300-35S-Sw-5b is a vector obtained by inserting the full length tomato Sw-5b gene (NCBI accession number: AY007366) into pCambia2300 plasmid, wherein the Sw-5b gene was cloned from genomic DNA of tomato cultivar 43419. The construction method of p2300-35S-Sw-5b vector is described in "Zhao W, Jiang L, Feng Z, Chen X, Huang Y, Xue F, Huang C, Liu Y, Li F, Liu Y et al. Plasmodesmata targeting and intercellular trafficking of Tomato spotted wilt tospovirus movement protein NSm is independent of its function in HR induction. Journal of General Virology (2016), 97, 1-8". EHA105-35S-Sw-5b is a strain obtained by introducing the p2300-35S-Sw-5b vector into *A. tumefaciens* EHA105, which strain is preserved in Yunnan Academy of Tobacco Agricultural Sciences.

pRGEB31-PF is a CRISPR/Cas9 gene editing vector previously constructed by the applicant and preserved in Yunnan Academy of Tobacco Agricultural Sciences. The construction method of pRGEB31-PF is described in the Chinese invention patent no. ZL201811347308.8, entitled "Recombinant Vector for Rapid Production of Transgenic Free Gene Editing Plants and Method of Use". The entire content of the patent is incorporated herein by reference.

Example 1: Fine Mapping and Bioinformatics Analysis of the RTSW Gene

In previous experiments of screening for tobacco plants resistant to spotted wilt disease without linkage drag, we obtained 18 tobacco plants having a shortened RTSW introgressed segment and no linkage drag, wherein five individual plants (No. 1, No. 4, No. 11, No. 12, and No. 17) could generate cell death hypersensitive reaction (HR) when transiently expressing the NSm gene, and accordingly had spotted wilt disease resistance; The remaining 13 individual plants (No. 2, No. 3, No. 5, No. 6, No. 7, No. 8, No. 9, No. 10, No. 13, No. 14, No. 15, No. 16, and No. 18) failed to generate HR when transiently expressing the NSm gene. The detection result of molecular markers indicated that the RTSW introgressed segment in the plant No. 12 was the shortest, with only NaChr3_59M marker was positive and the others were negative (see, international patent application no. PCT/CN2021/129382 and Chinese patent application no. 202111311707.0).

We detected the 13 individual plants without HR using previously developed NaChr3_59M and NaChr3_60M markers (see, international patent application no. PCT/CN2021/129382 and Chinese patent application no. 202111311707.0), using the plant No. 12 as a control. The results showed that NaChr3_60M was negative in 14 individual plants, except for the donor parent 'Polalta' that was used as a positive control (Table 2). NaChr3_59M was positive in plants No. 2, No. 9, No. 13, No. 14, No. 16 and No. 18 that did not have HR, and positive in the plant No. 12 that had HR. Thus we speculated that the RTSW gene was located between NaChr3_59M and NaChr3_60M.

To fine map the RTSW gene, we developed molecular markers NaChr3_59.2M (SEQ ID NO: 9) and NaChr3_59.7M (SEQ ID NO: 10) between NaChr3_59M and NaChr3_60M, and the markers were detected for the plant No. 12 and the 13 individual plants. NaChr3_59.2M was positive only in plants No. 12 and No. 16, and NaChr3_59.7M was positive only in the plant No. 12.

TABLE 1

Molecular Marker Primers

| Marker name | Primer name | Primer sequence (5'-3') | Sequence ID No. |
|---|---|---|---|
| NaChr3_59.2M | NaChr3_59.2MF | CGGTATGCGAGATTCTGATCC | SEQ ID NO: 11 |
| | NaChr3_59.2MR | TCCTCAACCTCCACGAACG | SEQ ID NO: 12 |
| NaChr3_59.7M | NaChr3_59.7MF | AGTCTTCTGCCGCTCCATC | SEQ ID NO: 13 |
| | NaChr3_59.7MR | TCGACCCAAGTATTCGCCATT | SEQ ID NO: 14 |

TABLE 2

Detection Results of Molecular Markers

| Individual plant | Marker name | | | | Resistance identification |
|---|---|---|---|---|---|
| | NaChr3_59M | NaChr3_59.2M | NaChr3_59.7M | NaChr3_60M | |
| No.2 | Pos | Neg | Neg | Neg | No HR |
| No.3 | Neg | Neg | Neg | Neg | No HR |
| No.5 | Neg | Neg | Neg | Neg | No HR |
| No.6 | Neg | Neg | Neg | Neg | No HR |
| No.7 | Neg | Neg | Neg | Neg | No HR |
| No.8 | Neg | Neg | Neg | Neg | No HR |
| No.9 | Pos | Neg | Neg | Neg | No HR |
| No.10 | Neg | Neg | Neg | Neg | No HR |
| No.13 | Pos | Neg | Neg | Neg | No HR |
| No.14 | Pos | Neg | Neg | Neg | No HR |
| No.15 | Neg | Neg | Neg | Neg | No HR |
| No.16 | Pos | Pos | Neg | Neg | No HR |
| No.18 | Pos | Neg | Neg | Neg | No HR |
| No.12 | Pos | Pos | Pos | Neg | Has HR |
| Polalta | Pos | Pos | Pos | Pos | Has HR |
| K326 | Neg | Neg | Neg | Neg | No HR |

Note:
"Pos" means positive, "Neg" means negative, and "HR" means hypersensitive reaction. "Has HR" means having spotted wilt disease resistance, and "No HR" means not having spotted wilt disease resistance.

Figures 1, 2:
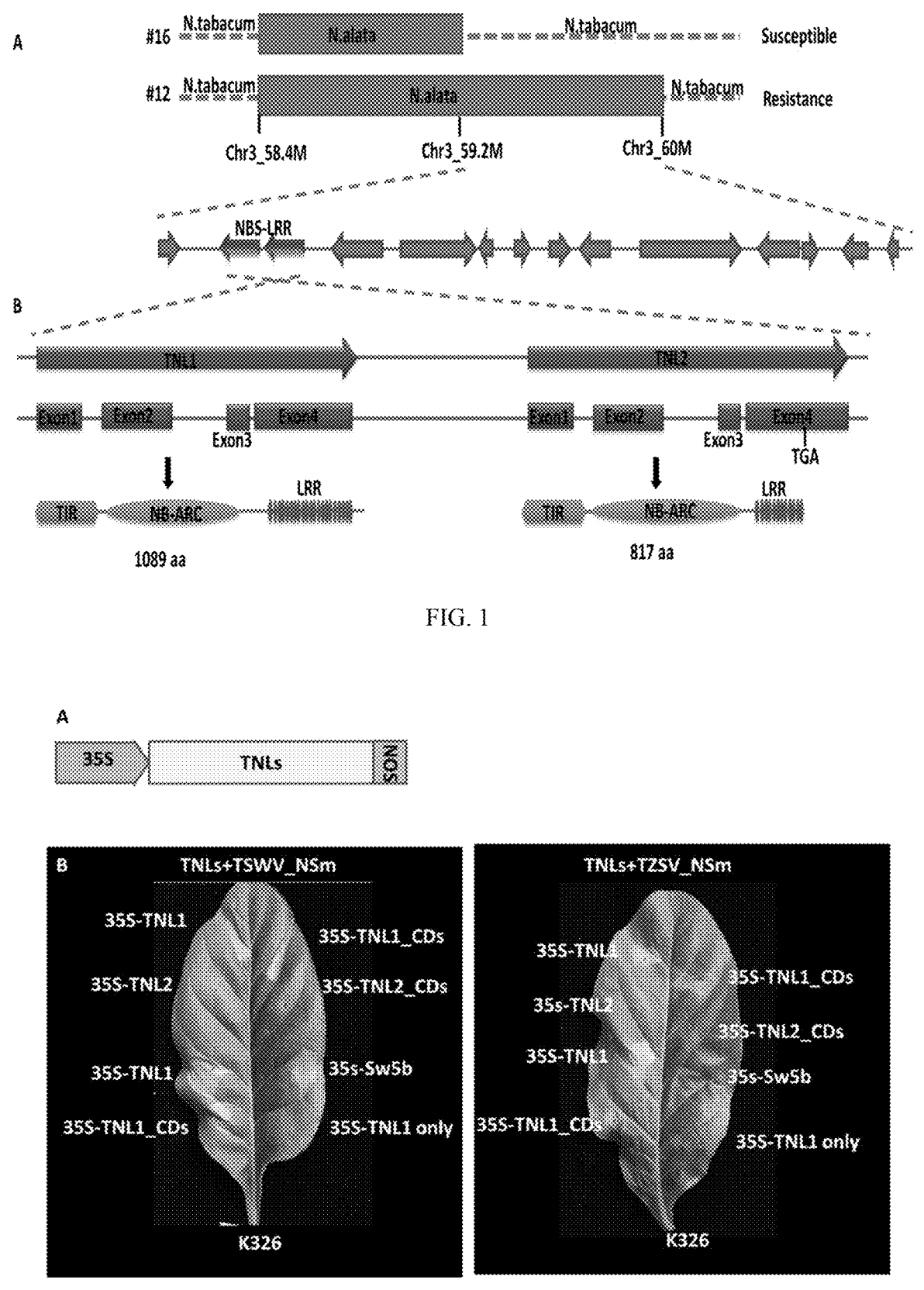

The results showed that NaChr3_59.7M was negative in the plants without HR (i.e., without the RTSW gene). NaChr3_59.2M was positive in the plant No. 16 having the longest RTSW introgressed segment and no HR, while NaChr3_60M was negative in the plant No. 12 having the shortest RTSW introgressed segment and HR, thus the RTSW gene was located in an interval of 59201149-59996790 bp (approximately 0.8 Mb) on chromosome 3 of the *N. alata* genome (FIG. 1A).

Typical resistance genes of plants, which conform to the "gene to gene" hypothesis, generally have a structure of nucleotide-binding site (NBS) and leucine-rich repeat (LRR) (Moffett, Advances in virus research, 2009, vol. 75, 1-33, 228-229). It was demonstrated earlier by the inventors that NSm is the avirulence gene to the RTSW gene (see, Chinese patent no. ZL201710414755.X), indicating that the RTSW gene is highly likely to be a resistance gene of the typical NBS-LRR class. On these grounds, we conducted bioinformatics analysis on the 59201149-59996790 bp interval of chromosome 3 of the *N. alata* genome, and found that there were only two NBS-LRR resistance genes in this interval, namely YC03G182780 and YC03G182790 (Table 3, FIG. 1B).

TABLE 3

Gene Predictions in the Candidate Genome Interval

| Serial number of gene | Starting position | Termination position | Forward/reverse strand | Function prediction |
|---|---|---|---|---|
| YC03G181850 | 59234660 | 59236188 | + | Methyltransferase like protein 13 subtype X2 |
| YC03G182780 | 59442334 | 59446963 | − | Disease resistant protein TAO1 like subtype X1 |
| YC03G182790 | 59454307 | 59458838 | − | TMV resistance protein N gene homologous gene |
| YC03G182870 | 59480597 | 59487324 | − | Peroxisome biogenesis protein 7 |
| YC03G182970 | 59528955 | 59541903 | + | Unspecified protein LOC104241095 |
| YC03G182990 | 59544264 | 59545172 | − | Unspecified protein LOC104085195 subtype X2 |
| YC03G183630 | 59758320 | 59759344 | + | WAT1 associated protein At2g39510 homologous gene |
| YC03G183770 | 59821311 | 59823050 | + | Hypothetical protein A4A49_18824 |
| YC03G183780 | 59823903 | 59826790 | − | Bobber 2 protein |
| YC03G183800 | 59834899 | 59853283 | + | Matrix metalloproteinase 2 like |
| YC03G183820 | 59848139 | 59854866 | − | Speculated magnesium transporter nipal |
| YC03G183830 | 59857091 | 59863238 | − | Bifunctional dTDP-4-dehydrorhamnose 3,5-epimerase/dTDP-4-dehydrorhamnose reductase |
| YC03G184000 | 59915873 | 59918040 | + | F-box protein CPR30 subtype X1 |
| YC03G184010 | 59920866 | 59924434 | − | Flowering time control protein FY subtype X2 |
| YC03G184120 | 59949275 | 59949955 | − | Hypothetical protein EJD97_007047 |

Through online software (see: the NCBI website) analysis of conserved domains, we found that YC03G182780 and YC03G182790 both contain typical TIR, NB-ARC, and LRR conserved domains, so they are Toll/interleukin-1 receptor nucleotide-binding site leucine-rich repeat (TIR-NBS-LRR, TNL) type resistance genes (Table 4). YC03G182790 and YC03G182780 were named TNL1 and TNL2 respectively as candidate genes.

PCR product was stored at 4° C. The cloning sequencing and sequence alignment of the PCR product showed that the sequences of TNL1 and TNL2 from $N.$ $alata$ and K326$^{RTSW}$ were identical, and they were consistent with the gene sequences obtained by genome assembly.

RNA was extracted from leaves of $N.$ $alata$ tobacco using a plant total RNA extraction kit (Qiagen, Cat. No. 74904) following the product instructions, and then reverse tran-

TABLE 4

Conserved Domains Analysis of TNL1 and TNL2 Genes

| Gene | Domain | Accession No. | Description | Interval | E value |
|---|---|---|---|---|---|
| TNL2 | PLN03210 | PLN03210 | Anti $P.$ $syringae$ 6 | 28-1995 | 2.59E−88 |
|  | TIR | pfam01582 | TIR domain | 52-495 | 1.28E−54 |
|  | TIR | smart00255 | Toll-Interleukin 1-resistance | 52-468 | 6.77E−37 |
|  | PLN03194 | PLN03194 | Putative disease resistance protein; provisional | 28-474 | 7.00E−19 |
|  | TIR_2 | pfam13676 | TIR domain | 58-348 | 2.59E−17 |
|  | NB-ARC | pfam00931 | NB-ARC domain | 1075-1692 | 1.51E−11 |
| TNL1 | PLN03210 | PLN03210 | Anti $P.$ $syringae$ 6 | 28-2013 | 1.14E−81 |
|  | TIR | pfam01582 | TIR domain | 52-498 | 5.06E−51 |
|  | TIR | smart00255 | Toll-Interleukin 1-resistance | 52-465 | 5.98E−35 |
|  | PLN03194 | PLN03194 | Putative disease resistance protein | 28-360 | 5.04E−18 |
|  | TIR_2 | pfam13676 | TIR domain | 58-348 | 6.29E−17 |
|  | NB-ARC | pfam00931 | NB-ARC domain | 1078-1695 | 2.32E−12 |
|  | PLN00113 | PLN00113 | Leucine rich repeat receptor like protein kinase | 3123-3821 | 2.09E−05 |

Example 2: Cloning and Structural Analysis of Candidate Genes

Specific primers for the full length of TNL1 and TNL2 genes were designed according to genomic information (Table 5). Leaf genomic DNA was extracted from $N.$ $alata$ and K326$^{RTSW}$ tobacco using a plant genomic DNA extraction kit (TIANGEN, Cat. No. DP360) following the instructions. Using the genomic DNA as template, the full length TNL1 gene was amplified with TNL1_35SF and TNL1_35SR primers, and the full length TNL2 gene was amplified with TNL2_35SF and TNL2_35SR primers. The PCR reaction system was as follows: 2×Phanta Max Buffer (Vazyme, Cat. No. P505) 25 µl, dNTP Mix (10 mM each) 1 µl, 10 µM forward primer 2 µl, 10 µM reverse primer 2 µl, Phanta Max Super-Fidelity DNA Polymerase 1 µl, template DNA 2 µl, adding ddH$_2$O to a total volume of 50 µl. The PCR reaction procedure was as follows: pre-denaturation for 3 min at 95° C.; followed by 35 cycles: denaturation for 15 s at 95° C., annealing for 15 s at 60° C., extension for 4 min at 72° C.; and a final elongation step for 5 min at 72° C. The scribed into cDNA using a 1st-strand cDNA synthesis kit (Vazyme, Cat. No. R312-01) following the reverse transcription system and procedure described in the kit instructions. Using the obtained cDNA as template, the full length CDs of TNL1 (coding region of the cDNA) was amplified with TNL1_35SF and TNL1_35SR primers, and the full length CDs of TNL2 was amplified with TNL2_35SF and TNL2_35SR primers. PCR reaction system and procedure were the same as above. The full-length CDs sequence was obtained by sequencing the PCR products, and then aligned to the genome sequence of $N.$ $alata$ to analyze the structure of transcripts of the genes.

TABLE 5

Amplification Primers of TNL1 and TNL2

| Primer name | Primer sequence | Sequence ID No. |
|---|---|---|
| TNL1_35SF | catttggagaggacacgctcgagATGGATACTCAATTAGTTAGAGG | SEQ ID NO: 15 |
| TNL1_35SR | tctcattaaagcaggactctagaGATTTGGCCAAGGGAAAAAGATTACG | SEQ ID NO: 16 |
| TNL2_35SF | catttggagaggacacgctcgagATGGATACTCAATTAGTTAGAGTAG | SEQ ID NO: 17 |
| TNL2_35SR | tctcattaaagcaggactctagaGTTAGGATTGGTTGGGTGGACTA | SEQ ID NO: 18 |

Note:
the amplification products of TNL1_35SF and TNL1_35SR primers comprise 230bp of 3'UTR region.
The amplification products of TNL2_35SF and TNL2_35SR primers comprise 150bp of 3'UTR region.
The above primers contain the overlap sequence (indicated in lowercase) on both ends of linearized phellsgate8 for recombinant cloning.

The results showed that both TNL1 and TNL2 have 4 exons and 3 introns (FIG. 1B). TNL1 gene is 4532 bp in full length (the gene sequence without a stop codon is set forth in SEQ ID NO: 1. The CDs of TNL1 is 3270 bp in length (the CDs sequence without a stop codon is set forth in SEQ ID NO: 2), encoding a protein sequence of 1089 amino acids (SEQ ID NO: 3). TNL2 gene is 4630 bp in full length (SEQ ID NO: 5). The CDs of TNL2 is 2454 bp in length (SEQ ID NO: 6), encoding a protein sequence of 817 amino acids (SEQ ID NO: 7). Although the gene structures of TNL2 and TNL1 are similar, TNL2 has an early stop codon in the fourth exon, resulting in truncated CDs.

Example 3. Preliminary Verification of the Function of Candidate Genes Using Avirulence Gene Infiltration Method To determine whether TNL1 and TNL2 are RTSW genes, preliminary verification was conducted using a disease resistance gene identification system established earlier by the inventors. See, Chinese invention patent no. ZL201710415015.8, entitled "A Method for Screening Disease Resistance Genes Using NSm Gene of Tomato Spotted Wilt Virus". The entire content of the patent is incorporated herein by reference.

The phellsgate8 empty plasmids were double digested with XhoI and XbaI restriction enzymes to yield linearized phellsgate8 plasmids. The full-length TNL1 gene, full-length CDs of TNL1, full-length TNL2 gene and full-length CDs of TNL2 obtained in Example 2 were respectively cloned into phellsgate8 plasmids using ClonExpres One Step Cloning Kit (Vazyme, Cat. No. C112-01) following the product instructions, obtaining recombinant plasmids 35S-TNL1, 35S-TNL1_CDs, 35S-TNL2 and 35S-TNL2_CDs. 35S-TNL1 expressed full length TNL1 gene; 35S-TNL1_CDs expressed full-length CDs of TNL1; 35S-TNL2 expressed full-length TNL2 gene; 35S-TNL2_CDs expressed full-length CDs of TNL2. Expression of these genes was driven by a 35S promoter. 35S-TNL1, 35S-TNL1_CDs, 35S-TNL2 and 35S-TNL2_CDs were respectively transformed into *Escherichia coli* DH5α by heat-shock method, and sequencing identification was performed to obtain recombinant plasmids with accurate insert sequences.

35S-TNL1, 35S-TNL1_CDs, 35S-TNL2 and 35S-TNL2_CDs were respectively introduced into *A. tumefaciens* EHA105 to generate recombinant bacteria EHA105-35S-TNL1, EHA105-35S-TNL1 CDs, EHA105-35S-TNL2 and EHA105-35S-TNL2 CDs. The obtained recombinant bacteria were cultured in LB medium at 28° C. for 24 h, collected by centrifugation, and resuspended in infiltration buffer (10 mmol/L MgCl$_2$, 10 mmol/L MES, 200 μmol/L acetosyringone) to obtain a bacterial suspension with an OD600 of 0.5. Bacterial suspension of EHA105-35S-TSWV_NSm, EHA105-35S-TZSV_NSm and EHA105-35S-Sw-5b, with an OD600 of 0.5, was prepared using the same method respectively.

The bacterial suspension of EHA105-35S-TSWV_NSm or EHA105-35S-TZSV NSm was mixed with the bacterial suspension of EHA105-35S-TNL1, EHA105-35S-TNL1_CDs, EHA105-35S-TNL2 or EHA105-35S-TNL2_CDs at a volume ratio of 1:1, obtaining eight bacterial suspensions to be tested. The bacterial suspension of EHA105-35S-TSWV NSm and the bacterial suspension of EHA105-35S-Sw-5b were mixed at a volume ratio of 1:1 as a positive control suspension. OD600 of the bacterial suspension was controlled to 0.5. Inoculation of tobacco leaves: using a sterile syringe with the needle removed to inject 9.5-10.5 microliters of a bacterial suspension into a leaf of the susceptible tobacco 'K326' from the leaf back to form a visible infiltration spot; placing the inoculated tobacco plant in an environment of 20-28° C. and 80% humidity, alternately providing continuous illumination for 16 hours and continuous darkness for 8 hours, and observing a total of 72 hours. The leaf of the susceptible tobacco 'K326' was inoculated with the positive control suspension and the bacterial suspension of EHA105-35S-TNL1 only using the same method. If a bacterial suspension could induce cell death hypersensitive reaction (HR) on the leaf of the susceptible tobacco 'K326', it indicated that the candidate gene in the bacterial suspension is the disease resistance gene of the avirulence gene NSm in the bacterial suspension.

The results showed that the mixed bacterial suspension of EHA105-35S-TNL1 and EHA105-35S-TSWV_NSm, the mixed bacterial suspension of EHA105-35S-TNL1 and EHA105-35S-TZSV_NSm, the mixed bacterial suspension of EHA105-35S-TNL1 CDs and EHA105-35S-TSWV_NSm, and the mixed bacterial suspension of EHA105-35S-TNL1 CDs and EHA105-35S-TZSV_NSm could induce HR on the leaf of 'K326', while EHA105-35S-TNL2 or EHA105-35S-TNL2_CDs, together with EHA105-35S-TSWV_NSm or EHA105-35S-TZSV_NSm, failed to induce HR on the leaf of 'K326'. As a control, the bacterial suspension of EHA105-35S-TNL1 only was unable to induce HR on the leaf of 'K326', indicating that HR phenotype was generated by co-activation of TNL1 gene and NSm gene (FIG. 2B). Thus, it can be preliminarily determined that the candidate gene TNL1 is the RTSW gene. Although TNL2 and TNL1 are only about 4 Kb apart and have a similar gene structure, TNL2 has nothing to do with HR stimulated by NSm, and may have no role in resistance to tobacco spotted wilt disease.

Example 4. Further Verification of the Function of Candidate Genes by Gene Knockout To further determine whether TNL1 and TNL2 are RTSW genes, TNL1 and TNL2 were knocked out in tobacco plants comprising the RTSW locus using a gene editing system established earlier by the inventors (see, Chinese patent no. ZL201811347308.8). The recombinant vectors used in the gene editing system are CRISPR/Cas9 vectors for plant gene editing that carry PAP1 and NtFT expression elements (PF Cassete). Since the NtFT expression element produces a protein that promotes early flowering in plants and the PAP1 expression element produces a protein that promotes anthocyanin biosynthesis in plants, the color of T0 transgenic plants can be used to determine whether an editing event occurred. Plants would appear purple if they comprise the transgenic elements and green if they do not comprise the transgenic elements.

Since TNL1 and TNL2 are highly homologous, a gRNA of a conserved sequence can be used to edit TNL1 and TNL2 respectively or simultaneously. A target sequence (gRNA: CTATGATGTTGATCCTTCTG (SEQ ID NO: 19)) was designed based on a conserved sequence in the first exon of TNL1 and TNL2. The 3' end of the gRNA is adjacent to "AGG", the PAM sequence of Cas9 nuclease (FIG. 3A). Two primers for the gRNA synthesis were as follows:
  gRNA-F: 5'-GGCACTATGATGTTGATCCTTCTG-3' (SEQ ID NO: 20)
  gRNA-R: 3'-CAGAAGGATCAACATCATAGCAAA-5' (SEQ ID NO: 21)

The method for constructing pRGEB31-PF vector was described in Chinese patent no. ZL201811347308.8. The target sequence was inserted into the pRGEB31-PF vector through two adjacent BsaI sites on the vector, so the forward sequence (gRNA-F) needed a "GGCA" adapter and the reverse sequence (gRNA-R) needed an "AAAC" adapter. The primers gRNA-F and gRNA-R were annealed to form a dimer structure. Annealing system: gRNA-F 20 µl, gRNA-R 20 µl, 10× Annealing buffer 5 µl, H₂O 5 µl. Annealing procedure: 95° C. 5 min, 90° C. 1 min, 80° C. 1 min, 70° C. 1 min, 60° C. 1 min, 50° C. 1 min, 40° C. 1 min, 30° C. 1 min, 20° C. 1 min, 10° C. 1 min. The gRNA was then inserted into the pRGEB31-PF vector digested with BsaI to obtain ligation products. The ligation products were transformed into *Escherichia coli* DH5α Competent cells, and plasmids were extracted and sequenced to obtain recombinant plasmids Cas9-PF-gRNA with correct insert sequence. Cas9-PF-gRNA plasmids were electroporated into *Agrobacterium* EHA105, and *Agrobacterium* mediated transformation of tobacco were performed. To achieve higher editing efficiency at T0 generation and to obtain homozygous mutants at T1 generation, K326$^{RTSW}$ tobacco plants with a genotype of heterozygous RTSW (RTSW/rtsw) were used to induce calli for tobacco transformation experiments. Under the background of heterozygous RTSW, only one allele needs to be edited to completely make the gene to be verified lose its function and show phenotypes. T0 transgenic positive plants were obtained after hygromycin resistance screening, differentiation and regeneration of resistant calli.

According to the target gene, specific primers (Table 6) were designed respectively upstream and downstream of the target sequence for detection of TNL1 and TNL2 gene mutants in transgenic tobacco.

TABLE 6

Primers for Detection of TNL1 and TNL2 Gene Mutation

| Primer name | Primer sequence | Sequence ID No. |
| --- | --- | --- |
| TNL1editTestF | AGGTGAAATTATGGCGAAAGTG | SEQ ID NO: 22 |
| TNL1editTestR | CTTCAGTAAGTGCAGCTCTCC | SEQ ID NO: 23 |
| TNL2editTestF | CTGGTCATCTTTATTCCAAATTAGA | SEQ ID NO: 24 |
| TNL2editTestR | TTGAATCAAGAATATGTACCCGTCAG | SEQ ID NO: 25 |

Genomic DNA was extracted from 30 T0 transgenic positive plants using a plant genomic DNA extraction kit (TIANGEN, Cat. No. DP360) following the instructions. Using the genomic DNA of each plant as template, sequences containing TNL1 editing sites were amplified with TNL1editTestF and TNL1editTestR primers, and sequences containing TNL2 editing sites were amplified with TNL2editTestF and TNL2editTestR primers. The PCR reaction system and procedure were the same as those in example 2. PCR products were sequenced by Thermo Fisher Scientific (Guangzhou, China) using TNL1editTestF or TNL2editTestF as sequencing primer.

Sequenced PCR products were analyzed for the presence of base substitutions, deletions, or insertions at the targeted site (i.e. 3 bp upstream of the PAM), to determine whether editing events occurred. The results showed that 21 out of 30 T0 transgenic positive plants had editing events at the target site of TNL1 or TNL2, with 70% editing efficiency, wherein 5 plants were edited only in TNL1, 4 plants were edited only in TNL2, and the remaining 12 plants were edited in both TNL1 and TNL2 (FIG. 3B). Since the calli used in the tobacco transformation experiments were induced from tobacco plants with a genotype of RTSW/rtsw, containing only one allele for either TNL1 or TNL2, any editing event targeting either TNL1 or TNL2 would affect the function of the corresponding gene, having an effect equivalent to that of homozygous mutants. Therefore, TSWV resistance detection can be directly performed on T0 plants.

The NSm gene was used to detect TSWV resistance in T0 plants according to the method described in Chinese patent no. ZL201710414755.X. Specifically, the EHA105-35S-TSWV_NSm bacteria were cultured in LB medium at 28° C. for 24 h, collected by centrifugation and resuspended in infiltration buffer (10 mmol/L MgCl₂, 10 mmol/L MES, 200 µmol/L acetosyringone) to obtain a bacterial suspension with an OD600 of 0.5. A sterile syringe with the needle removed was used to inject 9.5-10.5 microliters of a bacterial suspension into a tobacco leaf from the leaf back to form a visible infiltration spot; the inoculated tobacco plant was placed in an environment of 20-28° C. and 80% humidity, alternately providing continuous illumination for 16 hours and continuous darkness for 8 hours, observing a total of 72 hours. EHA105-35S-TZSV NSm was inoculated on tobacco leaves following the same procedure. If TSWV_NSm or TZSV_NSm could induce cell death hypersensitive reaction (HR) on leaves of T0 plants, it indicated that the T0 plants had resistance to TSWV or TZSV and their RTSW genes were functional; If TSWV_NSm or TZSV_NSm failed to induce HR on leaves of T0 plants, it indicated that the T0 plants had no resistance to TSWV or TZSV and their RTSW genes lost function.

In 30 T0 transgenic positive plants, there were 21 plants in which TNL1 and/or TNL2 were edited. The avirulence gene TSWV_NSm and TZSV_NSm failed to induce HR on 5 plants in which only TNL1 was edited and on 12 plants in which both TNL1 and TNL2 were edited. TSWV_NSm and TZSV_NSm induced significant HR on 4 plants in which only TNL2 was edited and on 9 plants in which both TNL1 and TNL2 were not edited (Table 7, FIG. 3C).

TABLE 7

Detection of TSWV Resistance in T0 Plants

| Number of T0 plants | Type of editing | TSWV_NSm | TZSV_NSm |
| --- | --- | --- | --- |
| 1 | Only TNLI was edited | No HR | No HR |
| 2 | Both TNL1 and TNL2 were edited | No HR | No HR |
| 3 | Both TNLI and TNL2 were not edited | HR | HR |
| 4 | Only TNL2 was edited | HR | HR |
| 5 | Only TNLI was edited | No HR | No HR |
| 6 | Both TNL1 and TNL2 were edited | No HR | No HR |
| 7 | Both TNLI and TNL2 were edited | No HR | No HR |
| 8 | Both TNL1 and TNL2 were not edited | HR | HR |
| 9 | Only TNL1 was edited | No HR | No HR |
| 10 | Both TNL1 and TNL2 were edited | No HR | No HR |
| 11 | Only TNL1 was edited | No HR | No HR |
| 12 | Only TNL2 was edited | HR | HR |
| 13 | Both TNL1 and TNL2 were not edited | HR | HR |
| 14 | Both TNL1 and TNL2 were edited | No HR | No HR |
| 15 | Only TNL2 was edited | HR | HR |
| 16 | Both TNL1 and TNL2 were not edited | HR | HR |
| 17 | Both TNL1 and TNL2 were edited | No HR | No HR |

TABLE 7-continued

Detection of TSWV Resistance in T0 Plants

| Number of T0 plants | Type of editing | TSWV_NSm | TZSV_NSm |
|---|---|---|---|
| 18 | Both TNL1 and TNL2 were not edited | HR | HR |
| 19 | Both TNL1 and TNL2 were edited | No HR | No HR |
| 20 | Both TNL1 and TNL2 were edited | No HR | No HR |
| 21 | Both TNL1 and TNL2 were not edited | HR | HR |
| 22 | Both TNL1 and TNL2 were edited | No HR | No HR |
| 23 | Only TNL2 was edited | HR | HR |
| 24 | Both TNL1 and TNL2 were not edited | HR | HR |
| 25 | Both TNL1 and TNL2 were edited | No HR | No HR |
| 26 | Both TNL1 and TNL2 were not edited | HR | HR |
| 27 | Only TNL1 was edited | No HR | No HR |
| 28 | Both TNLI and TNL2 were edited | No HR | No HR |
| 29 | Both TNL1 and TNL2 were not edited | HR | HR |
| 30 | Both TNL1 and TNL2 were edited | No HR | No HR |

To demonstrate that the editing events at TNL1 and TNL2 were heritable, and to exclude interference of the transgenic elements of the editing vectors to the editing events, two plants in which only TNL1 was edited (genotype: $tnl1^{CasKO}$/tnl1, TNL2/tnl2), two plants in which only TNL2 was edited (genotype: TNL1/tnl1, $tnl2^{CasKO}$/tnl2), two plants in which both TNL1 and TNL2 were edited (genotype: $tnl1^{CasKO}$/tnl1, $tnl2^{CasKO}$/tnl2), and two plants in which both TNL1 and TNL2 were not edited (genotype: TNL1/tnl1, TNL2/tnl2) were selected to self-cross separately to obtain T1 seeds. T1 seeds were sown separately and cultivated by a conventional method in a growth chamber to obtain T1 plants. Since the Cas9-PF-gRNA vector carries the anthocyanin visual marker, T1 plants would appear purple if they comprise the transgenic elements and green if they do not comprise the transgenic elements. When the T1 plants had 4-5 leaves, the fully green plants were selected and the genomic DNA was extracted from each plant for detection of genotype and editing homozygosity. Using genomic DNA as template, PCR reactions were performed with primer pairs TNL1editTestF/TNL1editTestR and TNL2editTestF/TNL2editTestR. If the PCR result is negative, it indicates that the genotype of the plant is rtsw/rtsw and the plant is a segregant without the RTSW introgressed segment. Therefore, only plants with positive PCR results were subjected to the next analysis. Sequencing results showed that the T1 plants with positive PCR results all contained the mutant type as expected, indicating that the editing events were heritable and that all the mutations were homozygous. The TSWV and TZSV infected leaf sap was respectively inoculated on T1 plants having positive PCR results. Plants were investigated for TSWV and TZSV incidence 14 d and 21d post inoculation (Table 8).

TABLE 8

Resistance of Edited Plants to TSWV and TZSV

| Type of editing | Lines of T0 plants | PCR results of T1 plants | Virus inoculated | Number of inoculated plants | Number of disease plants 14 dpi | Number of disease plants 21 dpi |
|---|---|---|---|---|---|---|
| Only TNLI was edited (genotype: $tnl1^{CasKO}$/tnl1, TNL2/tnl2) | 1# | Homozygous deletion of "C" in TNL1; TNL2 was not edited | TSWV<br>TZSV | 12<br>12 | 9<br>8 | 12<br>12 |
| | 5# | Homozygous deletion of "C" in TNL1; TNL2 was not edited | TSWV<br>TZSV | 12<br>12 | 8<br>9 | 12<br>12 |
| Only TNL2 was edited (genotype: TNL1/tnl1, $tnl2^{CasKO}$/tnl2) | 4# | TNL1 was not edited; Homozygous deletion of "TC" in TNL2 | TSWV<br>TZSV | 12<br>12 | 0<br>0 | 0<br>0 |
| | 12# | TNL1 was not edited; Homozygous deletion of "C" in TNL2 | TSWV<br>TZSV | 6<br>6 | 0<br>0 | 0<br>0 |
| Both TNLI and TNL2 were edited (genotype: $tnl1^{CasKO}$/tnl1, $tnl2^{CasKO}$/tnl2) | 2# | Homozygous deletion of "C" in TNL1; Homozygous insertion of "A" in TNL2 | TSWV<br>TZSV | 12<br>12 | 8<br>9 | 12<br>12 |
| | 6# | Homozygous deletion of "T" in TNL1; Homozygous deletion of "TC" in TNL2 | TSWV<br>TZSV | 12<br>12 | 7<br>6 | 12<br>12 |
| Both TNL1 and TNL2 were not edited (genotype: TNL1/tnl1, TNL2/tnl2) | 3# | Both TNL1 and TNL2 were not edited | TSWV<br>TZSV | 12<br>12 | 0<br>0 | 0<br>0 |
| | 13# | Both TNLI and TNL2 were not edited | TSWV<br>TZSV | 12<br>12 | 0<br>0 | 0<br>0 |

As shown in Table 8, the T1 plants, in which only TNL2 was edited or both TNL1 and TNL2 were not edited, had an incidence of 0% 14 days post inoculation, showing high resistance; while the T1 plants, in which only TNL1 was edited or both TNL1 and TNL2 were edited, had an incidence of 100%, showing susceptibility. The above results showed that if the TNL1 was edited, the plants comprising the RTSW locus would completely lose resistance to spotted wilt disease, while editing only TNL2 had no effect on resistance of the plants.

Example 5. Identification of Broad Spectrum of Resistance to Spotted Wilt Disease in Stably Transformed Tobacco Carrying TNL1

To determine whether the TNL1 alone has the full function of the RTSW locus, and to identify whether TNL1 has broad-spectrum resistance to spotted wilt disease, we cloned the full-length gene proTNL1:TNL1 (SEQ ID NO: 8) with the native TNL1 promoter (SEQ ID NO: 4). Primer TNL1_NatProF (Table 9) was designed approximately 2 Kb upstream of the start codon ATG in the reading frame of TNL1. Using the genomic DNA of N. alata as template, proTNL1:TNL1 was amplified with TNL1_NatProF and TNL1_35SR primers. The PCR reaction system and procedure were the same as those in Example 2. A specific band of 6.6 Kb was obtained. The phellsgate8 empty plasmids were double digested with SacI and XbaI restriction enzymes to yield linearized phellsgate8 plasmids. The PCR products were cloned into phellsgate8 plasmids using ClonExpres One Step Cloning Kit (Vazyme, Cat. No. C112-01) following the product instructions, obtaining recombinant plasmids phellsgate8-proTNL1:TNL1. The recombinant plasmids phellsgate8-proTNL1:TNL1 were transformed into Escherichia coli DH5α, and positive clones were picked up for sequencing. Sequencing results showed that the sequence of amplified proTNL1:TNL1 was consistent with the gene sequence obtained by genome assembly, so the proTNL1:TNL1 sequences inserted in the recombinant plasmids were accurate without mutations.

TABLE 9

| Primer TNL1_NatProF | | | |
|---|---|---|---|
| Primer name | Primer sequence | Sequence ID No. | Notes |
| TNL1_NatProF | tgcatccaacgcgtt gggagctcAGCCAAA CACCAATTCTTTCCC TTTAC | SEQ ID NO: 26 | The primer is located at 1875 bp upstream of the start codon of TNL1, containing the overlap sequence (indicated in lowercase) on both ends of linearized phellsgate8 for recombinant cloning. |

The phellsgate8-proTNL1:TNL1 plasmids were introduced into A. tumefaciens EHA105 strain to obtain recombinant bacteria EHA105-phellsgate8-proTNL1:TNL1. EHA105-phellsgate8-proTNL1:TNL1 bacteria were cultured in A. tumefaciens LB medium at 28° C. for 24 h, and collected by centrifugation.

Calli were induced from susceptible tobacco 'K326' and infected by EHA105-phellsgate8-proTNL1:TNL1. After kanamycin resistance screening, resistant calli were obtained, differentiated and regenerated into T0 transgenic plants. Genomic DNA was extracted from the T0 transgenic plants and PCR reactions were performed using TNL1editTestF/TNL1editTestR primer pair. Plants with positive PCR results were proTNL1:TNL1 transgenic positive plants.

In order to prove the resistance of TNL1 transgenic plants to viruses, two T0 generation proTNL1:TNL1 transgenic positive plants (proTNL1:TNL1-#1 and proTNL1:TNL1-#2) were randomly selected and self-crossed to obtain T1 seeds. The T1 seeds were sown separately and cultivated by conventional methods in a growth chamber to obtain T1 plants. When T1 plants had 4-5 leaves, genomic DNA was extracted from each plant, and transgenic detection was performed using TNL1editTestF/TNL1editTestR primers. T1 plants with positive detection results were selected and respectively inoculated with disease leaf juice of TSWV, INSV, TZSV, CCSV, CaCV, TNSV, PCSV and HCRV. Plants were investigated for incidence 21 days post inoculation (Table 10).

TABLE 10

Incidence of Transgenic Plants Inoculated with Orthotospoviruses

| Virus inoculated | Inoculated plants (Number of disease plants/Number of inoculated plants) | | |
|---|---|---|---|
| | proTNL1:TNL1-#1 | proTNL1:TNL1-#2 | K326 |
| TSWV | 0/12 | 0/12 | 12/12 |
| INSV | 0/12 | 0/12 | 4/12 |
| TZSV | 0/12 | 0/12 | 12/12 |
| CCSV | 0/20 | 0/20 | 4/20 |
| CaCV | 1/12 | 1/12 | 3/12 |
| TNSV | 3/12 | 4/12 | 3/12 |
| PCSV | 2/12 | 3/12 | 3/12 |
| HCRV | 3/10 | 2/10 | 3/10 |

Figures 4, 5:
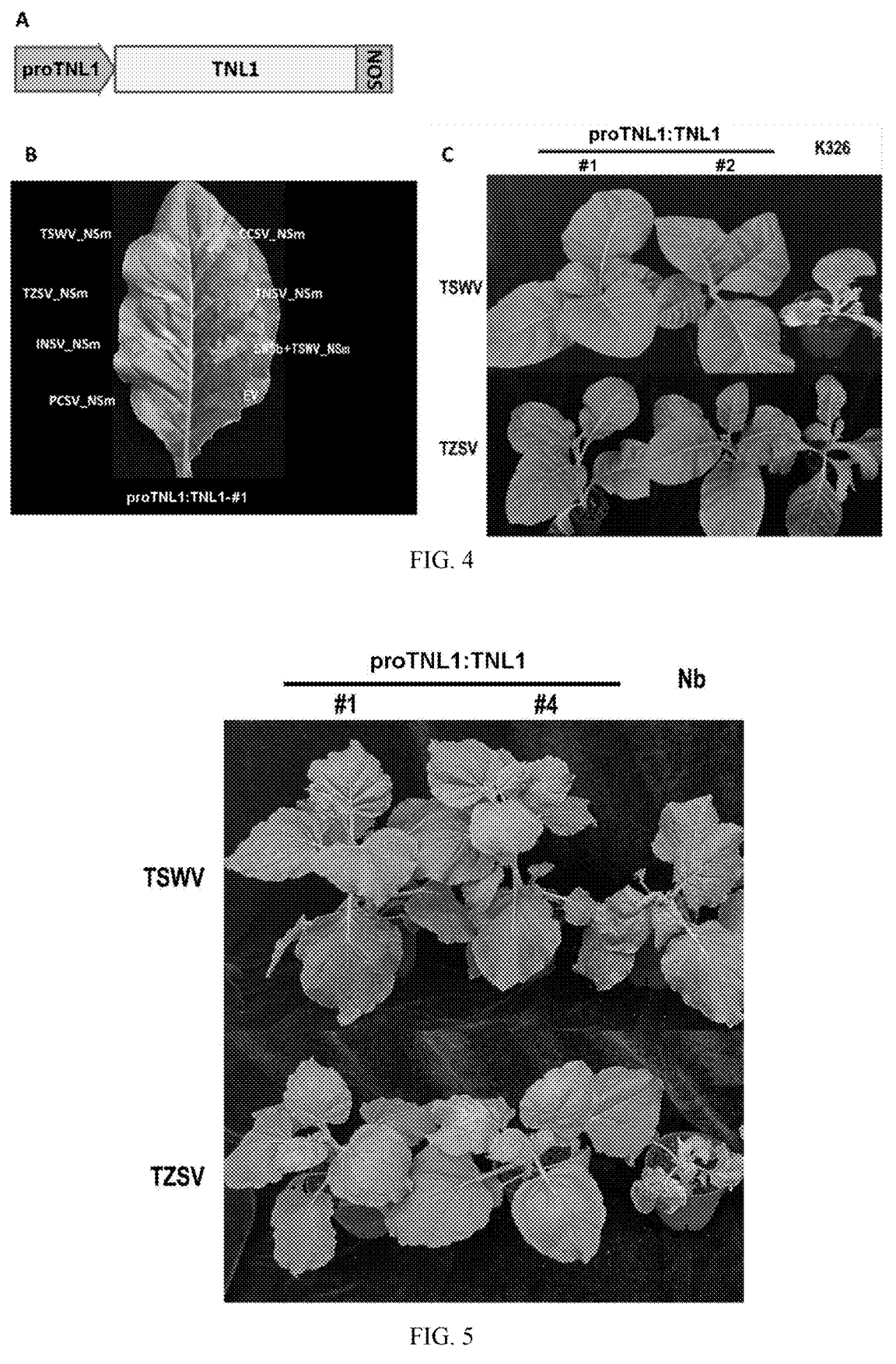

Virus inoculation results showed that the two independent proTNL1:TNL1 transgenic plants had resistance to the American type viruses TSWV and INSV and the Eurasian type viruses TZSV and CCSV. In all the transgenic plants, no virus was detected in the systemic leaves (FIG. 4C). For the Eurasian type viruses CaCV, the incidence of the virus declined significantly in proTNL1:TNL1 transgenic plants relative to non-transgenic controls, and the symptoms of the virus were significantly reduced, showing certain disease resistance. As a control, non-transgenic cultivated tobacco K326 was highly susceptible. The results of virus inoculation experiments showed that transgenic tobacco expressing TNL1 alone could develop resistance to five orthotospoviruses, having broad-spectrum resistance. The above results indicate that transgenic expression of TNL1 alone is sufficient to function as the RTSW locus, thus it is confirmed that TNL1 confers resistance to spotted wilt disease. TNL1 is the RTSW gene.

The inventors have demonstrated that the NSm gene of Orthotospoviruses is the avirulence gene corresponding to the resistance gene RTSW. To further demonstrate the broad-spectrum resistance of RTSW, infiltration of NSm genes of viruses can be utilized to detect resistance of plants having RTSW to orthotospoviruses, following the detection method described in the Chinese patent no. ZL201710414755.X. By specific amplification of NSm genes from viral genomic cDNA or artificial synthesis of NSm genes, we constructed expression vectors of NSm genes of 14 orthotospoviruses (including American type viruses TSWV, CSNV, GRSV, and INSV, and Eurasian type viruses TZSV, CCSV, MVBaV, CaCV, GBNV, TNSV, PCSV, TNRV, PolRSV, and HCRV). The NSm genes of the 14 viruses were respectively cloned into pCambia1300-YFP expression vectors to obtain recombinant plasmids pCambia1300-NSm-YFP. In the pCambia1300-NSm-YFP, the NSm gene is located downstream of a 35S promoter, in a complete reading frame with a YFP gene, allowing expression of NSm-YFP fusion proteins, wherein the YFP tag is used for detection of protein expression levels. The pCambia1300-NSm-YFP plasmids were introduced into *A. tumefaciens* EHA105 to obtain EHA105-pCambia1300-NSm-YFP. The pCambia1300-YFP plasmids were introduced into *A. tumefaciens* EHA105 to obtain EHA105-pCambia1300-YFP as a control strain carrying empty vectors.

The bacterial suspension of EHA105-35S-TSWV_NSm (OD600=0.5) and the bacterial suspension of EHA105-35S-Sw-5b (OD600=0.5) was mixed at a volume ratio of 1:1 as a positive control suspension. The bacterial suspension of EHA105-pCambia1300-YFP (OD600=0.5) was used as a negative control suspension. The largest two leaves from the selected two T1 transgenic positive plants and the wild-type control K326 plants were infiltrated with bacterial suspension using 2 ml syringes, wherein each leaf was injected with eight samples, wherein one was the positive control suspension, one was the negative control suspension, and the remaining six were respectively bacterial suspension of EHA105-pCambia1300-NSm-YFP (OD600=0.5) of six viruses. Each sample had three replicates. After inoculation, the plants were cultivated in a growth chamber at 20-28° C. for 72 h. Plants were observed for cell death hypersensitive reaction (HR).

The results showed that the positive control suspension induced HR on the leaves of all T1 generation proTNL1:TNL1 transgenic positive plants, while the negative control suspension failed to induce HR on the leaves of all T1 generation proTNL1:TNL1 transgenic positive plants. Expression of viral NSm alone and virus inoculation showed highly consistent resistance results in two independent proTNL1:TNL1 transgenic positive plants. Like the positive control, the NSm genes of all the four tested American type viruses TSWV, CSNV, GRSV and INSV, and five tested Eurasian type viruses TZSV, CCSV, MVBaV, CaCV and GBNV induced significant HR. Like the empty vector control, the NSm genes of TNSV, PCSV, TNRV, PolRSV and HCRV failed to induce HR. In non-transgenic common K326 cultivated tobacco, the NSm genes of all viruses failed to induce any degree of HR (Table 11).

TABLE 11

Detection of Orthotospoviruses Resistance of Transgenic Plants by Infiltration with EHA105-pCambia1300-NSm-YFP

| EHA105-pCambia1300- NSm-YFP infiltrated | Number of plants had HR/Total number of infiltrated plants | | |
|---|---|---|---|
| | proTNL1: TNL1-#1 | proTNL1: TNL1-#2 | K326 |
| TSWV_NSm | 6/6 | 6/6 | 0/6 |
| INSV_NSm | 6/6 | 6/6 | 0/6 |
| CSNV_NSm | 6/6 | 6/6 | 0/6 |
| GRSV_NSm | 6/6 | 6/6 | 0/6 |
| TZSV_NSm | 6/6 | 6/6 | 0/6 |
| CCSV_NSm | 6/6 | 6/6 | 0/6 |
| MVBaV_NSm | 6/6 | 6/6 | 0/6 |
| CaCV_NSm | 2/6 | 2/6 | 0/6 |
| GBNV_NSm | 6/6 | 6/6 | 0/6 |
| TNSV_NSm | 0/6 | 0/6 | 0/6 |
| PCSV_NSm | 0/6 | 0/6 | 0/6 |
| TNRV_NSm | 0/6 | 0/6 | 0/6 |
| PolRSV_NSm | 0/6 | 0/6 | 0/6 |
| HCRV_NSm | 0/6 | 0/6 | 0/6 |
| EHA105-35S-TSWV_NSm + EHA105-35S-Sw-5b | 6/6 | 6/6 | 6/6 |
| EHA105-pCambia1300-YFP (empty vector) | 0/6 | 0/6 | 0/6 |

The above experiments in the Example 3, 4 and 5 proved that TNL1 is the RTSW. Knockout of the RTSW gene alone would make resistant plants lose resistance to spotted wilt disease, and transgenosis of RTSW alone was sufficient to confer plants broad-spectrum resistance to spotted wilt disease, so the RTSW gene was sufficient and necessary for resistance to spotted wilt disease.

Example 6. Functional Verification of RTSW Gene in *Nicotiana benthamiana*, Tomato and Potato To prove the wide adaptability of the RTSW gene, we selected other solanaceous crops for RTSW transgenic experiments. Calli were induced from the common susceptible materials *N. benthamiana*, cultivated potato (*Solanum tuberosum* L.) and cultivated tomato (*S. lycopersicum*). EHA105-phellsgate8-proTNL1:TNL1 bacteria were transferred into the calli of *N. benthamiana*, potato and tomato respectively. After kanamycin resistance screening, resistant calli were obtained, differentiated and regenerated into T0 transgenic plants. Genomic DNA was extracted from the T0 transgenic plants and PCR reactions were performed using TNL1editTestF/TNL1editTestR primer pair. Plants with positive PCR results were proTNL1:TNL1 transgenic positive plants. For *N. benthamiana* and tomato, 2-3 T0 transgenic positive plants were randomly selected and self-crossed to obtain T1 seeds. For potatoes that are propagated asexually through tubers, T0 tubers were directly harvested. The T1 seeds and T0 potato tubers of transgenic positive plants were sown and cultivated by conventional methods in a growth chamber. When plants had 4-5 leaves, genomic DNA was extracted from each plant for detection of transgenic elements. The plants with positive detection results were selected and inoculated with disease leaf juice of TSWV and TZSV respectively. Plants were investigated for incidence of TSWV and TZSV 14 and 21 days post inoculation, respectively (Table 12).

TABLE 12

Detection of Disease Resistance of Transgenic N. benthamiana, Tomato and Potato

| Lines inoculated with viruses | | Viruses inoculated (number of disease plants/ number of inoculated plants) | | | |
|---|---|---|---|---|---|
| | | TSWV | | TZSV | |
| | | 14 dpi | 21 dpi | 14 dpi | 21 dpi |
| N. benthamiana | proTNL1:TNL1-#1 | 0/15 | 0/15 | 0/15 | 0/15 |
| | proTNL1: TNL1-#4 | 0/15 | 0/15 | 0/15 | 0/15 |
| | Non-transgenic N. benthamiana | 15/15 | 15/15 | 15/15 | 15/15 |
| Potato (Solanum tuberosum L. Desiree) | proTNL1:TNL1-#1 | 0/9 | 0/9 | 0/9 | 0/9 |
| | proTNL1: TNL1-#2 | 0/8 | 0/8 | 0/9 | 0/9 |
| | Non-transgenic potato | 4/12 | 7/12 | 3/12 | 5/12 |
| Tomato (S. lycopersicum) | proTNL1:TNL1-#1 | 0/6 | 0/6 | 0/6 | 0/6 |
| | proTNL1: TNL 1-#2 | 0/6 | 0/6 | 0/6 | 0/6 |
| | Non-transgenic tomato | 7/12 | 9/12 | 5/12 | 7/12 |

Figure 6:
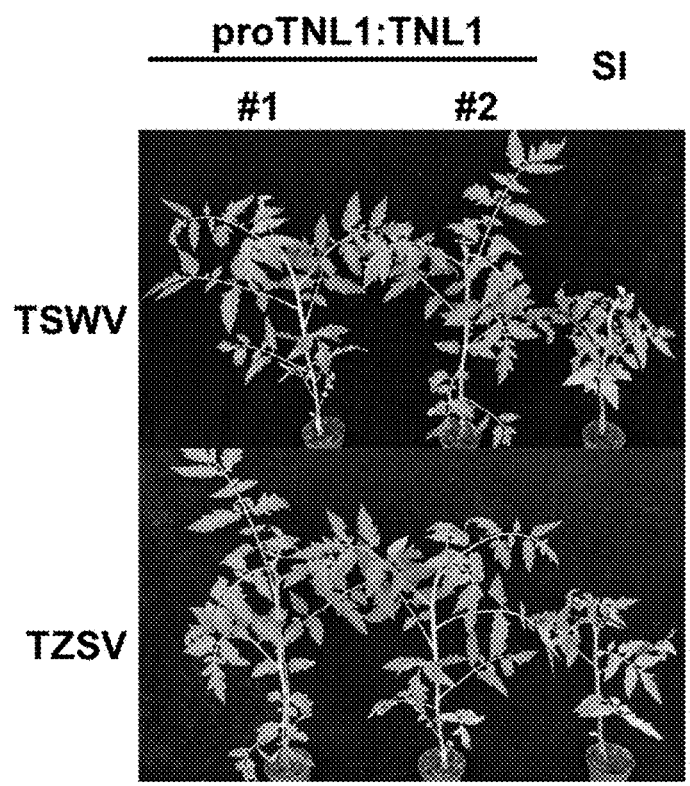
Figure 7:
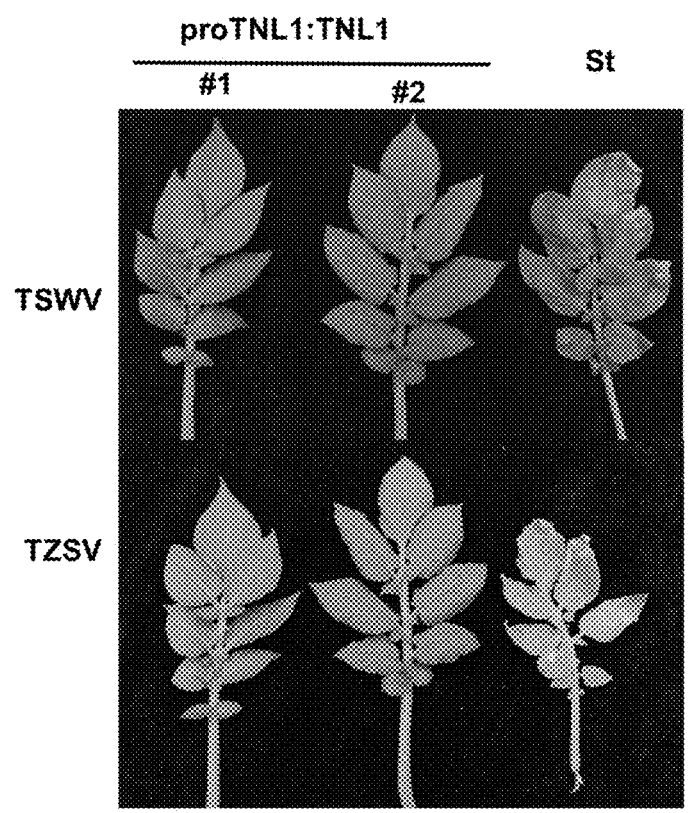

Virus inoculation results showed that different independent proTNL1:TNL1 transgenic plants in N. benthamiana (FIG. 5), tomato (FIG. 6) and potato (FIG. 7) showed resistance to TSWV and TZSV. No virus was detected in the systemic leaves of all the transgenic plants. As a control, non-transgenic N. benthamiana, tomato and potato were highly susceptible to TSWV and TZSV.

Seq Id No: 1-10

TNL1 gene

>SEQ ID NO: 1

ATGGATACTCAATTAGTTAGAGGAGAATCATCTACATCTTCTCACTTCTCTTATGAAGTAT

TCCTCAGTTTTAGAGGTGAAGACACCCGAAAAACATTCACTGCTCATCTTTTTTCCAAATT

GTCTGATGTTGGAGTTAATACCTTCATTGACGATGAGGAATTGAGAAAGGGTGACGTGATT

TCAAGAGAATTAGAGAAAGCAATTGAAGAGTCTAGAATTTCCATTATTGTTTTCTCAAGAA

ATTATGCTTCCTCTAGTTGGTGTCTAAATGAACTAGTTAAGATTCTTGAATGCAAAGAGAA

ATTTAAGCAGATGGTTTTGCCTATTTTCTATGATGTTGATCCTTCTGAGGTACGAAAACAA

ACTGGGTTATTTGGTGAAGCTTTGGCTAAACACAAGGAACGACCATTTGGAGCTCAAAGGG

TGGAGAAATGGAGAGCTGCACTTACTGAAGCTGCAAATCTATCTGGATGGGATTTGCAAAA

TGTGGACGGGTACATTTTCTTGATTCAACTATAGAATTTCATTTGTTATTTGTTCAATTGT

TTTATAGGATGTGATACTAACGGTTAAAAAGAGTTTAGGTTTTATACATTGATATTATTG

AAATATATTTAAAATTTATTGGAATTAAATCCGTAAAATAATTTGGATTATATTTTAAATT

CAAGATATATCCGTTCAAATAAATTTGTATATGTTAAATTATTTCTTAAAATATCCTATAT

GACGTCGTAAGTTATCTATTTTGTCGCTTAGATTCATCCCACTTTGTTATGTCTTGCTATC

GATTTTGATTTCTCCGTCAAATAATTTCAAATATCAAAGTTTTATTTACTGGAGTAGTGTT

TCTTTTAATTTTTTGATTTTGCTAAAAAATTTGTAGGCATGAATCAAAGTTTATTGAAAAA

ATAATACAGCAAGTCCTACAAGTGGTCAACCAGACACCTCTAGATGTTGCTTGGCACCCAG

TTGGAGTAGATTCTCGTGTCAAAGATATAGAGTTATTATTGCAAAATGAATGTGAAGATGA

AGTTCGAATGATTGGTATTCACGGAGTTGGTGGCATAGGGAAAACAACTCTAGCAAAAGCT

ATCTACAATCGAATGTTTCGACTCTTCGATAGTAGTTGCTTCCTTTCAGATGTTAGATCAG

AAGCTGAAGAATTTGGTCTTGTCAAGCTACAAGAGAAACTTCTTCGACAAATTCTCAAAAC

TGAGGACATCAAAGTTGGCAGTGTTGCTCAAGGCATCAATCTAATCAAAGCAAGACTCGGG

TCAAAGAAGGTTCTAATTGTTCTTGATGACGTGGACCACAGAAACCAATTAGAATCCTTAA

CAAGAGAAAGAAGTTGGTTTGGTTCGGGTAGTTTAATAATCACTACCACCCGAGACAAGCG

ATTGCTATGCCGGTTTGGAGAAAAAGAGAGATATGAGGCCAAACTATTAAATGACAATGAA

-continued

```
GCTATGTTACTTTTTTGTTGGCATGCTTTTGATAGTCATTTTCCACCAGAAGATTATGTTA
ATTTGGCACGAGACATAATCAGATATTCAGGTAGGCTACCATTAGCTCTTGTGACATTGGG
GTTACATTTACAAGGAAGTTCTATAGAAGAATGGGGATATGAATTCGAAAAACTAAAATCA
ATTCCTCATTGTGATATCCAAAAGATTCTCAAGATAAGCTTTGATGGACTTGATGATGAAA
CACAGACTGTTTTCCTCGATATTGCATGCATCTTCCATGGGTTTGATGAGCGTAAAGTTAA
TAAAATATTAAATGCATGTGGCTTTCATGCTAAAAGTGCAATTACAACTTTAGTCCAAAAA
CACTTGCTCCAAAGATCTTGGGATTATTTGGTGATGCATGATCTAGTGCGAGATATGGGAA
GATATATTGTTCGCATGGAATCAGCTCGAGACCCTGGAAAACGGAGTAGATTGTTCATCCC
TCAAGAAGTCTGTGATGTTCTACAAGGAAATAAAGTTAGTAAATCTTTTATCCTTTATCTT
GGTTATAATATATTTTTCAATTTAATTGTTTATTGCTTATAATGTTGTCATCATAATATAT
AAGTGAATTCATTTTGTGCTTCGTCTATGGTTAGTTTTGTAGTTTTTTGTCAACCATTGTA
AACTAGAAGTTACATTTGCTAAATTCTTAACTCACACCCAAGGCGGAAAAAAATCACCTAT
TTAACAATTATCCTAATTTGGTGATGCATATTTCTTATAAAATTCTTATAACTAACATGCT
AATGGGCATCCACCATAGTATCTCCATGATTAGTTATTCAAAGATATTTGACTTTACTTAA
CTAAATGCAGAAATTAAGCTTGCTCGAAGAAATCAGGCATGTGAACGTTTGGAAATTGTTG
AATCCGTACATATGTGAAACATTATTTCTAGAACAATATGTACAAAGTATTCTTTCAAATA
TATTCAAATATATCTTCTATCTTCTAGTGCTATTATCATGGTTCCCATTCACACAGTATCA
ATATGTTCTCTTTATTCATTTTTTTCCCTTTGATATTATCATGTGAACTTAGTGAATGCTG
CTAGCCGGGTTTGAAAGGCTCTCATCTTAGCTTTTTGAACAATTTTAAATTTGTTTAACAT
CCTCTAATGTGTAAGTTCATTTTTGTTGATACATGGTGTATTCTCTTTGTTTGTCCACCAA
TTTGTATAAAGCATTTTTCTCGCGTAATTTCTGATATTTAACATGTGCTTAAGTTACTTTT
TTTTTTACTGAGCTGCAGGGTTCCAAAAATGTAGAAGTACTGAAGGTAGATCCAGGGACAT
TAAAGGGAGTGAACTTGAGCACCAAAGCATTTGAGAAAATGAAGAATCTTAGGGTGCTCAT
AATCGAGGAGTTACATATTAGTGGAGATTTTGGGCTGTTGTCCAAGAAGCTCAAATGGTTG
TCTTGGCAAAACTGTCCTTTAAAATATATACCATCAAATTTTCCAGCTGAGAATCTTGTAG
TTCTAGATATGCGGAAGAGTGTGATATCGAGGAATTTCAATTGAATTTGCAGGTTTGTTACTC
AATTTTACAATTTCATGTGTACTGTTATTGCCACTGAGTGAAAGAAAATGTTAATTGAAAC
TATATTTGGTTTACTTTTAGTGTTGTAGAAGTTTGAAGAAGCTGAATCTCTCTAATTGCAA
GCAACTCAGAAGCACTCCAAACTTCAATGGTTCACTGAGTCTTGAGATTTTGAATCTCGAT
GGTTGCCTAAGTCTGAGGGAGATCCATCCATCAATAGGGAATTTGTCCAGACTAATTAAAC
TATATATGCGTGGTTGCGAAAAACTTACGGATCTTCCTAGCAGCATTTGCCAGCTAAAATC
CCTTGATTACTTGGACATTGATGGCTGCTCATTTATAAAAACACTGCCAGATAACCTTGGA
GATATGAAAAGTCTAAGACATCTTTCTGCATCTTATACGGGTATAAAACAATTGCCTAGAT
CTGTTGAAATGCTAAGAAATCTTAAAATATTGGAAGTGGGAAATCGAATGTTTGGGACCAA
TATGAGTATTTATGGAAGAGGAGTCCATCAGATACAATATTCCTTGTCAACTTTTGTATCC
GATTTGAGACTTACATACTGTAATTTGTCCGAGGCTGATATTCCTAGGGATATTGGGAGCT
CATCCTCCTTAGAACTTTTAGATTTGAGTGGCAACAGTTTCCATTGTCTACCTTTTGATTT
TTCTAAGTTACGATTCTTGAAGGGGTTGTATTTGATTGACTGTGAGAACCTTCAAACACTC
CCGTCAATATCAAATTTAGAGAAACTTGAAAGAATTGAACTTCAAAATTGCCAAAAATTGG
TCAAGATTAGAGAGTTGGACAACCTCCCCTTCTATATGGTCGATCGACATGAGGAATTGTAG
```

-continued
```
TTGTCTGCAGAATCCATTCAATGAAAGCTTCTTCAGTGCACCTGCTCTATCATTTCCATCT

AGATTAGTCTCTCTCTCTCTCTCCTATCATATTAATGATCTTGAGTCTTTGTCCGATGC

AGCATGAAATAGAAATTAGCATTTATCTGGAATGCAAAGAGATTCCAGAATGGTGCAGGAA

TCGAGTAACAACTTCATCTATGTGTTTGACTATGCCTACACATAATAAGGAGTATAACTTC

TTAGGAATGGTTCTCTGGTTAGTTTCCGACTTCTCTCATCCATGCTTGTGGATTAGTATTG

CCCATAAACAGCCTTCAATTATGGTGTGGAGTAGTGTTTATACAACACTTGGTACACTTGA

TGGACACACAGAAGTATCATGTGTACGTTACATATCTTACTTACATAGAGCTTTTGATGGC

CAGATGATCAAAGGCGGGGAAACGATAGAAGCGTGGTCTGAAGACTCTACAATAAAGAAGA

TAGGGATCCATCTGTTATATTTGGACGAATATGGTAAAGTTATATCTTTGCCGGGAGACGT

GGATCATTCTTATTCTAAGTACCCAAAAAGAGTTTCAACAGTCTTATCAACTCCTCCTTAT

AAAAGAGCAAAGTTC
```
Coding region of TNL1 cDNA
>SEQ ID NO: 2
```
ATGGATACTCAATTAGTTAGAGGAGAATCATCTACATCTTCTCACTTCTCTTATGAAGTAT

TCCTCAGTTTTAGAGGTGAAGACACCCGAAAAACATTCACTGCTCATCTTTTTTCCAAATT

GTCTGATGTTGGAGTTAATACCTTCATTGACGATGAGGAATTGAGAAAGGGTGACGTGATT

TCAAGAGAATTAGAGAAAGCAATTGAAGAGTCTAGAATTTCCATTATTGTTTTCTCAAGAA

ATTATGCTTCCTCTAGTTGGTGTCTAAATGAACTAGTTAAGATTCTTGAATGCAAAGAGAA

ATTTAAGCAGATGGTTTTGCCTATTTTCTATGATGTTGATCCTTCTGAGGTACGAAAACAA

ACTGGGTTATTTGGTGAAGCTTTGGCTAAACACAAGGAACGACCATTTGGAGCTCAAAGGG

TGGAGAAATGGAGAGCTGCACTTACTGAAGCTGCAAATCTATCTGGATGGGATTTGCAAAA

TGTGGACGGGCATGAATCAAAGTTTATTGAAAAAATAATACAGCAAGTCCTACAAGTGGTC

AACCAGACACCTCTAGATGTTGCTTGGCACCCAGTTGGAGTAGATTCTCGTGTCAAAGATA

TAGAGTTATTATTGCAAAATGAATGTGAAGATGAAGTTCGAATGATTGGTATTCACGGAGT

TGGTGGCATAGGGAAAACAACTCTAGCAAAAGCTATCTACAATCGAATGTTTCGACTCTTC

GATAGTAGTTGCTTCCTTTCAGATGTTAGATCAGAAGCTGAAGAATTTGGTCTTGTCAAGC

TACAAGAGAAACTTCTTCGACAAATTCTCAAAACTGAGGACATCAAAGTTGGCAGTGTTGC

TCAAGGCATCAATCTAATCAAAGCAAGACTCGGGTCAAAGAAGGTTCTAATTGTTCTTGAT

GACGTGGACCACAGAAACCAATTAGAATCCTTAACAAGAGAAAGAAGTTGGTTTGGTTCGG

GTAGTTTAATAATCACTACCACCCGAGACAAGCGATTGCTATGCCGGTTTGGAGAAAAAGA

GAGATATGAGGCCAAACTATTAAATGACAATGAAGCTATGTTACTTTTTTGTTGGCATGCT

TTTGATAGTCATTTTCCACCAGAAGATTATGTTAATTTGGCACGAGACATAATCAGATATT

CAGGTAGGCTACCATTAGCTCTTGTGACATTGGGGTTACATTTACAAGGAAGTTCTATAGA

AGAATGGGGATATGAATTCGAAAAACTAAAATCAATTCCTCATTGTGATATCCAAAAGATT

CTCAAGATAAGCTTTGATGGACTTGATGATGAAACACAGACTGTTTTCCTCGATATTGCAT

GCATCTTCCATGGGTTTGATGAGCGTAAAGTTAATAAAATATTAAATGCATGTGGCTTTCA

TGCTAAAAGTGCAATTACAACTTTAGTCCAAAAACACTTGCTCCAAAGATCTTGGGATTAT

TTGGTGATGCATGATCTAGTGCGAGATATGGGAAGATATATTGTTCGCATGGAATCAGCTC

GAGACCCTGGAAAACGGAGTAGATTGTTCATCCCTCAAGAAGTCTGTGATGTTCTACAAGG

AAATAAAGGTTCCAAAAATGTAGAAGTACTGAAGGTAGATCCAGGGACATTAAAGGGAGTG

AACTTGAGCACCAAAGCATTTGAGAAAATGAAGAATCTTAGGGTGCTCATAATCGAGGAGT

TACATATTAGTGGAGATTTTGGGCTGTTGTCCAAGAAGCTCAAATGGTTGTCTTGGCAAAA
```

-continued

```
CTGTCCTTTAAAATATATACCATCAAATTTTCCAGCTGAGAATCTTGTAGTTCTAGATATG
CGGAAGAGTGATATCGAGGAATTTCAATTGAATTTGCAGTGTTGTAGAAGTTTGAAGAAGC
TGAATCTCTCTAATTGCAAGCAACTCAGAAGCACTCCAAACTTCAATGGTTCACTGAGTCT
TGAGATTTTGAATCTCGATGGTTGCCTAAGTCTGAGGGAGATCCATCCATCAATAGGGAAT
TTGTCCAGACTAATTAAACTATATATGCGTGGTTGCGAAAAACTTACGGATCTTCCTAGCA
GCATTTGCCAGCTAAAATCCCTTGATTACTTGGACATTGATGGCTGCTCATTTATAAAAC
ACTGCCAGATAACCTTGGAGATATGAAAAGTCTAAGACATCTTTCTGCATCTTATACGGGT
ATAAAACAATTGCCTAGATCTGTTGAAATGCTAAGAAATCTTAAAATATTGGAAGTGGGAA
ATCGAATGTTTGGGACCAATATGAGTATTTATGGAAGAGGAGTCCATCAGATACAATATTC
CTTGTCAACTTTTGTATCCGATTTGAGACTTACATACTGTAATTTGTCCGAGGCTGATATT
CCTAGGGATATTGGGAGCTCATCCTCCTTAGAACTTTTAGATTTGAGTGGCAACAGTTTCC
ATTGTCTACCTTTTGATTTTTCTAAGTTACGATTCTTGAAGGGGTTGTATTTGATTGACTG
TGAGAACCTTCAAACACTCCCGTCAATATCAAATTTAGAGAAACTTGAAAGAATTGAACTT
CAAAATTGCCAAAAATTGGTCAAGATTAGAGAGTTGGACAACCTCCCTTCTATATGGTCGA
TCGACATGAGGAATTGTAGTTGTCTGCAGAATCCATTCAATGAAAGCTTCTTCAGTGCACC
TGCTCTATCATTTCCATCTAGATTAGTCTCTCTCTCTCTCTCCTATCATATTAATGATC
TTGAGTCTTTGTCCGATGCAGCATGAAATAGAAATTAGCATTTATCTGGAATGCAAAGAGA
TTCCAGAATGGTGCAGGAATCGAGTAACAACTTCATCTATGTGTTTGACTATGCCTACACA
TAATAAGGAGTATAACTTCTTAGGAATGGTTCTCTGGTTAGTTTCCGACTTCTCTCATCCA
TGCTTGTGGATTAGTATTGCCCATAAACAGCCTTCAATTATGGTGTGGAGTAGTGTTTATA
CAACACTTGGTACACTTGATGGACACACAGAAGTATCATGTGTACGTTACATATCTTACTT
ACATAGAGCTTTTGATGGCCAGATGATCAAAGGCGGGGAAACGATAGAAGCGTGGTCTGAA
GACTCTACAATAAAGAAGATAGGGATCCATCTGTTATATTTGGACGAATATGGTAAAGTTA
TATCTTTGCCGGGAGACGTGGATCATTCTTATTCTAAGTACCCAAAAAGAGTTTCAACAGT
CTTATCAACTCCTCCTTATAAAAGAGCAAAGTTC
```

TNL1 protein
>SEQ ID NO: 3

```
MDTQLVRGESSTSSHFSYEVFLSFRGEDTRKTFTAHLFSKLSDVGVNTFIDDEELRKGDVI
SRELEKAIEESRISIIVFSRNYASSSWCLNELVKILECKEKFKQMVLPIFYDVDPSEVRKQ
TGLFGEALAKHKERPFGAQRVEKWRAALTEAANLSGWDLQNVDGHESKFIEKIIQQVLQVV
NQTPLDVAWHPVGVDSRVKDIELLLQNECEDEVRMIGIHGVGGIGKTTLAKAIYNRMFRLF
DSSCFLSDVRSEAEEFGLVKLQEKLLRQILKTEDIKVGSVAQGINLIKARLGSKKVLIVLD
DVDHRNQLESLTRERSWFGSGSLIITTTRDKRLLCRFGEKERYEAKLLNDNEAMLLFCWHA
FDSHFPPEDYVNLARDIIRYSGRLPLALVTLGLHLQGSSIEEWGYEFEKLKSIPHCDIQKI
LKISFDGLDDETQTVFLDIACIFHGFDERKVNKILNACGFHAKSAITTLVQKHLLQRSWDY
LVMHDLVRDMGRYIVRMESARDPGKRSRLFIPQEVCDVLQGNKGSKNVEVLKVDPGTLKGV
NLSTKAFEKMKNLRVLIIEELHISGDFGLLSKKLKWLSWQNCPLKYIPSNFPAENLVVLDM
RKSDIEEFQLNLQCCRSLKKLNLSNCKQLRSTPNFNGSLSLEILNLDGCLSLREIHPSIGN
LSRLIKLYMRGCEKLTDLPSSICQLKSLDYLDIDGCSFIKTLPDNLGDMKSLRHLSASYTG
IKQLPRSVEMLRNLKILEVGNRMFGTNMSIYGRGVHQIQYSLSTFVSDLRLTYCNLSEADI
PRDIGSSSSLELLDLSGNSFHCLPFDFSKLRFLKGLYLIDCENLQTLPSISNLEKLERIEL
```

-continued

QNCQKLVKIRELDNLPSIWSIDMRNCSCLQNPFNESFFSAPALSFPSRLVSLSLSPIILMI

LSLCPMQHEIEISIYLECKEIPEWCRNRVTTSSMCLTMPTHNKEYNFLGMVLWLVSDFSHP

CLWISIAHKQPSIMVWSSVYTTLGTLDGHTEVSCVRYISYLHRAFDGQMIKGGETIEAWSE

DSTIKKIGIHLLYLDEYGKVISLPGDVDHSYSKYPKRVSTVLSTPPYKRAKF

Native promoter of TNL1 gene

>SEQ ID NO: 4

AGCCAAACACCAATTCTTTCCCTTTACTTTCCATTTTAAATTTCATGTTTGTAAAAATATA

TCACATAAATTGAGACAGATGAAATAAATGAATTTTGACCAATTTTTTCAATTCACTTGCC

GATAATACAAAAGGGATTAAAAAAAAAAGACTTTTGAGATGCAAAAGAAAAGAATCCCGCA

AACAACTTGTAGAGTATTTCTACCCAATACGAAAAAGGGAAATTACCAGCTATGTCCATTT

AGAAGTATCCCATTACAAAAATTGGCCAATTAATAAAATATTACTAATATTAGCCAAAATG

GCCAATTAACTATTTGTAGCAAAAAAATATCAAATTTTTACTTTCTTTTGAGTGGGTGCTA

TTAGAATAGATTGGGTATATCTTAAGGAGCTTGAATCTCAGTTTTGGGATGATTTGGTGAA

GTTTTGACGTGGTTTAAATTGAAAATTCGAAGTAAAAACTGAATATGAAAAAAAATGATAC

ATGTATTACACTGTGTATCACATATGTATCATATTTGTATCGATTGTGTATCACATGTATA

TCTGTGTGTGAGATACATGTGTGATACATGTTTGATACATGTGTCACAGAAGAATTTTTTG

ACATCGATTTAATTATGAATTTTGATATAAAACCAGTCCAAATCACCTCCAATCTTCATCA

AATTTTGTATATTGACTTATCTATATGTTTTCAATGAATTTCGACTATACCCATTAAAAAA

ATTCCTTGTTTATTTCGATTTTGGAATATTGGCTAGAGGTTGGTAAGTTGAAACTTATATG

GGACATTTTGTAAGTTTCCCTACGAAAAAATCCAAAAGTAATTTCCTAGAACAACTTACA

AACTGTGAACTATACTGCATGCATTTATACTTCCTTTTCAGTAACTCTTGTTTAATCTTAT

TCGATTAAATTTATGAATATTATTTCAGTTTGTAATGGCCTAATATTTTAAAAGGAATTTG

CAAAATTCTTATTTCATCACTATACAAGAAAATACACTCAAGGGTCATATAGGATCTGTGA

ATTCAGAGGTGGATCCGGGATTTGATGGTTATGAGTGTCATCGCTTTTAATGCATTTTGTC

AGTTTGATCCATTTTGAATTAATTTGGTTCGATCTATTTTAATTTTGTAGATTTACAATAT

GAGTTACAGCGTGAACTTTATTTACACTATAAGACTAAGAGCCCGTTTGGCTTAGCTGATT

TAGAGTAGCTGATAAGCATTAGGTACTGAAAAGCACTTTTAAGTGCTGAAACTGATTTAAA

AAATAAGCAGTTACGTGTTTGGATAAAAGTGCTGAAATTAATAATATGCAGCTGAAGAACT

GGGTATACGAAGAGTTTTGTTTTAAAAAGAAGTATTTTAGGGATAGAATAGTAAATATTTT

GGTCAAACTTAAAGTGCTTATAAGCTGAAATTTGATAAGTTGGGGGAGACCAACTTATGAC

TTTTGGCTTATTTTTGGCTTATAAGCACTTAACTTATAAGCATTTTAATTTTACCAAACG

CGTAGATAAGCCAAAAAGTGCTTATAAGTCAGTTTGACCAGCTTATAAGCTTAGCCAAACA

CCCTCTAAGAGTCTGTTTGGAAAAGGTGTAATTATTTTAAGTGATTTTTAAAATTATCATT

GCCAAAAACTAATTACGAAAAAAGTACAACAAAAAAAAAAAAGAGTATAGGAAAAGGTGAA

ATTATGGCGAAAGTGGAAATCCACAAAATTTCATGGCATTCCGTTTAATTTCTTTTAAGGG

TTGACTTGACTTCCACAAAGGAAGACCTCTGCTTATATGTAGCTCTGCTACTTTCCCTTTA

CTGAAAAATTCATTCCTTAATTCTTGGATTCTCATCAACCCTTAA

TNL2 gene

>SEQ ID NO: 5

ATGGATACTCAATTAGTTAGAGTAGAATCATCTACATCTTCTCACTTCTCTTATGAAGTAT

TCCTCAGTTTTAGAGGTGAAGACATCCGAAAAACATTCACTGGTCATCTTTATTCCAAATT

AGATAATGTTGGAGTTAAAACCTTCATCGACGACGAGGAATTGAGAAAGGGTGACGTGATT

TCAAGTAAACTAGAGAAAGCAATTGAAGAGTCACGAATTTCCATTATTGTTTTCTCAAGAA

-continued

```
ATTATGCTTCCTCTAGTTGGTGTCTAAATGAACTAGTTAAAATTCTTGAATGCAAAGAGAA
ATTAAAGCATATGGTTTTTCCTATTTTCTATGATGTTGATCCTTCTGAGGTACGAAAACAA
ACTGGGTTATTTGGTGAAGCTTTGGCTAAACACAAGGAACGACCATTTGGAGCTCAAATGG
TGGAGAAATGGAGAGCTGCACTTACTGAAGCTGCAAATTTTTCTGGATGGGATTTGCAAAA
TGTTGCTGACGGGTACATATTCTTGATTCAACTATAGAATTTCAGTTGTTATTAGTTCAAT
TGTTTTATAGGATGTGATACTAACGGTTAAAAAAGAGTTTAGGTTTTATACATTGATATTA
TTAAAATATATTTAAAATTTATCGGAATTAAATCCGTAAAATAATTTGGATTATATTTTAA
ATTCAAGATATATCAGTTCAAATAAATTTGTATATGTTAAATTATTTCTTAAAATATCCTA
TATGACGTCGTAAGTTATCTATTTTGTTGCTTAGATTCATCCCACTTTGTTATGTCTTGCT
ATCAATTTTGATTTCTCCGTCAAATAATTTCAAATATCAAAGTTTTATTTACTGGAGTAGT
GTTTCTTTTAATTTTTTGATTTTGCTAAAAAATTTGTAGGCATGAATCAAAGTTTATTGAA
AAGATTATACAGCAAGTCCTACAAGTGGTCAACCAGACACCTCTAGATGTTGCTTGGCACC
CAGTTGGAGTAGATTCTTCTGTCAAAGATATAGAGTTATTATTGCAAATGAATGTGAAGA
TGAAGTTCGAATGATTGGTATTCACGGAGTTGGTGGCATAGGGAAAACAACTCTGGCAAAA
GCTATGTACAATCGAATGTTTCGACTCTTCCATAGTAGTTGCTTCCTTTCAGATGTTAGAT
CAGAAGCTGAAGAATTTGGTCTTGTCAAGCTACAAGAGAAACTTCTTCAACAAGTACTCAA
AACTAAGGACATCAAAGTTGGCAGTGTTGCTCAAGGCATCAATCTAATCAAAGCAAGACTG
GGGTCAAAGAAGGTTCTGATTGTTCTTGATGATGTGGACCATAAAAGACAGTTAGAAGCCT
TAACAAGAGAAAGAGGTTGGTTTGGTTCGGGTAGTTTAATAATCATTACCACCCGAGACGA
GCAATTGCTATGTCGGCTTGGAGAAAAAGAGAGATATGAGGCTGAACTATTAAATGACAAT
GAAGCTCAACAACTTTTCAGTTGTCATGCTTTTGACAGTCCTTCTCCACCACTAGAATATG
TTAGTTTGGCACATGACGTAATCGAATATTCAGGTAGGCTACCATTAGCTCTTGTGACATT
GGCGTCACATTTGCAAGGAAGTTTTGTAGAAGAATGGGGATATGAATTCGAAAAACTAAGA
GCAATACCTCATATTGATATCCAAAAGATTCTCAAGATAAGCTTTGATGGACTTGATGGTG
ATACACAAACTGTGTTCCTTGATATTGCGTGCGCCTTCCATGGGTTTTATGAGCATGAAGT
TACAGAAATATTAAATGCATGTGGCTTTCATGCTAAAAGTGCAATTGCAACTTTAGTCCGA
AAACACTTGCTCCAAGGATCTCCGTGTCGTTTGAAGATGCATGATCTAGTGCAGATATGG
GAAGAGAAATTGTTCGCATGGAATCAGCTCGAGAACCTGGAAAACGGAGTAGATTGTTCAT
CCCTCAAGAAGTTCGTAATGTTCTACAAGGAAATGAAGTCAGTAAATCCCTCATCATTATC
TTGGTTATATATTTTTTCAATTAAATTGTTTCTTACTTATAATTTCTATTGTCATCATAAG
AAATCATTTCTGCTTCGTCTCTGGTTAGTAAGTATTTTGTAGTTGTTTGTCAATCATTGTG
AACTAGAAATGACATTTGCTAAATTCTTAACTAACACCAAAGGCAAAAACAATAATAAAAA
TCACCTATTTAATAATTATCCAAATTTGGTGATGCATATTTCTTATTAAATTCTTATAACT
AGCATGCTTATCGGCATAAACCATAGTATCTCCGTGATTAGTTATTCAAAGATATTTGAGT
TTACTTAACTAAATGCGGAAATTAAACTTGCTCGAAGAAATCAAGCATGCGACCATTTGAA
AACTGTTGAATAGGTACATATGTGAAACATTATTTCTAGAACGATATATACAAAATGTTCT
TTTAAATATATTCAAATATATATTCGATCTTCATTTGGCGCTATTATCAAGTTTCTAGATG
CAATTTGTTCTCTTTATTCATCATTTTTTTCCTTTGATATTATCATGTGAACTTATTGAA
TGCTGCTAGCCAATTTTGGAAGGCTCTCATCTTAGCTTGAGCAATTTTAAATTTGTTTAAC
ATCCTCTAGGTTCAATTTTGTTGATACATGGTGTATTCTCTTTGTTTGTCCACCAATTTTT
```

-continued

```
ATAAAGCATTTTCTCGCTTAATTTCTTGGACTTAACATGAGCTTAAGTTACTTTTCTTTTT

ACTGAGCTGCAGGGTTCCGAAAATGTAGAAGTACTGAAGGTAGATCGAGGGACATTAAACG

GAGTGAACTTGAGCACCAAAGCATTTGAGCGAATGAAGAATCTTAGGGTGCTTATAATCAA

TGACGAGTTATATATTAGTGGAGATTTTGGGATGTTGTCCAATAAGCTTAGATGGTTGTCT

TGGAAAGAATGTCCTTTAAAATGTATACCATCAAATTTTCCCGCTGAGAATCTTGTAGTTC

TAGATATGCGGAAGAGTGATATCGAGGAATTTCAATTGAATTTGCAGGTTTGCTACTCAAT

TTTACAATTTCATGTGTACTGTTATTGCCACTGAGTGAAAGAAAATGTTAATTGAAACTAT

ATTTGGTTTACTTTTAGTGTTGTAGAAGTTTGAAGAAGCTGAATCTCTCTAAGTGCAAGCA

ACTCAGAAGCACTCCAAACTTCAATGGTTCACTGAGTCTGGAGATTTTGAATCTCCATGGT

TGCCTAAGTCTGAGGGAGATCCATCCATCAATAGGGAATTTGTCCAGACTAATTAAACTAT

ATATGCGTGGTTGCGAAAAACTTACGGATCTTCCTAGCAGCATATGCCAGCTAAAATCCCT

TGATCACTTGGACATTGATGGCTGCTCATTTATAAAAACACTGCCAGATAACCTTGGAGAT

ATGAAAAGCCTAAGACATCTTTATGCATCTGGTACAGGTATAAAACAATTGTCCAGATCTA

TTGAAATGCTAAGAAATCTTGAAACTTTGAGAGTGGAAGGTGAAAAGTTAGAGGCCAAAAG

GAGTATTTCTGGAAGAGGAGTCCATCAGATACAATATTCCTTGTCAACTTTTGTATCCGAT

TTGAGACTTACATACTGTAATTTGTCCGAGGCTGATATTCCTAGGGATATTGGGAGCTTAT

CCTCCTTTGAACTTTTAGATTTGAGTGGTAACAGTTTTAATTGTCTACCTTTTGATTTTTC

TAAGTTACGATTGCTGAAGGTGTTGTGTTTGAATGATTGTGAGAATCTTCAAACACTCCAG

TCAGTATCAAATTTAGAGAATCTTGAAATTCTTGATCTTGAAAATTGCGAAAAATTGGTCA

AGATTACAGAGTTGGACAACCTCCCTTCTATATGGTGGATCAACATGATTAATTGTAGTTG

TCTGCAGAATCCATTCAATGAAGGCTTCTTTAGTGCACCTGCTCTCTCTAGAAAAGATCGA

GATATGTTTAGAAAAATGGTTAGTCTGTCTCTTTCTCTCTCTCTGCTATCATATTAATG

ATCTTGAGTCTCTGTCTGATGCAGTGTGAAATAGAAATTTATCTCGAATGCCAAGAGATTC

TAGAATGGTGCAGGAATCAAGTAACAACTTCATCTATGTGTTTGACTATGCCGACACATAA

TAAGGAGTATAACTTCTTAGGAATGGTTCTCTGGCTTGTTTTCGACTTCTCTTTGGATGTA

GCCTCTCTTCCATGCTTGTGGATTAGTATTGCCCATAAACAGCCTTCACTTATGGGGTGGC

GTGGTGTTCTTACAACACTTGAAGTATCATGTGTAAGTTACATATCTTACTTACATAGAGC

TTTTGATGGCCAGATGATCAAAGGTGGGGAAAGGATAGAAGTGTGGTCTGAGCACATTACA

ATAAAGAAGATAGGGATCCATCTGTTATATTTGGACGAATATGGTAAAGTTATATCTTTGC

CGGGAGACGTGGATCATTCTTATTCTAAGTACCCAAAAAGAGTTTCAACAGGCTTATTATC

AACTCCTCCTTATAAAAGAGCAAAGTTCTGAGTCAAGATAATTTTCCTTTAGAGCTAATCA

AATTGTATTTATATTACACTATTAATGTGTAGTTGATCAGTTAATTTTTAATTGA
```

Coding region of TNL2 cDNA

>SEQ ID NO: 6

```
ATGGATACTCAATTAGTTAGAGTAGAATCATCTACATCTTCTCACTTCTCTTATGAAGTAT

TCCTCAGTTTTAGAGGTGAAGACATCCGAAAAACATTCACTGGTCATCTTTATTCCAAATT

AGATAATGTTGGAGTTAAAACCTTCATCGACGACGAGGAATTGAGAAAGGGTGACGTGATT

TCAAGTAAACTAGAGAAAGCAATTGAAGAGTCACGAATTTCCATTATTGTTTTCTCAAGAA

ATTATGCTTCCTCTAGTTGGTGTCTAAATGAACTAGTTAAAATTCTTGAATGCAAAGAGAA

ATTAAAGCATATGGTTTTTCCTATTTTCTATGATGTTGATCCTTCTGAGGTACGAAAACAA

ACTGGGTTATTTGGTGAAGCTTTGGCTAAACACAAGGAACGACCATTTGGAGCTCAAATGG

TGGAGAAATGGAGAGCTGCACTTACTGAAGCTGCAAATTTTTCTGGATGGGATTTGCAAAA
```

-continued

```
TGTTGCTGACGGGCATGAATCAAAGTTTATTGAAAAGATTATACAGCAAGTCCTACAAGTG

GTCAACCAGACACCTCTAGATGTTGCTTGGCACCCAGTTGGAGTAGATTCTTCTGTCAAAG

ATATAGAGTTATTATTGCAAAATGAATGTGAAGATGAAGTTCGAATGATTGGTATTCACGG

AGTTGGTGGCATAGGGAAAACAACTCTGGCAAAGCTATGTACAATCGAATGTTTCGACTC

TTCCATAGTAGTTGCTTCCTTTCAGATGTTAGATCAGAAGCTGAAGAATTTGGTCTTGTCA

AGCTACAAGAGAAACTTCTTCAACAAGTACTCAAAACTAAGGACATCAAAGTTGGCAGTGT

TGCTCAAGGCATCAATCTAATCAAAGCAAGACTGGGGTCAAAGAAGGTTCTGATTGTTCTT

GATGATGTGGACCATAAAAGACAGTTAGAAGCCTTAACAAGAGAAAGAGGTTGGTTTGGTT

CGGGTAGTTTAATAATCATTACCACCCGAGACGAGCAATTGCTATGTCGGCTTGGAGAAAA

AGAGAGATATGAGGCTGAACTATTAAATGACAATGAAGCTCAACAACTTTTCAGTTGTCAT

GCTTTTGACAGTCCTTCTCCACCACTAGAATATGTTAGTTTGGCACATGACGTAATCGAAT

ATTCAGGTAGGCTACCATTAGCTCTTGTGACATTGGCGTCACATTTGCAAGGAAGTTTTGT

AGAAGAATGGGGATATGAATTCGAAAAACTAAGAGCAATACCTCATATTGATATCCAAAAG

ATTCTCAAGATAAGCTTTGATGGACTTGATGGTGATACACAAACTGTGTTCCTTGATATTG

CGTGCGCCTTCCATGGGTTTTATGAGCATGAAGTTACAGAAATATTAAATGCATGTGGCTT

TCATGCTAAAAGTGCAATTGCAACTTTAGTCCGAAAACACTTGCTCCAAGGATCTCCGTGT

CGTTTGAAGATGCATGATCTAGTGCGAGATATGGGAAGAGAAATTGTTCGCATGGAATCAG

CTCGAGAACCTGGAAAACGGAGTAGATTGTTCATCCCTCAAGAAGTTCGTAATGTTCTACA

AGGAAATGAAGGTTCCGAAAATGTAGAAGTACTGAAGGTAGATCGAGGGACATTAAACGGA

GTGAACTTGAGCACCAAAGCATTTGAGCGAATGAAGAATCTTAGGGTGCTTATAATCAATG

ACGAGTTATATATTAGTGGAGATTTTGGGATGTTGTCCAATAAGCTTAGATGGTTGTCTTG

GAAAGAATGTCCTTTAAAATGTATACCATCAAATTTTCCCGCTGAGAATCTTGTAGTTCTA

GATATGCGGAAGAGTGATATCGAGGAATTTCAATTGAATTTGCAGATATGTTTAGAAAAAT

GGTTAGTCTGTCTCTTTCTCTCTCTCTGCTATCATATTAATGATCTTGAGTCTCTGTCT

GATGCAGTGTGAAATAGAAATTTATCTCGAATGCCAAGAGATTCTAGAATGGTGCAGGAAT

CAAGTAACAACTTCATCTATGTGTTTGACTATGCCGACACATAATAAGGAGTATAACTTCT

TAGGAATGGTTCTCTGGCTTGTTTTCGACTTCTCTTTGGATGTAGCCTCTCTTCCATGCTT

GTGGATTAGTATTGCCCATAAACAGCCTTCACTTATGGGGTGGCGTGGTGTTCTTACAACA

CTTGAAGTATCATGTGTAAGTTACATATCTTACTTACATAGAGCTTTTGATGGCCAGATGA

TCAAAGGTGGGGAAAGGATAGAAGTGTGGTCTGAGCACATTACAATAAAGAAGATAGGGAT

CCATCTGTTATATTTGGACGAATATGGTAAAGTTATATCTTTGCCGGGAGACGTGGATCAT

TCTTATTCTAAGTACCCAAAAAGAGTTTCAACAGGCTTATTATCAACTCCTCCTTATAAAA

GAGCAAAGTTCTGA
```

TNL2 protein

>SEQ ID NO: 7
MDTQLVRVESSTSSHFSYEVFLSFRGEDIRKTFTGHLYSKLDNVGVKTFIDDEELRKGDVI
SSKLEKAIEESRISIIVFSRNYASSSWCLNELVKILECKEKLKHMVFPIFYDVDPSEVRKQ
TGLFGEALAKHKERPFGAQMVEKWRAALTEAANFSGWDLQNVADGHESKFIEKIIQQVLQV
VNQTPLDVAWHPVGVDSSVKDIELLLQNECEDEVRMIGIHVGGIGKTTLAKAMYNRMFRL
FHSSCFLSDVRSEAEEFGLVKLQEKLLQQVLKTKDIKVGSVAQGINLIKARLGSKKVLIVL
DDVDHKRQLEALTRERGWFGSGSLIIITTRDEQLLCRLGEKERYEAELLNDNEAQQLFSCH

-continued

AFDSPSPPLEYVSLAHDVIEYSGRLPLALVTLASHLQGSFVEEWGYEFEKLRAIPHIDIQK

ILKISFDGLDGDTQTVFLDIACAFHGFYEHEVTEILNACGFHAKSAIATLVRKHLLQGSPC

RLKMHDLVRDMGREIVRMESAREPGKRSRLFIPQEVRNVLQGNEGSENVEVLKVDRGTLNG

VNLSTKAFERMKNLRVLIINDELYISGDFGMLSNKLRWLSWKECPLKCIPSNFPAENLVVL

DMRKSDIEEFQLNLQICLEKWLVCLFLSLSAIILMILSLCLMQCEIEIYLECQEILEWCRN

QVTTSSMCLTMPTHNKEYNFLGMVLWLVFDFSLDVASLPCLWISIAHKQPSLMGWRGVLTT

LEVSCVSYISYLHRAFDGQMIKGGERIEVWSEHITIKKIGIHLLYLDEYGKVISLPGDVDH

SYSKYPKRVSTGLLSTPPYKRAKF proTNL1:TNL1
>SEQ ID NO: 8
AGCCAAACACCAATTCTTTCCCTTTACTTTCCATTTTAAATTTCATGTTTGTAAAAATATA

TCACATAAATTGAGACAGATGAAATAAATGAATTTTGACCAATTTTTTCAATTCACTTGCC

GATAATACAAAAGGGATTAAAAAAAAAAGACTTTTGAGATGCAAAAGAAAAGAATCCCGCA

AACAACTTGTAGAGTATTTCTACCCAATACGAAAAAGGGAAATTACCAGCTATGTCCATTT

AGAAGTATCCCATTACAAAAATTGGCCAATTAATAAAATATTACTAATATTAGCCAAAATG

GCCAATTAACTATTTGTAGCAAAAAAATATCAAATTTTTACTTTCTTTTGAGTGGGTGCTA

TTAGAATAGATTGGGTATATCTTAAGGAGCTTGAATCTCAGTTTTGGGATGATTTGGTGAA

GTTTTGACGTGGTTTAAATTGAAAATTCGAAGTAAAAACTGAATATGAAAAAAAATGATAC

ATGTATTACACTGTGTATCACATATGTATCATATTTGTATCGATTGTGTATCACATGTATA

TCTGTGTGTGAGATACATGTGTGATACATGTTTGATACATGTGTCACAGAAGAATTTTTG

ACATCGATTTAATTATGAATTTTGATATAAAACCAGTCCAAATCACCTCCAATCTTCATCA

AATTTTGTATATTGACTTATCTATATGTTTTCAATGAATTTCGACTATACCCATTAAAAAA

ATTCCTTGTTTATTTCGATTTTGGAATATTGGCTAGAGGTTGGTAAGTTGAAACTTATATG

GGACATTTTGTAAGTTTCCCTACGAAAAAATCCAAAAGTAATTTCCTAGAACAACTTACA

AACTGTGAACTATACTGCATGCATTTATACTTCCTTTTCAGTAACTCTTGTTTAATCTTAT

TCGATTAAATTTATGAATATTATTTCAGTTTGTAATGGCCTAATATTTTAAAAGGAATTTG

CAAAATTCTTATTTCATCACTATACAAGAAAATACACTCAAGGGTCATATAGGATCTGTGA

ATTCAGAGGTGGATCCGGGATTTGATGGTTATGAGTGTCATCGCTTTTAATGCATTTTGTC

AGTTTGATCCATTTTGAATTAATTTGGTTCGATCTATTTTAATTTTGTAGATTTACAATAT

GAGTTACAGCGTGAACTTTATTTACACTATAAGACTAAGAGCCCGTTTGGCTTAGCTGATT

TAGAGTAGCTGATAAGCATTAGGTACTGAAAAGCACTTTTAAGTGCTGAAACTGATTTAAA

AAATAAGCAGTTACGTGTTTGGATAAAAGTGCTGAAATTAATAATATGCAGCTGAAGAACT

GGGTATACGAAGAGTTTTGTTTTAAAAAGAAGTATTTTAGGGATAGAATAGTAAATATTTT

GGTCAAACTTAAAGTGCTTATAAGCTGAAATTTGATAAGTTGGGGGAGACCAACTTATGAC

TTTTGGCTTATTTTTGGCTTATAAGCACTTAACTTATAAGCATTTTTAATTTTACCAAACG

CGTAGATAAGCCAAAAAGTGCTTATAAGTCAGTTTGACCAGCTTATAAGCTTAGCCAAACA

CCCTCTAAGAGTCTGTTTGGAAAAGGTGTAATTATTTTAAGTGATTTTTAAAATTATCATT

GCCAAAAACTAATTACGAAAAAGTACAACAAAAAAAAAAAGAGTATAGGAAAGGTGAA

ATTATGGCGAAAGTGGAAATCCACAAAATTTCATGGCATTCCGTTTAATTTCTTTTAAGGG

TTGACTTGACTTCCACAAAGGAAGACCTCTGCTTATATGTAGCTCTGCTACTTTCCCTTTA

CTGAAAAATTCATTCCTTAATTCTTGGATTCTCATCAACCCTTAAATGGATACTCAATTAG

TTAGAGGAGAATCATCTACATCTTCTCACTTCTCTTATGAAGTATTCCTCAGTTTTAGAGG

```
TGAAGACACCCGAAAAACATTCACTGCTCATCTTTTTTCCAAATTGTCTGATGTTGGAGTT

AATACCTTCATTGACGATGAGGAATTGAGAAAGGGTGACGTGATTTCAAGAGAATTAGAGA

AAGCAATTGAAGAGTCTAGAATTTCCATTATTGTTTTCTCAAGAAATTATGCTTCCTCTAG

TTGGTGTCTAAATGAACTAGTTAAGATTCTTGAATGCAAAGAGAAATTTAAGCAGATGGTT

TTGCCTATTTTCTATGATGTTGATCCTTCTGAGGTACGAAAACAAACTGGGTTATTTGGTG

AAGCTTTGGCTAAACACAAGGAACGACCATTTGGAGCTCAAAGGGTGGAGAAATGGAGAGC

TGCACTTACTGAAGCTGCAAATCTATCTGGATGGGATTTGCAAAATGTGGACGGGTACATT

TTCTTGATTCAACTATAGAATTTCATTTGTTATTTGTTCAATTGTTTTATAGGATGTGATA

CTAACGGTTAAAAAGAGTTTAGGTTTTATACATTGATATTATTGAAATATATTTAAAATT

TATTGGAATTAAATCCGTAAAATAATTTGGATTATATTTTAAATTCAAGATATATCCGTTC

AAATAAATTTGTATATGTTAAATTATTTCTTAAAATATCCTATATGACGTCGTAAGTTATC

TATTTTGTCGCTTAGATTCATCCCACTTTGTTATGTCTTGCTATCGATTTTGATTTCTCCG

TCAAATAATTTCAAATATCAAAGTTTTATTTACTGGAGTAGTGTTTCTTTTAATTTTTTGA

TTTTGCTAAAAAATTTGTAGGCATGAATCAAAGTTTATTGAAAAAATAATACAGCAAGTCC

TACAAGTGGTCAACCAGACACCTCTAGATGTTGCTTGGCACCCAGTTGGAGTAGATTCTCG

TGTCAAAGATATAGAGTTATTATTGCAAAATGAATGTGAAGATGAAGTTCGAATGATTGGT

ATTCACGGAGTTGGTGGCATAGGGAAAACAACTCTAGCAAAAGCTATCTACAATCGAATGT

TTCGACTCTTCGATAGTAGTTGCTTCCTTTCAGATGTTAGATCAGAAGCTGAAGAATTTGG

TCTTGTCAAGCTACAAGAGAAACTTCTTCGACAAATTCTCAAAACTGAGGACATCAAAGTT

GGCAGTGTTGCTCAAGGCATCAATCTAATCAAAGCAAGACTCGGGTCAAAGAAGGTTCTAA

TTGTTCTTGATGACGTGGACCACAGAAACCAATTAGAATCCTTAACAAGAGAAAGAAGTTG

GTTTGGTTCGGGTAGTTTAATAATCACTACCACCCGAGACAAGCGATTGCTATGCCGGTTT

GGAGAAAAGAGAGATATGAGGCCAAACTATTAAATGACAATGAAGCTATGTTACTTTTTT

GTTGGCATGCTTTTGATAGTCATTTTCCACCAGAAGATTATGTTAATTTGGCACGAGACAT

AATCAGATATTCAGGTAGGCTACCATTAGCTCTTGTGACATTGGGGTTACATTTACAAGGA

AGTTCTATAGAAGAATGGGGATATGAATTCGAAAAACTAAAATCAATTCCTCATTGTGATA

TCCAAAAGATTCTCAAGATAAGCTTTGATGGACTTGATGATGAAACACAGACTGTTTTCCT

CGATATTGCATGCATCTTCCATGGGTTTGATGAGCGTAAAGTTAATAAAATATTAAATGCA

TGTGGCTTTCATGCTAAAAGTGCAATTACAACTTTAGTCCAAAAACACTTGCTCCAAAGAT

CTTGGGATTATTTGGTGATGCATGATCTAGTGCGAGATATGGGAAGATATATTGTTCGCAT

GGAATCAGCTCGAGACCCTGGAAAACGGAGTAGATTGTTCATCCCTCAAGAAGTCTGTGAT

GTTCTACAAGGAAATAAAGTTAGTAAATCTTTTATCCTTTATCTTGGTTATAATATATTTT

TCAATTTAATTGTTTATTGCTTATAATGTTGTCATCATAATATATAAGTGAATTCATTTTG

TGCTTCGTCTATGGTTAGTTTTGTAGTTTTTTGTCAACCATTGTAAACTAGAAGTTACATT

TGCTAAATTCTTAACTCACACCCAAGGCGGAAAAAAATCACCTATTTAACAATTATCCTAA

TTTGGTGATGCATATTTCTTATAAAATTCTTATAACTAACATGCTAATGGGCATCCACCAT

AGTATCTCCATGATTAGTTATTCAAAGATATTTGACTTTACTTAACTAAATGCAGAAATTA

AGCTTGCTCGAAGAAATCAGGCATGTGAACGTTTGGAAATTGTTGAATCCGTACATATGTG

AAACATTATTTCTAGAACAATATGTACAAAGTATTCTTTCAAATATATTCAAATATATCTT

CTATCTTCTAGTGCTATTATCATGGTTCCCATTCACACAGTATCAATATGTTCTCTTTATT
```

```
CATTTTTTTCCCTTTGATATTATCATGTGAACTTAGTGAATGCTGCTAGCCGGGTTTGAAA

GGCTCTCATCTTAGCTTTTTGAACAATTTTAAATTTGTTTAACATCCTCTAATGTGTAAGT

TCATTTTTGTTGATACATGGTGTATTCTCTTTGTTTGTCCACCAATTTGTATAAAGCATTT

TTCTCGCGTAATTTCTGATATTTAACATGTGCTTAAGTTACTTTTTTTTTACTGAGCTGC

AGGGTTCCAAAAATGTAGAAGTACTGAAGGTAGATCCAGGGACATTAAAGGGAGTGAACTT

GAGCACCAAAGCATTTGAGAAAATGAAGAATCTTAGGGTGCTCATAATCGAGGAGTTACAT

ATTAGTGGAGATTTTGGGCTGTTGTCCAAGAAGCTCAAATGGTTGTCTTGGCAAAACTGTC

CTTTAAAATATATACCATCAAATTTTCCAGCTGAGAATCTTGTAGTTCTAGATATGCGGAA

GAGTGATATCGAGGAATTTCAATTGAATTTGCAGGTTTGTTACTCAATTTTACAATTTCAT

GTGTACTGTTATTGCCACTGAGTGAAAGAAAATGTTAATTGAAACTATATTTGGTTTACTT

TTAGTGTTGTAGAAGTTTGAAGAAGCTGAATCTCTCTAATTGCAAGCAACTCAGAAGCACT

CCAAACTTCAATGGTTCACTGAGTCTTGAGATTTTGAATCTCGATGGTTGCCTAAGTCTGA

GGGAGATCCATCCATCAATAGGGAATTTGTCCAGACTAATTAAACTATATATGCGTGGTTG

CGAAAAACTTACGGATCTTCCTAGCAGCATTTGCCAGCTAAAATCCCTTGATTACTTGGAC

ATTGATGGCTGCTCATTTATAAAAACACTGCCAGATAACCTTGGAGATATGAAAAGTCTAA

GACATCTTTCTGCATCTTATACGGGTATAAAACAATTGCCTAGATCTGTTGAAATGCTAAG

AAATCTTAAAATATTGGAAGTGGGAAATCGAATGTTTGGGACCAATATGAGTATTTATGGA

AGAGGAGTCCATCAGATACAATATTCCTTGTCAACTTTTGTATCCGATTTGAGACTTACAT

ACTGTAATTTGTCCGAGGCTGATATTCCTAGGGATATTGGGAGCTCATCCTCCTTAGAACT

TTTAGATTTGAGTGGCAACAGTTTCCATTGTCTACCTTTTGATTTTTCTAAGTTACGATTC

TTGAAGGGGTTGTATTTGATTGACTGTGAGAACCTTCAAACACTCCCGTCAATATCAAATT

TAGAGAAACTTGAAAGAATTGAACTTCAAAATTGCCAAAAATTGGTCAAGATTAGAGAGTT

GGACAACCTCCCTTCTATATGGTCGATCGACATGAGGAATTGTAGTTGTCTGCAGAATCCA

TTCAATGAAAGCTTCTTCAGTGCACCTGCTCTATCATTTCCATCTAGATTAGTCTCTCTCT

CTCTCTCTCCTATCATATTAATGATCTTGAGTCTTTGTCCGATGCAGCATGAAATAGAAAT

TAGCATTTATCTGGAATGCAAAGAGATTCCAGAATGGTGCAGGAATCGAGTAACAACTTCA

TCTATGTGTTTGACTATGCCTACACATAATAAGGAGTATAACTTCTTAGGAATGGTTCTCT

GGTTAGTTTCCGACTTCTCTCATCCATGCTTGTGGATTAGTATTGCCCATAAACAGCCTTC

AATTATGGTGTGGAGTAGTGTTTATACAACACTTGGTACACTTGATGGACACACAGAAGTA

TCATGTGTACGTTACATATCTTACTTACATAGAGCTTTTGATGGCCAGATGATCAAAGGCG

GGGAAACGATAGAAGCGTGGTCTGAAGACTCTACAATAAAGAAGATAGGGATCCATCTGTT

ATATTTGGACGAATATGGTAAAGTTATATCTTTGCCGGGAGACGTGGATCATTCTTATTCT

AAGTACCCAAAAAGAGTTTCAACAGTCTTATCAACTCCTCCTTATAAAAGAGCAAAGTTCT

GAGTCAAGATAATTTTCCTTTAGAGCTAATCAAATTGTATTTATATTACACTATTAATGTG

TAGTTCATCAGTTAATTTTTAATTGATATTGATCTTTTCCCAAATATTTGTTATATATATA

TATTTTTTGTGTTATCAAGTATTTATCTGTCTCCTAGTTCCTATGGACTAAAATGAAAACA

AAAACTAGATAAATTCAATCTGCCATGTACGTAATCTTTTTCCCTTGGCCAAATC

NaChr3_59.2M marker
                                                    >SEQ ID NO: 9
TCCTCAACCTCCACGAACGTGGACCCCTTATCGCGAACGCATAGAACAACCAGGCAGGGCC

CCCAGACCCCTTCTACGTGAACACGAGGACACCCACGCGAACGCGATGAACTGGCAAATCC

ACCCCTTCGTGATCGCGGACCTACTCCCGCGAACGCGATGACCAATTTTTGGTCTGCACTG
```

CTGTGCATTTTCTGCAGAAATTCTCAAGTCCAAACTTCCCGTTCAACCATCCGAAACCACC

CCGAGGCCCCCGGGACCTCAACCAAAAGCACGAACATGACCTATTACCTTATTCAAACTTG

CTCGGGCCATTAAAACGCTATCGTTAACATCAAAATCCGCTAATTTTCTCAAATCAAAGCC

TAAGTTTCTTAAAACCTTCCGAATTGCACATTCGATCAAAAACCCGACCTAAACATCTCCG

AATGACCTGCAACTTTACACACATATCCAAAATCACTTAACGGAGCTACTGCAACTCTCGA

AATCCCATTCCGACCCTCGGATCAGAATCTCGCATACCG

NaChr3_59.7M marker
>SEQ ID NO: 10
AGTCTTCTGCCGCTCCATCTCCAGCGCGGCCTGAGAACAGGGCCACGGAGGCCTCAGGGGT

CGTCCGCCCCAGAGTTGAGTTGGTGCCAAGCGAAGAGGATGAGGAGGAGGAGAGGCCGCTC

GTTAGACGTAGGGTGGATTTTGACGTGACCTCTTCGGCGGTGATCAGCTTAGATTCTCCGC

CGACGGAAGCAGGAGGGGACACAGCAGAGGCGGCTCCAAAAGGGGAGCATTCAGTGGGGGT

TGCCCCGGTTGGCTCAGGCCATGTAGATACCGTCGTTGCGGCGACTGAAGATGTACCACCT

GCCGCTGATAGGGAAGTTGGGTCCTCGGCGGCAGCGGTGACGGAGGAGACGGCCGCTCAGG

CCATTGTTGGTGTTAATGTTGCTGCTCACGCGGCGGAGGCATCGACTTCACGAGGTGCTAA

AGGCCACGGTGCCTTACGTGAAGGGGAGGATTCGGACTCCGACTTGGACCCTGAGGACGTC

CACATGTTCCAGGAGGGCCTCACTCGCCATGAAGTGCACGTGGAGGGGAATTCTCGATATA

TCGAGCTTCCTAATGACCTGAACCTCCTTCTCCAGGAGGAGAATTTGGTGACGCTCTTCGA

AGTGTTGAGCTCAGCGGCGGAGAGCACGTCCGTGCAGGGCATTACGGACGTGGGCCTGATG

GGCGAGGTTGCCGCGAACTGTATAAAGGTAATGGCGAATACTTGGGTCGA

---

The invention claimed is:

1. A transgenic plant comprising, stably incorporated in its genome through gene transformation, a heterologous polynucleotide construct comprising a nucleotide sequence selected from the following (a1)-(a3):

(a1) the nucleotide sequence set forth in SEQ ID NO: 1;

(a2) the nucleotide sequence set forth in SEQ ID NO: 2;

(a3) a nucleotide sequence encoding the amino acid sequence set forth in SEQ ID NO: 3;

wherein the transgenic plant is a solanaceous plant.

2. The transgenic plant of claim 1, wherein the solanaceous plant is tobacco, potato, or tomato.

3. The transgenic plant of claim 1, wherein the transgenic plant comprises resistance to at least one orthotospovirus, relative to a control plant.

4. The transgenic plant of claim 3, wherein the transgenic plant comprises resistance to Tomato spotted wilt virus (TSWV), Impatiens necrotic spot virus (INSV), Groundnut ringspot virus (GRSV), Chrysanthemum stem necrosis virus (CSNV), Tomato zonate spot virus (TZSV), Groundnut bud necrosis virus (GBNV), Mulberry vein banding associated virus (MVBaV), Capsicum chlorosis virus (CaCV), and Calla lily chlorotic spot virus (CCSV), relative to a control plant.

5. A method for conferring or enhancing resistance to at least one orthotospovirus to a solanaceous plant, the method comprising introducing a heterologous polynucleotide construct into at least one plant cell through gene transformation, the polynucleotide construct comprising a nucleotide sequence selected from the following (a1)-(a3):

(a1) the nucleotide sequence set forth in SEQ ID NO: 1;

(a2) the nucleotide sequence set forth in SEQ ID NO: 2;

(a3) a nucleotide sequence encoding the amino acid sequence set forth in SEQ ID NO: 3.

6. The method of claim 5, wherein the polynucleotide construct is stably incorporated into the genome of the plant cell.

7. The method of claim 6, wherein the plant cell is regenerated into a plant comprising in its genome the polynucleotide construct.

8. The method of claim 7, wherein the solanaceous plant is tobacco, potato, or tomato.

9. The method of claim 7, wherein the plant at least comprises resistance to Tomato spotted wilt virus (TSWV), Impatiens necrotic spot virus (INSV), Groundnut ringspot virus (GRSV), Chrysanthemum stem necrosis virus (CSNV), Tomato zonate spot virus (TZSV), Groundnut bud necrosis virus (GBNV), Mulberry vein banding associated virus (MVBaV), Capsicum chlorosis virus (CaCV), and Calla lily chlorotic spot virus (CCSV), relative to a control plant.

* * * * *